(12) United States Patent
Buckland et al.

(10) Patent No.: US 9,498,121 B2
(45) Date of Patent: Nov. 22, 2016

(54) SURGICAL MICROSCOPES USING OPTICAL COHERENCE TOMOGRAPHY AND RELATED SYSTEMS

(71) Applicant: Bioptigen, Inc., Morrisville, NC (US)

(72) Inventors: Eric L. Buckland, Hickory, NC (US); Nestor O. Farmiga, Rochester, NY (US); Robert H. Hart, Cary, NC (US); Andrew Murnan, Saratoga Springs, NY (US); Christopher Saxer, Chapel Hill, NC (US)

(73) Assignee: Bioptigen, Inc., Morrisville, NC (US)

( * ) Notice: Subject to any disclaimer, the term of this patent is extended or adjusted under 35 U.S.C. 154(b) by 0 days.

(21) Appl. No.: 14/745,980

(22) Filed: Jun. 22, 2015

(65) Prior Publication Data
US 2015/0305618 A1    Oct. 29, 2015

Related U.S. Application Data

(60) Continuation of application No. 14/302,793, filed on Jun. 12, 2014, now Pat. No. 9,060,712, which is a
(Continued)

(51) Int. Cl.
*A61B 3/14* (2006.01)
*A61B 3/00* (2006.01)
(Continued)

(52) U.S. Cl.
CPC .............. *A61B 3/102* (2013.01); *A61B 3/13* (2013.01); *G01B 9/02039* (2013.01);
(Continued)

(58) Field of Classification Search
CPC .......... A61B 3/14; A61B 3/12; A61B 3/103; A61B 3/152; A61B 3/113; A61B 3/1225; A61B 3/032; A61B 3/1015
USPC ....... 351/206, 200, 205, 208–210, 221, 243, 351/246
See application file for complete search history.

(56) References Cited

U.S. PATENT DOCUMENTS 4,167,302 A   9/1979   Karasawa
4,431,258 A   2/1984   Fye
(Continued)

FOREIGN PATENT DOCUMENTS

EP   0 697 611 A2   2/1996
EP   1 659 438 B1   3/2009
(Continued)

OTHER PUBLICATIONS

Brandenburg R. et al., "Real-time in vivo imaging of dental tissue by means of optical coherence tomography (OCT)", *Optics Communications*, 227 (2003), 203-211.
(Continued)

*Primary Examiner* — DaWayne A Pinkney
(74) *Attorney, Agent, or Firm* — Myers Bigel, P.A.

(57) ABSTRACT

Some embodiments of the present inventive concept provide optical coherence tomography (OCT) systems for integration with a microscope. The OCT system includes a sample arm coupled to the imaging path of a microscope. The sample arm includes an input beam zoom assembly including at least two movable lenses configured to provide shape control for an OCT signal beam; a scan assembly including at least one scanning mirror and configured for telecentric scanning of the OCT signal beam; and a beam expander configured to set the OCT signal beam diameter incident on the microscope objective. The shape control includes separable controls for numerical aperture and focal position of the imaged OCT beam.

17 Claims, 47 Drawing Sheets

Related U.S. Application Data division of application No. 13/836,576, filed on Mar. 15, 2013, now Pat. No. 8,777,412.

(60) Provisional application No. 61/620,645, filed on Apr. 5, 2012.

(51) Int. Cl.

| | | |
|---|---|---|
| A61B 3/10 | (2006.01) | |
| G01B 9/02 | (2006.01) | |
| A61B 3/13 | (2006.01) | |
| G02B 21/00 | (2006.01) | |
| G02B 21/02 | (2006.01) | |
| G02B 27/00 | (2006.01) | |
| G02B 27/09 | (2006.01) | |
| G02B 27/14 | (2006.01) | |
| A61B 5/00 | (2006.01) | |
| G02B 1/11 | (2015.01) | |

(52) U.S. Cl.
CPC ..... *G01B 9/02091* (2013.01); *G02B 21/0012* (2013.01); *G02B 21/02* (2013.01); *G02B 27/0031* (2013.01); *G02B 27/0955* (2013.01); *G02B 27/141* (2013.01); *A61B 5/0066* (2013.01); *G02B 1/11* (2013.01); *G02B 21/0048* (2013.01)

(56) References Cited

U.S. PATENT DOCUMENTS

| | | |
|---|---|---|
| 4,544,243 A | 10/1985 | Munnerlyn |
| 4,561,080 A | 12/1985 | Yamazaki |
| 4,930,868 A | 6/1990 | Gerlitz |
| 5,055,663 A | 10/1991 | Morimoto et al. |
| 5,061,018 A | 10/1991 | Pederson et al. |
| 5,103,439 A | 4/1992 | Bierhoff et al. |
| 5,168,386 A | 12/1992 | Galbraith |
| 5,220,450 A | 6/1993 | Iizuka |
| 5,491,524 A | 2/1996 | Hellmuth et al. |
| 5,493,109 A | 2/1996 | Wei et al. |
| 5,795,295 A | 8/1998 | Hellmuth et al. |
| 5,889,750 A | 3/1999 | Summers et al. |
| 5,907,431 A | 5/1999 | Stuttler |
| 6,004,314 A | 12/1999 | Wei et al. |
| 6,333,781 B1 | 12/2001 | Shigematsu |
| 6,419,360 B1 | 7/2002 | Hauger et al. |
| 6,426,840 B1 | 7/2002 | Partanen et al. |
| 6,451,010 B1 | 9/2002 | Angeley |
| 6,678,090 B2 | 1/2004 | Spink |
| 6,763,259 B1 | 7/2004 | Hauger et al. |
| 6,943,942 B2 | 9/2005 | Horiguchi et al. |
| 7,072,047 B2 | 7/2006 | Westphal et al. |
| 7,145,727 B2 | 12/2006 | Hsieh |
| 7,246,905 B2 | 7/2007 | Benedikt et al. |
| 7,387,385 B2 | 6/2008 | Sander |
| 7,408,705 B2 | 8/2008 | Horiguchi et al. |
| 7,481,536 B2 | 1/2009 | Wong et al. |
| 7,669,262 B2 | 3/2010 | Skripps et al. |
| 7,699,468 B2 | 4/2010 | Gaida |
| 7,719,692 B2 | 5/2010 | Izatt et al. |
| 7,733,497 B2 | 6/2010 | Yun et al. |
| 7,742,174 B2 | 6/2010 | Izatt et al. |
| 7,791,794 B2 | 9/2010 | Reimer et al. |
| 7,839,494 B2 | 11/2010 | Reimer et al. |
| 7,889,423 B2 | 2/2011 | Reimer et al. |
| 7,901,080 B2 | 3/2011 | Hauger et al. |
| 8,023,120 B2 | 9/2011 | Reimer et al. |
| 8,049,873 B2 | 11/2011 | Hauger et al. |
| 8,189,192 B2 | 5/2012 | Huening et al. |
| 8,310,674 B2 | 11/2012 | Huening et al. |
| 8,348,427 B2 | 1/2013 | Buckland et al. |
| 8,401,257 B2 | 3/2013 | Izatt et al. |
| 8,425,037 B2 | 4/2013 | Uhlhorn et al. |
| 8,625,104 B2 | 1/2014 | Izatt et al. |
| 8,693,745 B2 | 4/2014 | Izatt et al. |
| 8,777,412 B2 | 7/2014 | Buckland et al. |
| 8,797,530 B2 | 8/2014 | Saxer et al. |
| 8,864,309 B2 | 10/2014 | Buckland |
| 2002/0173778 A1 | 11/2002 | Knopp et al. |
| 2003/0139736 A1 | 7/2003 | Sander |
| 2003/0218755 A1 | 11/2003 | Wei et al. |
| 2004/0036838 A1 | 2/2004 | Podoleanu et al. |
| 2004/0109231 A1 | 6/2004 | Haisch et al. |
| 2005/0068881 A1* | 3/2005 | Kimura et al. .......... 369/112.23 |
| 2005/0277913 A1 | 12/2005 | McCary |
| 2005/0283058 A1 | 12/2005 | Choo-Smith et al. |
| 2006/0050408 A1 | 3/2006 | Hakko et al. |
| 2007/0030446 A1 | 2/2007 | Su et al. ........................ 351/205 |
| 2007/0258095 A1 | 11/2007 | Olivier et al. ................ 356/479 |
| 2007/0282313 A1 | 12/2007 | Huang et al. |
| 2007/0291277 A1 | 12/2007 | Everett et al. |
| 2008/0004610 A1 | 1/2008 | Miller et al. |
| 2008/0117504 A1 | 5/2008 | Reimer et al. |
| 2008/0133019 A1 | 6/2008 | Andrysek |
| 2008/0198329 A1 | 8/2008 | Gaida |
| 2008/0304144 A1 | 12/2008 | Reimer et al. |
| 2009/0141240 A1 | 6/2009 | Weitz et al. |
| 2009/0244485 A1 | 10/2009 | Walsh et al. |
| 2009/0257065 A1 | 10/2009 | Hauger et al. |
| 2010/0309478 A1 | 12/2010 | Reimer et al. |
| 2010/0324542 A1 | 12/2010 | Kurtz |
| 2010/0324543 A1 | 12/2010 | Kurtz |
| 2011/0001926 A1 | 1/2011 | Mann et al. |
| 2011/0028948 A1 | 2/2011 | Raksi et al. ........................ 606/4 |
| 2011/0096291 A1 | 4/2011 | Buckland et al. |
| 2011/0173778 A1 | 7/2011 | Wales |
| 2011/0202046 A1 | 8/2011 | Angeley et al. |
| 2011/0299034 A1 | 12/2011 | Walsh et al. |
| 2012/0026462 A1 | 2/2012 | Uhlhorn et al. |
| 2012/0063660 A1 | 3/2012 | Imamura et al. |
| 2012/0074294 A1 | 3/2012 | Streuber et al. ........... 250/201.9 |
| 2012/0184846 A1 | 7/2012 | Izatt et al. |
| 2012/0197102 A1 | 8/2012 | Hanebuchi et al. |
| 2012/0215155 A1 | 8/2012 | Muller et al. |
| 2012/0242988 A1 | 9/2012 | Saxer et al. |
| 2012/0262720 A1 | 10/2012 | Brown et al. |
| 2013/0141695 A1 | 6/2013 | Buckland et al. |
| 2013/0158531 A1 | 6/2013 | Goldshleger et al. |
| 2013/0172861 A1 | 7/2013 | Youssefi |
| 2013/0190737 A1 | 7/2013 | Muller et al. |
| 2013/0265545 A1 | 10/2013 | Buckland et al. |
| 2014/0194860 A1 | 7/2014 | Dick et al. |

FOREIGN PATENT DOCUMENTS

| | | |
|---|---|---|
| EP | 2 322 083 A1 | 5/2011 |
| WO | WO 2008/034609 A1 | 3/2008 |
| WO | WO 2011/091326 A1 | 7/2011 |
| WO | WO 2013/059719 A1 | 4/2013 |
| WO | WO 2013/151879 A1 | 10/2013 |

OTHER PUBLICATIONS

Davis A.M. et al., "In vivo spectral domain optical coherence tomography volumetric imaging and spectral Doppler velocimetry of early stage embryonic chicken heart development", *J. Opt. Soc. Am. A.*, vol. 25, No. 12, Dec. 2008, pp. 3134-3143.

Geerling G. et al., "Intraoperative 2-Dimensional Optical Coherence Tomography as a New Tool for Anterior Segment Surgery", *Arch Ophthalmol.* 2005;123;253-257.

Izatt J.A. et al., "Optical coherence microscopy in scattering media", *Optics Letters*, vol. 19, No. 8, Apr. 15, 1994, pp. 590-592.

Izatt S. D. et al., "In Vivo Imaging of the Drosophila Melanogaster heart Using a Novel Optical Coherence Tomography Microscope", *Proc. of SPIE*, vol. 5701, pp. 122-127, Downloaded from SPIE Digital Library on May 16, 2011.

Maschlo M.D. et al., "Three-dimensional in vivo scanning microscopy with inertia-free focus control", Optics Letters, Sep. 1, 2011, vol. 36, No. 17, pp. 3503-3505.

(56) References Cited

OTHER PUBLICATIONS

Murali, Supraja "*Design of a Dynamic Focusing Microscope Objective for OCT Imaging*", MS Thesis, University of Central Florida, Orlando, Florida, 2005.

Notification of Transmittal of the International Search Report and the Written Opinion of the International Searching Authority, or the Declaration, PCT/US2013/034544, Jul. 3, 2013.

Qi B. et al., "Dynamic focus control in high-speed optical coherence tomography based on a microelectromechanical mirror", *Optics Communications*, 232 (2004), 123-128.

Radhakrishnan S. et al., "Real-Time Optical Coherence Tomography of the Anterior Segment at 1310 nm", *Arch Ophthalmol.*, 2001;119:1179-1185.

Tao Y.K. et al., "Intraoperative spectral domain optical coherence tomography for vitreoretinal surgery", *Optics Letters*, Oct. 15, 2010, vol. 35, No. 20, pp. 3315-3317.

Notification Concerning Transmittal of International Preliminary Report on Patentability, PCT/US2013/034544, Oct. 7, 2014, 8 pages.

Invitation to Pay Additional Fees and, Where Applicable, Protest Fees, PCT/US2014/048552, Oct. 31, 2014.

International Search Report and Written Opinion Corresponding to International Application No. PCT/US2014/053113; Date of Mailing: Dec. 2, 2014; 11 Pages.

Notification of Transmittal of the International Search Report and the Written Opinion of the International Searching Authority, or the Declaration, PCT/US2014/048552; Feb. 2, 2015, 15 Pages.

Notification of Transmittal of the International Search Report and the Written Opinion of the International Searching Authority, or the Declaration, PCT/US2014/040836, Feb. 4, 2015, 15 pages.

Notification Concerning Transmittal of International Preliminary Report on Patentability, PCT/US2014/040836, Dec. 17, 2015.

Notification Concerning Transmittal of International Preliminary Report on Patentability, PCT/US2014/048552, Feb. 11, 2016.

First Office Action, Chinese Patent Application No. 201380029541.0; Feb. 22, 2016, 15 pages.

Dal Maschio et al. "Three-dimensional in vivo scanning microscopy with inertia-free focus control," Optics Letters, vol. 36, No. 17, Sep. 1, 2011, pp. 3503-3505.

Notification of Transmittal of the International Search Report and the Written Opinion of the International Searching Authority, of the Declaration, PCT/US2012/067951, Mar. 5, 2013.

\* cited by examiner a: COLLIMATOR DOUBLET
b: POSITIVE SINGLET
c: NEGATIVE SINGLET
d: POSITIVE SINGLET a: DOUBLET NEAREST GALVO #1
b: SINGLET
c: SINGLET
d: DOUBLET
e: CONJUGATE PLANE
f: DOUBLET
g: SINGLET
h: SINGLET
i: DOUBLET NEAREST GALVO #2

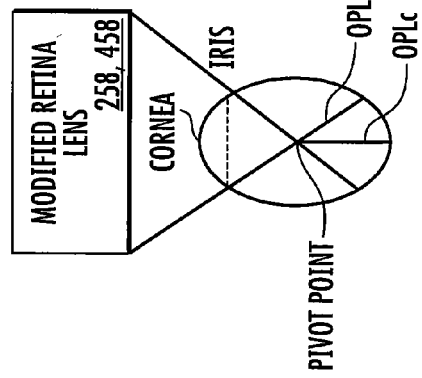
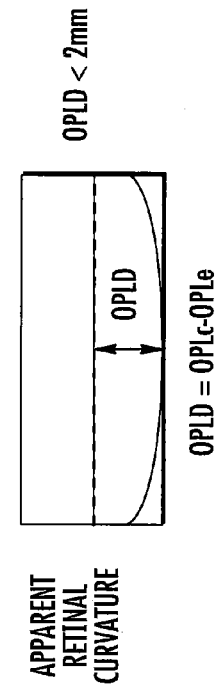
FIG. 18B
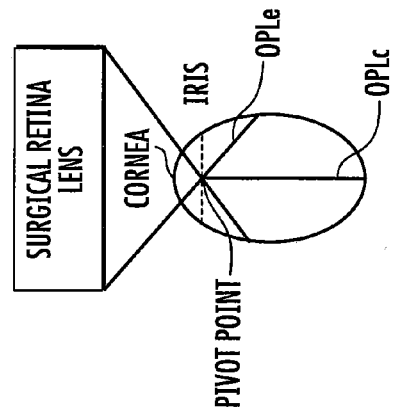
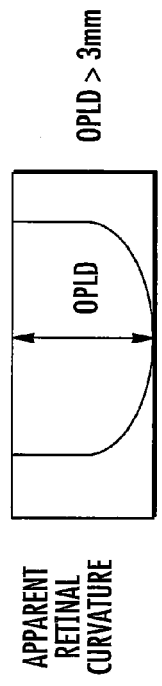
FIG. 18A

SURGICAL MICROSCOPES USING OPTICAL COHERENCE TOMOGRAPHY AND RELATED SYSTEMS

CLAIM OF PRIORITY

The present application claims priority to and is a continuation of U.S. patent application Ser. No. 14/302,793, filed Jun. 12, 2014, which claims priority to and is a divisional of U.S. application Ser. No. 13/836,576, filed Mar. 15, 2013, now U.S. Pat. No. 8,777,412, which claims priority from U.S. Provisional Application No. 61/620,645, filed Apr. 5, 2012, the disclosures of which are hereby incorporated herein by reference as if set forth in their entirety.

STATEMENT OF GOVERNMENT SUPPORT

This inventive concept was funded in-part with government support under Grant Application ID R44EY018021-03 by the National Institutes of Health, National Eye Institute. The United States Government has certain rights in this inventive concept.

FIELD

The present inventive concept relates to surgical microscopes and, more particularly, to ophthalmic surgical microscopes using optical coherence tomography (OCT).

BACKGROUND

Surgical microscopes provide a magnified view of the operating field to the surgeon. Ophthalmic surgical microscopes are, commonly stereo zoom microscopes with binocular view ports for the surgeon, and frequently have one or two observer view ports at ninety degrees (left and right) to the surgeon. The working distance between the objective lens of the microscope and the surface of a patient eye may range from about 100 mm to about 200 mm. At this working distance, which provides a suitable field of access for the manual work of the surgeon, the field of view within a patient eye may be quite limited. It is quite common to use an intermediate lens, such as the Binocular Indirect Ophthalmo Microscope (BIOM) of Oculus Optikgerat, to modify the magnification and field of view for the surgeon. This intermediate lens is mounted to the under-carriage of the microscope head, and includes mechanics to adjust focus, and to flip the lens into and out of the field of view of the microscope.

Other illumination or imaging devices may also be used in the surgical field. Ideally, all illumination and imaging sources would be directly integrated coaxial to and within the optical path of the operating microscope, without impacting the operating field for the surgeon, the observers, the anesthesiologists, and the like. It is still desirable to provide a readily maneuverable mount for imaging and other accessories that is closely coupled to the surgical field, utilizing the mechanical controls and attributes that are already integral to a well-functioning operating microscope, without degrading the visual attributes of the operating microscope.

A particular case of interest is the incorporation of optical coherence tomography (OCT) imaging into the surgical visualization practice. OCT provides high resolution imaging of ocular tissue microstructure, and is showing great promise to provide information to the surgeon that will improve therapeutic outcomes, and reduce the total economic burdens of surgery by reducing risk and reducing re-work.

Conventional frequency domain OCT (FDOCT) systems will now be discussed to provide some background related to these systems. Referring first to FIG. 1A, a block diagram of an FDOCT retinal imaging system will be discussed. As illustrated in FIG. 1A, the system includes a broadband source 100, a reference arm 110 and a sample arm 140 coupled to each other by a beamsplitter 120. The beamsplitter 120 may be, for example, a fiber optic coupler or a bulk or micro-optic coupler. The beamsplitter 120 may provide from about a 50/50 to about a 90/10 split ratio. As further illustrated in FIG. 1A, the beamsplitter 120 is also coupled to a wavelength or frequency sampled detection module 130 over a detection path 106 that may be provided by an optical fiber.

As further illustrated in FIG. 1A, the source 100 is coupled to the beamsplitter 120 by a source path 105. The source 100 may be, for example, a continuous wave broadband superluminescent diode, a pulsed broadband source, or tunable source. The reference arm 110 is coupled to the beamsplitter 120 over a reference arm path 107. Similarly, the sample arm 140 is coupled to the beamsplitter 120 over the sample arm path 108. The source path 105, the reference arm path 107 and the sample arm path 108 may all be provided by optical fiber or a combination of optical fiber, free-space, and bulk- or micro-optical elements.

As illustrated in FIG. 1A, the reference arm of the FDOCT retinal imaging system may include a collimator assembly 180, a variable attenuator 181 that may include a neutral density filter or a variable aperture, a mirror assembly 182, a reference arm variable path length adjustment 183 and a path length matching position 150, i.e. optical path length matching between the reference arm path length and the sample arm path length to the subject region of interest. As further illustrated, the sample arm 140 may include a dual-axis scanner assembly 190 and an objective lens with variable focus 191.

The sample illustrated in FIG. 1A is an eye including a cornea 195, iris/pupil 194, ocular lens 193 and retina 196. A representation of an FDOCT imaging window 170 is illustrated near the retina 196. The retinal imaging system relies on the objective lens plus the optics of the subject eye, notably cornea 195 and ocular lens 193, to image the posterior structures of the eye. As further illustrated the region of interest 170 within the subject is selected through coordination of the focal position 196 and reference arm path length adjustment 183, such that the path length matching position 197 within the subject is at the desired location.

Referring now to FIG. 1B, a block diagram illustrating a FDOCT corneal (anterior) imaging system will be discussed. As illustrated therein, the system of FIG. 1B is very similar to the system of FIG. 1A. However, the objective lens variable focus need not be included, and is not included in FIG. 1B. The anterior imaging system of FIG. 1B images the anterior structures directly, without reliance on the optics of the subject to focus on the anterior structures.

As discussed above, ophthalmic surgical microscopes can provide surgeons a magnified view of various areas of the eye on which they are operating. However, there are many ophthalmic surgical procedures that may benefit from the kind of high-resolution depth-resolved imaging provided by Optical Coherence Tomography (OCT). Thus, integrating an OCT system into a surgical microscope may provide greater capabilities and enable procedures that currently cannot be performed with conventional stereoscopic imaging.

As illustrated in FIG. 1C, there are various regions of interest in the eye, which may require different OCT imaging characteristics. For example, referring to FIG. 1C, region 1, the corneal region, typically requires relatively high resolution OCT imaging. A fairly large depth-of-focus (DOF) is desirable to allow the entire corneal structure to be imaged. Such imaging is desirable in support of cornea transplant procedures. Likewise, imaging of the crystalline lens, region 2, benefits from high resolution imaging of the capsular structure. A large DOF is required to visualize the entire lens at one time. By contrast, structures on the retina, region 3, lie in a constrained depth region, and tend to be very fine. Thus, retinal imaging typically requires very high resolution, but not necessarily a large DOF.

Existing surgical microscopes incorporating OCT will be discussed with respect to FIGS. 1D and 1E. Referring first to FIG. 1D, like reference numerals refer back to FIGS. 1A and 1B. However, as illustrated in FIG. 1D, a stereo zoom microscope 160 has been incorporated into the sample arm path 108. As illustrated, the surgical microscope 160 includes two oculars (binocular view ports) 162 for the surgeon to view the sample 199. The surgical microscope 160 of FIG. 1D includes a beamsplitter 161, where the beamsplitter may be a dichroic filter, and an objective lens 163 positioned beneath the dichroic filter 161. As further illustrated the sample arm path 108 is coupled to a collimator 165 that forms a beam exiting an optical fiber and a pair of galvos 190 which directs the beam to the dichroic filter 161 integrated into the infinity space of the microscope between the ocular paths 162 and the main objective 163. The beam reflects off the dichroic filter 161 and through the objective lens 163 to image the sample 199, which may be an eye or any other accessible region of a subject. The microscope 160 illustrated in FIG. 1D is a static surgical microscope, i.e. dynamic adjustments to the focal lengths are not possible; focal changes are possible only by exchange of optical elements (installing a new main objective lens 163) or changing the working distance between the microscope 160 and the subject 199.

Referring now to FIG. 1E another design of a surgical microscope incorporating OCT will be discussed. Surgical microscopes illustrated in FIG. 1E are discussed in U.S. Pat. No. 8,366,271 to Izatt et al., the disclosure of which is incorporated herein by referenced as if set forth in its entirety. As illustrated in FIG. 1E, the surgical microscope system of FIG. 1E is similar to the system of FIG. 1D except a telescope lens assembly set 167 is provided between the pair of galvos 190 and the dichroic filter 161 of the surgical microscope 163. Thus, in the system of FIG. 1E, the beam travels through the galvos 190 into the telescope lens set 167 and then through the dichroic filter 161 through the objective lens 163 to image the sample 199. The presence of the telescope lens set 167 provides beam shaping to maximize the numerical aperture of the system, potentially improving the lateral resolution of the images produced by the system, however, the system illustrated in FIG. 1E offers limited flexibility in modifying or controlling the characteristic of the scanning beam.

SUMMARY

Some embodiments of the present inventive concept provide optical coherence tomography (OCT) systems for integration with a microscope. The OCT system includes a sample arm coupled to the imaging path of a microscope. The sample arm includes an input beam zoom assembly including at least two movable lenses configured to provide shape control for an OCT signal beam; a scan assembly including at least one scanning mirror and configured for telecentric scanning of the OCT signal beam; and a beam expander configured to set the OCT signal beam diameter incident on the microscope objective. The shape control includes separable controls for numerical aperture and focal position of the imaged OCT beam.

In further embodiments, the OCT signal beam may be coupled to the microscope imaging path through a beamsplitter. The beamsplitter may be set at an angle of not less than 48 degrees and not greater than 55 degrees relative to the optical axis of the microscope objective. The beamsplitter may be a dichroic filter.

In still further embodiments, the beam expander may include an aberration compensator.

In some embodiments, a path length adjustment may be included in the sample arm between the beam expander and the microscope objective to accommodate for variances in the focal length of the microscope objective.

In further embodiments, the telecentric scan assembly may include a first scanning having a first image that is relayed onto a second scanning mirror. An exit pupil of the OCT sample arm may be in the back focal plane of the microscope objective. The exit pupil of the OCT sample arm optics may be a virtual exit pupil.

In still further embodiments, the input beam zoom may include first and second positive lenses and a negative lens therebetween. The numerical aperture of the system may be set by controlling a first distance between the first positive lens and the negative lens and a second distance between the negative lens and the second positive lens. A focus of the OCT system may be set by controlling a position of the second positive lens for a particular setting of numerical aperture.

In some embodiments of the present inventive concept, at least a portion of the OCT path may occupy a center channel of the microscope. The OCT beam may be directed towards a center field of the microscope objective. Any ocular paths of the microscope may be situated peripherally to this center field of the microscope objective.

In further embodiments, the beamsplitter may occupy an area less than a clear aperture of the microscope objective.

In still further embodiments, the sample may be an eye. A retinal imaging lens assembly may be situated between the microscope objective and the eye. The retinal imaging lens assembly may image a conjugate of the scanning mirrors to a position posterior to the pupil plane of eye. The retinal imaging lens assembly may include at least one lens with at least one aspheric surface.

In some embodiments, an objective lens may be provided in common with a microscope. The objective lens may be anti-reflection coated for operation in a visible spectral range relevant to the microscope visualization and an infrared spectral range relevant to the OCT system. The microscope objective may be an achromatic doublet comprising a crown glass positive lens component and flint glass negative lens component.

Further embodiments of the present inventive concept provide methods of optical coherence tomography (OCT) imaging in conjunction with a surgical procedure. The methods include visualizing a first region of interest having an image depth of $z_1$ using a spectral sampling interval of $v_1$; and visualizing a second region of interest having an image depth of $z_2$ using a spectral sampling interval $v_2$, wherein $v_2$ is greater than or equal to $2v_1$.

In still further embodiments, visualizing the first region of interest may be performed with a scanning system having a first numerical aperture. Visualizing the second region of interest may be performed with the scanning system having a second numerical aperture, different from the first numerical aperture, the second numerical aperture being greater than the first numerical aperture.

Some embodiments of the present inventive concept provided methods of optical coherence tomography (OCT) imaging in conjunction with a surgical procedure. The method includes establishing a first setting of a region of interest for OCT imaging; establishing a first numerical aperture and a first focal position for the OCT imaging; acquiring at least a first OCT image; calculating at least a first clinical parameter from the at least first OCT image; performing a surgical procedure; acquiring at least a second OCT image; and computing at least a second clinical parameter from the at least a second OCT image.

Further embodiments of the present inventive concept provide methods of optical coherence tomography (OCT) imaging in conjunction with a surgical procedure. The method includes setting a first region of interest within a surgical sample for OCT imaging; acquiring at least a first OCT image of the first region of interest; performing a surgical procedure involving the first region of interest; setting a second region of interest within the surgical sample for OCT imaging, the second region of interest being at least partially different from the first region of interest; and acquiring at least a second OCT image of the second region of interest.

In still further embodiments, a first reference arm position, a first numerical aperture, and a first focal position may be set for acquiring the OCT image in the first region of interest. At least one of a reference arm position, a numerical aperture and a focal position maybe changed for acquiring the OCT image in the second region of interest.

BRIEF DESCRIPTION OF THE DRAWINGS

FIGS. 18A and 18B are block diagrams illustrating conventional configurations for surgical retinal imaging and a configuration in accordance with embodiments of the present inventive concept, respectively.

DETAILED DESCRIPTION

Figure 1A:
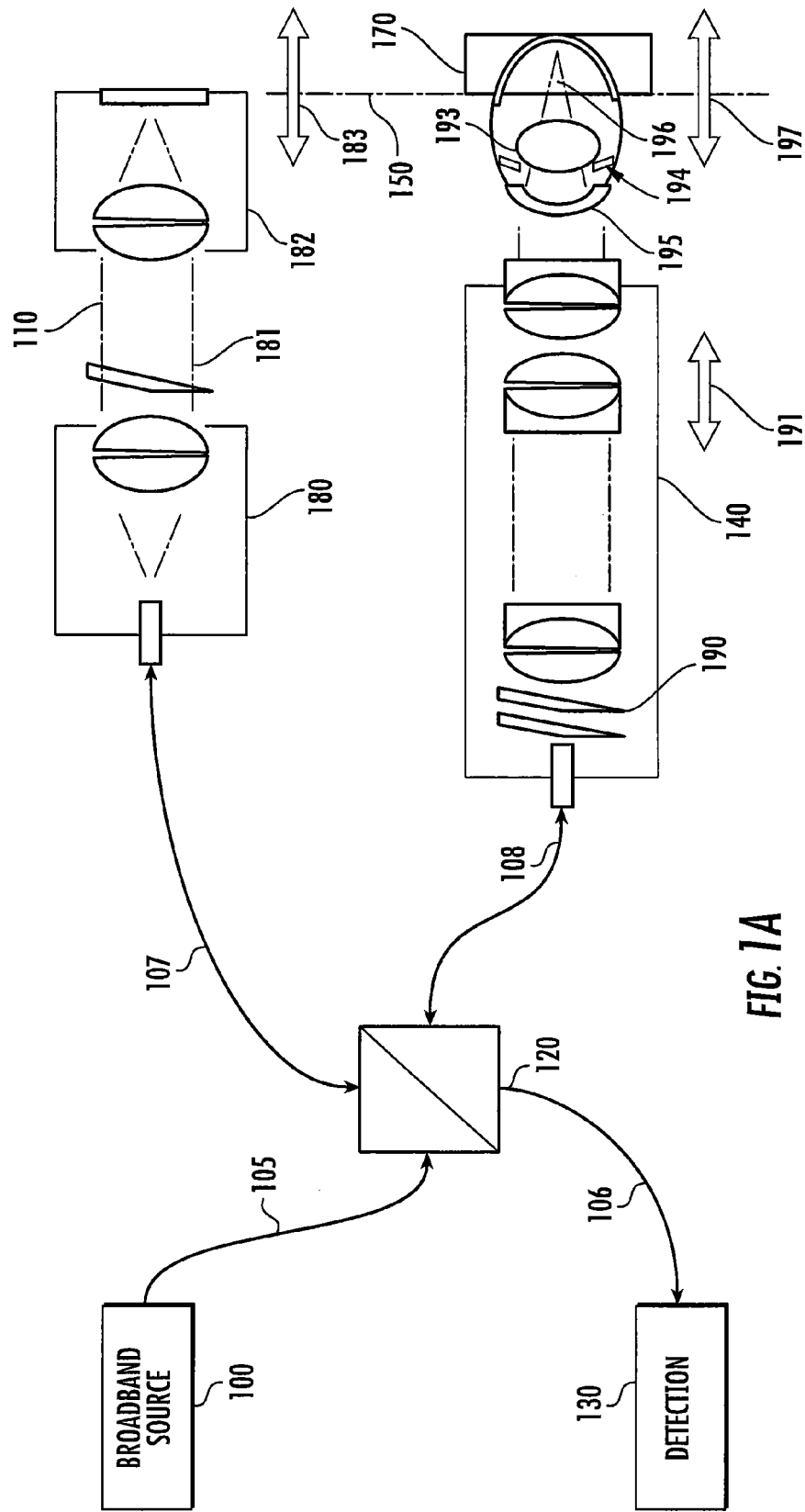
FIG. 1A is a block diagram illustrating an example OCT retinal (posterior) imaging system.
Figure 1B:
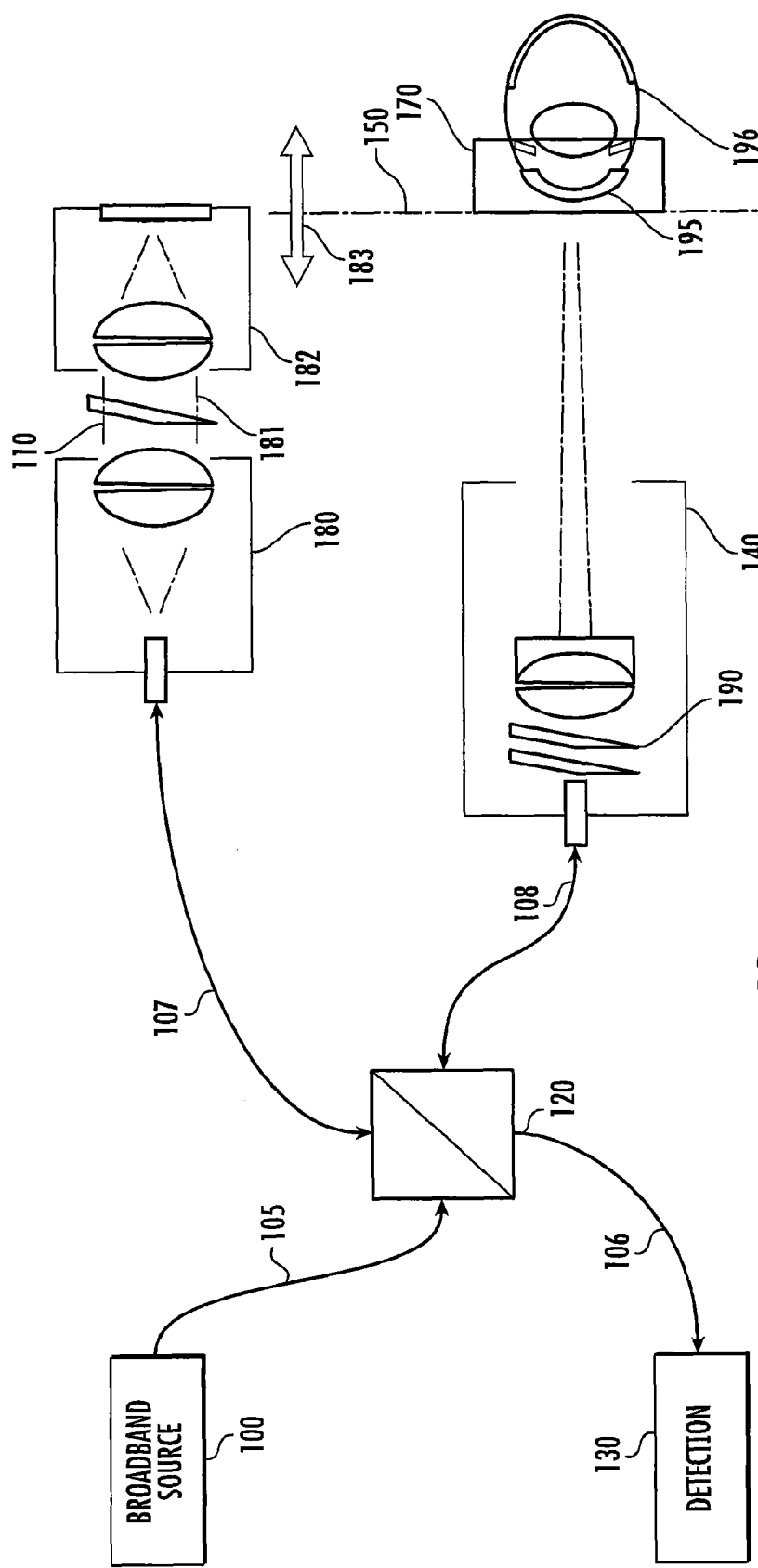
FIG. 1B is a block diagram illustrating an example Optical Coherence Tomography (OCT) cornea (anterior) imaging system.
Figure 1C:
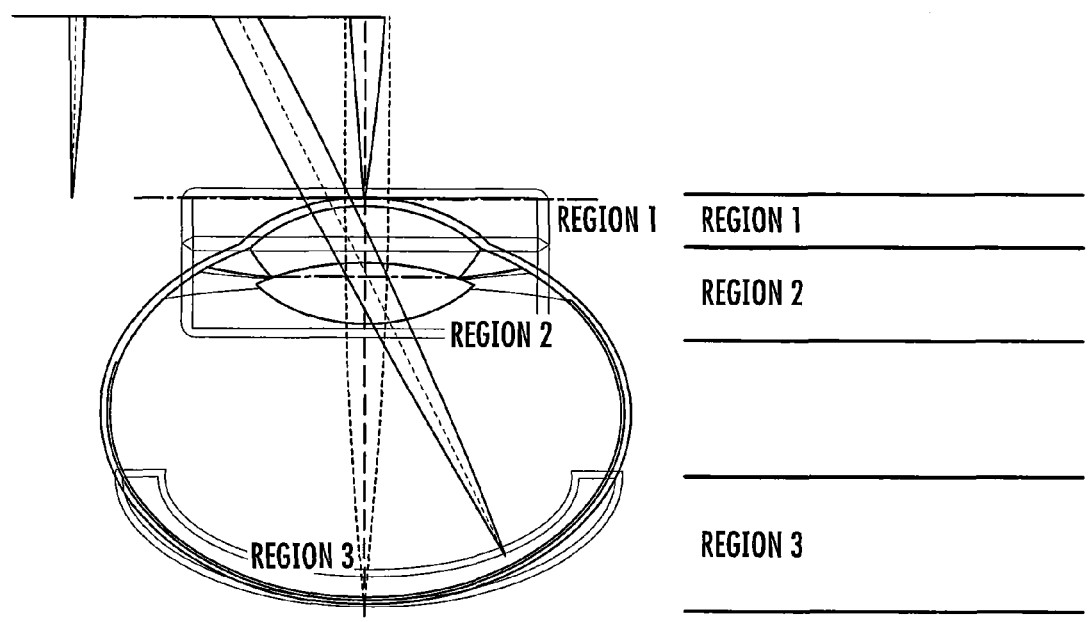
FIG. 1C is a diagram illustrating various regions of interest in the eye.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Although many of the examples discussed herein refer to the sample being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

As discussed above, ophthalmic surgical microscopes can provide surgeons a magnified view of various areas of the eye on which they are operating. However, there are many ophthalmic surgical procedures that may benefit from the kind of high-resolution depth imaging provided by Optical Coherence Tomography (OCT). Thus, integrating an OCT system into a surgical microscope may provide greater capabilities and enable procedures that currently cannot be performed with only conventional stereoscopic imaging. Conventional surgical microscopes incorporating OCT generally provide static imaging incapable of adapting for the region of interest in the sample. Taking the example of an eye, conventional systems cannot typically adapt to the difference imaging requirements for imaging the corneal region, the anterior chamber and crystalline lens, and the structures on the retina.

An ideal OCT surgical microscope system would be adaptable to tailor the imaging characteristics for the various regions of interest. An ideal OCT surgical microscope would have the following set of attributes: true telecentric scanning for accurate representation of subject topography; variable numerical aperture to control the distribution of illumination over a depth of field and to allow control of lateral resolution at the position of focus; variable focus to allow independent control of the OCT focal position relative to the ocular focus of the visual microscope; a wide field of view wherein the scanning optical path length is held maximally constant, both to keep physiopathology within the OCT depth of field and to avoid visual distortions of the scanned field; and adjustability to accommodate a wide range of microscope main objectives, to provide versatility to the surgeon for various surgical procedures. It is further desirable to minimize any alterations to the physical working distances of the microscope to which the surgeon may be accustomed. These distances include the distance between the main objective and the subject, and the distance between the microscope oculars and the subject.

Existing systems do not address all of the desired set of attributes. The standard configuration for OCT scanning places two orthogonal scanning mirrors in close proximity. In such a condition, telecentricity may be optimized along one axis only. Some systems project a first mirror onto a second; this is a necessary but not sufficient condition to achieve telecentricity. One object of this invention is to enable a telecentric scanning system over a wide field of view. In an embodiment of the present invention, the system images to a field flatness of less than 5 micrometers over an area of 400 square millimeters (20 mm field of view).

The telescopic beam expansion proposed in Izatt and other related art is effective at changing a focal position and a numerical aperture, but these parameters are coupled. In such a configuration it is not possible to independently control a focal position and a numerical aperture. One object of this invention is to provide for independent control of a focal position of the scanning OCT beam and the numerical aperture of the beam. In an embodiment of the present invention, the numerical aperture may be controlled such that the beam waist is variable between approximately 9 micrometers and 25 micrometers. Further, in his embodiment the focal position may be adjusted by more than 1.5 mm in the high numerical aperture condition (narrow beam waist) and more than 15 mm in the low numerical aperture condition (wide beam waist), and the focus and numerical aperture may be controlled independently.

In OCT imaging through a BIOM or related surgical retina lens, the optical path length of the scanning OCT beam varies widely across the field of view, such that the retina appears strongly curved, and such that beyond approximately a 50 degree field of view the optical path length difference between the center and the edges of the retinal may be greater than 4 mm. In such a case the periphery of the retina may not visible in the OCT image. It is an object of this invention to present a modified surgical retina lens to equalize the optical path length of an OCT image across a wider field of view. In an embodiment of the present invention, the optical path length difference in an OCT scan across a 100 degree field of view of the retina is less than approximately 2 mm.

In prior presentations of OCT surgical microscopes, the designs envision one fixed main objective for the surgical microscope. No accommodation has been foreseen for adjusting the OCT system to a range of main objectives as may suit the surgeon for different procedures. It is an object of this invention for the sample arm of the OCT system to accommodate a range of main objectives. In an embodiment of this invention, the OCT system adapts to main objectives with a range of focal lengths between 150 mm and 200 mm, with additional embodiments accommodating broader or narrower ranges, or ranges centered around shorter or longer working distances.

In prior presentations of OCT surgical microscopes, a dichroic mirror is injected at 45 degrees to couple the OCT beam into the surgical imaging path. In such a configuration, the path length between the oculars and the subject increases in known proportion to the clear aperture of the main objective. It is an object of this invention to minimize this increase in working lengths without impacting the usable aperture of the main objective. In one embodiment of the invention, the dichroic mirror is set an angle other than 45 degrees, reducing the impact on working distances. In a further embodiment of the present invention a modified main objective is introduced that additionally reduces the impact on working distances. In yet another embodiment of the invention, an OCT center channel configuration is introduced that has still less impact on working distances.

Finally, since an ophthalmic surgical microscope is typically mounted at the end of an articulating arm to provide adjustability and access for the surgeon, an OCT surgical microscope system is typically very compact and lightweight so as not to affect the performance of the microscope.

Accordingly, embodiments of the present inventive concept provide OCT surgical microscopes capable of adapting to the various regions of the sample as will be discussed further herein with respect to FIGS. 2A through 31.

Figure 2A:
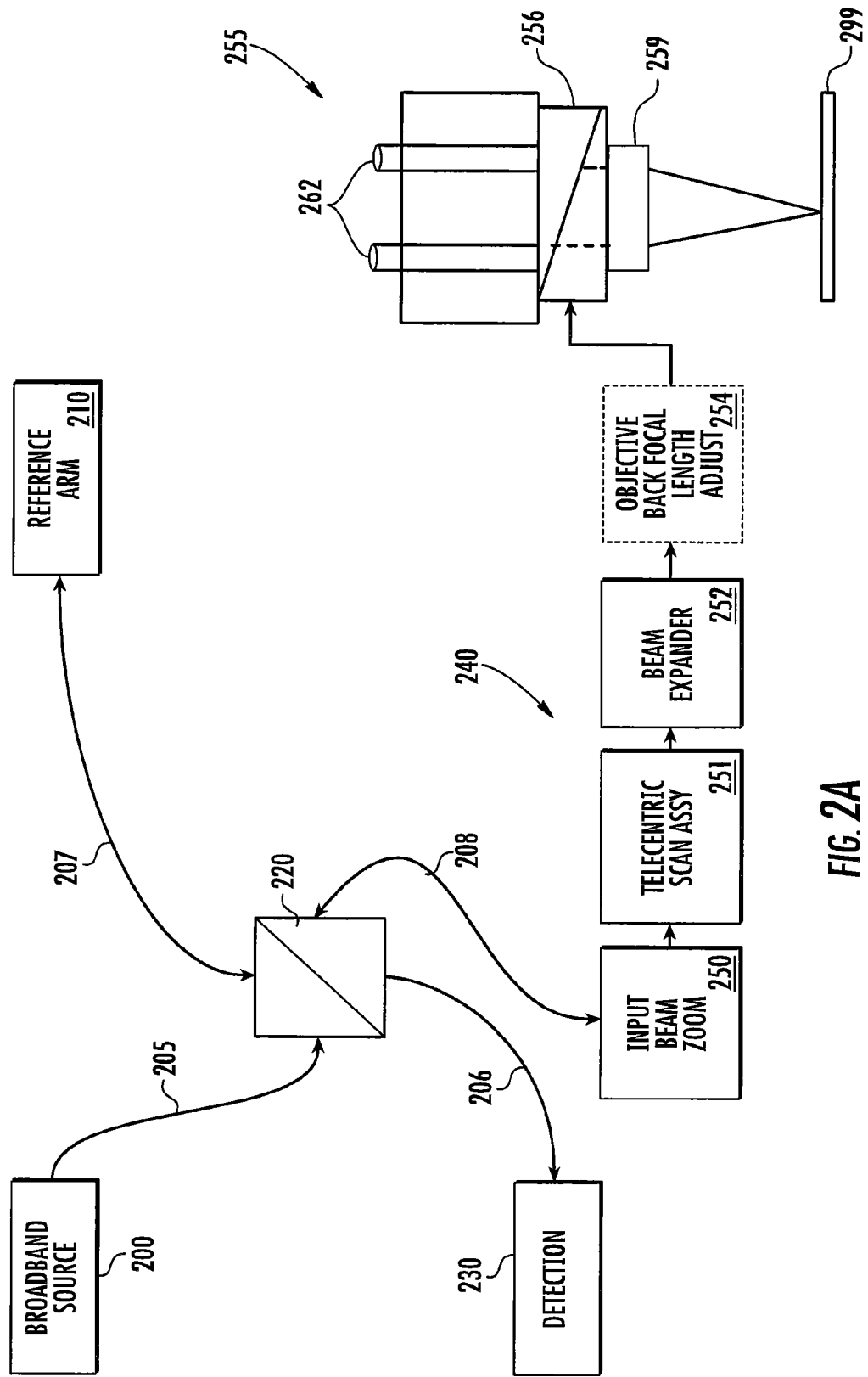
FIG. 2A is a block diagram of a surgical microscope in accordance with some embodiments of the present inventive concept.

Referring first to FIG. 2A, a block diagram of an OCT surgical microscope in accordance with some embodiments of the present inventive concept will be discussed. As illustrated in FIG. 2A, the system includes a broadband source 200, a reference arm 210 and a sample arm 240 coupled to each other by a beamsplitter 220. The beamsplitter 220 may be, for example, a fiber optic coupler or a bulk or micro-optic coupler. The beamsplitter 220 may provide from about a 50/50 to about a 90/10 split ratio. As further illustrated in FIG. 2A, the beamsplitter 220 is also coupled to a wavelength or frequency sampled detection module 230 over a detection path 206 that may be provided by an optical fiber.

As further illustrated in FIG. 2A, the source 200 is coupled to the beamsplitter 220 by a source path 205. The source 200 may be, for example, a superluminescent light emitting diode (SLED) or tunable source. The reference arm 210 is coupled to the beamsplitter 220 over a reference arm path 207. Similarly, the sample arm 240 is coupled to the beamsplitter 220 over the sample arm path 208. The source path 205, the reference arm path 207 and the sample arm path 208 may all be provided by optical fiber.

As further illustrated in FIG. 2A, the surgical microscope 255 includes two oculars (binocular view ports) 262 for the surgeon to view the sample 299. The surgical microscope 255 of FIG. 2A includes a modified dichroic filter 256 and an optimized objective lens 259 in accordance with embodiments discussed herein. The objective lens 259 is positioned beneath the dichroic filter 259 as illustrated in FIG. 2A. A conventional objective lens of a stereo surgical microscope is configured to perform in the visible spectrum. OCT uses the infrared spectrum. Thus, the objective lens 259 in accordance with embodiments discussed herein is modified to extend the wavelength range of the objective lens to allow imaging using OCT and improve the images provided by the surgical microscope using OCT. Furthermore, the objective lens 259 in accordance with embodiments discussed herein may be configured to be thinner than a conventional lens, thus, reducing the working distance. Details of the objective lens 259 in accordance with embodiments of the present inventive concept will be discussed further below.

Referring again to FIG. 2A, as further illustrated the sample arm path 208 is coupled to an input beam zoom (IBZ) 250, a telecentric scan assembly 251, a beam expander 252 and an optional back focal length adjuster 254 which provide the beam to the modified dichroic filter 256 integrated into the surgical microscope. The beam travels through the dichroic filter 256 and into the objective lens 259 to image the sample 299, which may be an eye in some embodiments.

The input beam zoom (IBZ) 250 is provided for input beam shape control. Details of IBZs in accordance with various embodiments discussed herein will be discussed further below. However, IBZs are discussed in detail in commonly assigned U.S. patent application Ser. No. 13/705,867, filed on Dec. 5, 2012, the entire contents of which is hereby incorporated herein by reference as if set forth in its entirety.

The telecentric scan assembly 262 controls the telecentricity of the system. For example, the telecentric scan assembly 262 in accordance with some embodiments may include a telecentric galvo relay lens (GRLs) pair, i.e. a first GRL half (GRLH) and a second GRLH. Each GRLH may be designed as a modified Wild eyepiece. However, telecentric scan assemblies 262 are discussed in detail in commonly assigned U.S. patent application Ser. No. 13/705,867, filed on Dec. 5, 2012, the entire contents of which was incorporated herein in its entirety above.

The beam expander 254 (relay beam expander (RBE)) is an afocal RBE system, the details of which will be discussed further below. The objective back focal length adjuster 254 provides adjustment to a range of main objectives. Thus, embodiments of the present inventive concept provide an OCT system having an objective lens that can adapt to changes in focal length. In other words, typically when the focal length is adjusted at the front, it also needs to be compensated at the back, i.e. back focal length adjustment.

Although the RBE 252 and the objective back focal length adjuster 254 are illustrated in FIG. 2A as separate modules, embodiments of the present inventive concept are not limited to this configuration. For example these two modules 252 and 254 may be combined without departing from the scope of the present inventive concept. Similarly, although the various modules of FIG. 2A are illustrated as separate blocks, these blocks can be combined or separated into more blocks without departing from the scope of the present inventive concept. The OCT system illustrated in FIG. 2A is a system that is optimized for telecentric imaging of the anterior segment of the eye of a subject or other structures directly accessible and visible to the surgical microscope.

Surgical microscopes in accordance with some embodiments of the present inventive concept include an "infinity space." This is a space above the final objective lens before the stereo beams converge. For example, in FIG. 2A, the dichroic filter 256 is inserted into this "infinity space." This space with one or more spectrally diverse or polarization diverse filters may be used to couple additional accessories to the surgical microscope system. Accessories may include, but are not limited to, for example, a video camera, wavefront analysis system, an auto refractor, a scanning laser ophthalmoscope and/or a laser. In some cases the coupling element will be within the infinity space, but in some cases a coupling element may exist elsewhere in the OCT signal path. These embodiments will be discussed further below.

Figure 2B:
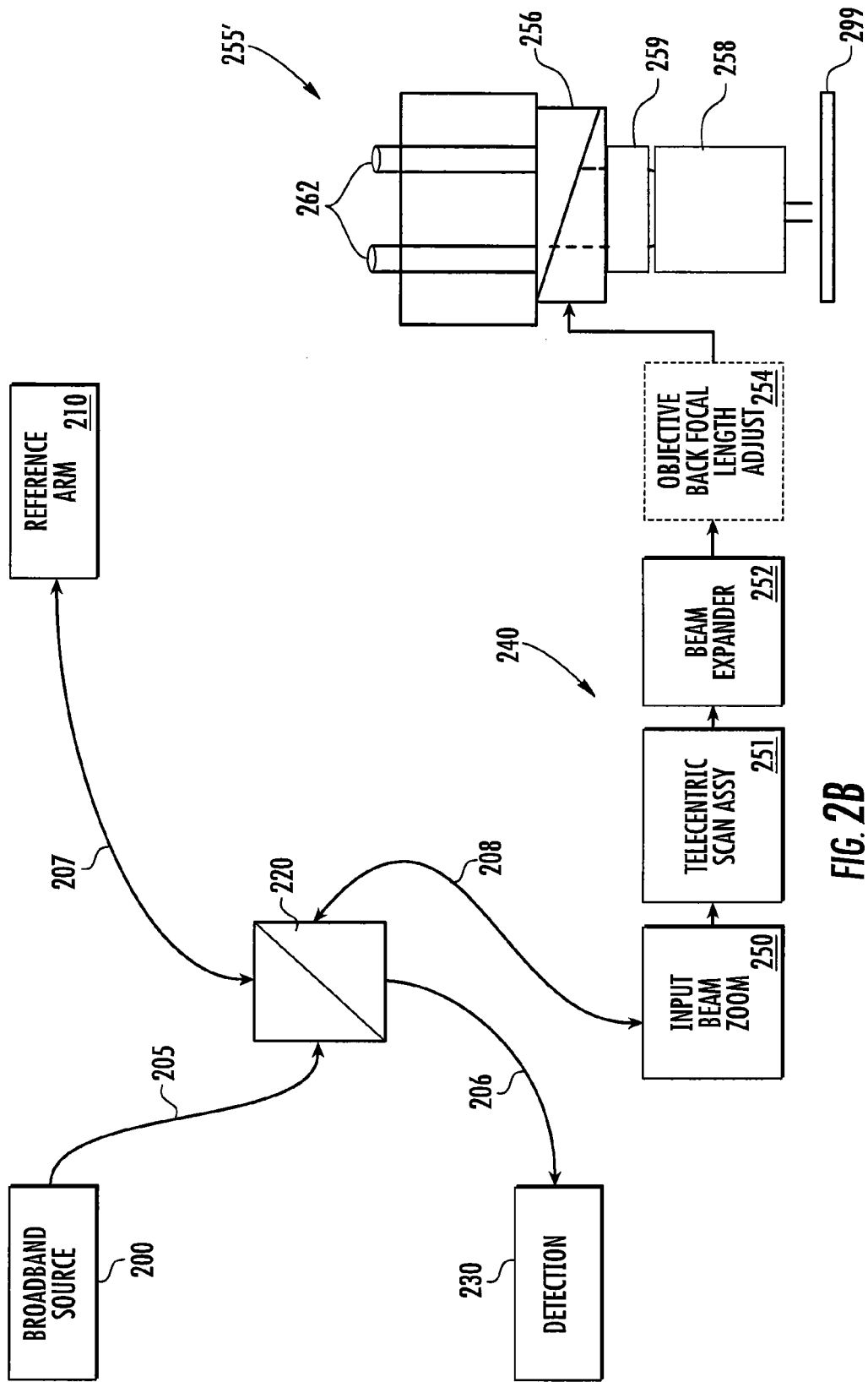
FIG. 2B is a block diagram of a surgical microscope in accordance with some embodiments of the present inventive concept.

Referring now to FIG. 2B, a block diagram of an OCT surgical microscope in accordance with some embodiments of the present inventive concept will be discussed. Like reference numbers in FIG. 2B refer to like elements in FIG. 2A, thus, details of these elements will not be repeated in the interest of brevity. As discussed above, it is quite common to use an intermediate lens, such as the Binocular Indirect Ophthalmo Microscope (BIOM) of Oculus Optikgerat, to modify the magnification and field of view for the surgeon. This intermediate lens is mounted to the under-carriage of the microscope head, and includes mechanics to adjust focus, and to flip the lens into and out of the field of view of the microscope. The BIOM is a retinal imaging lens that allows the microscope to switch between viewing anterior and posterior structures of the eye. However, the BIOM retinal lens is not optimized for use with OCT and thus an improved retinal lens is needed for use with an OCT surgical microscope.

Figure 3:
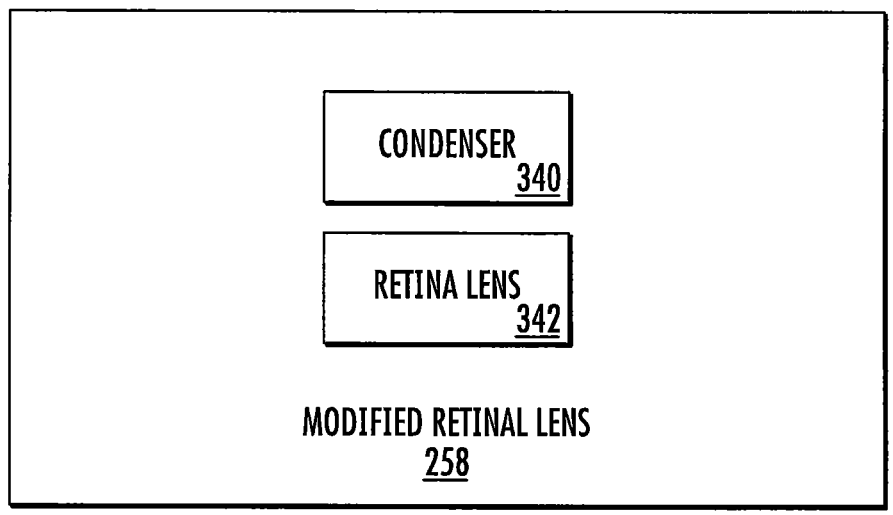
FIG. 3 is a more detailed block diagram of a modified retinal lens illustrated in FIG. 2B used in accordance with some embodiments of the present inventive concept.

As illustrated in FIG. 2B, a retinal lens 258 (surgical retina lens assembly) in accordance with some embodiments of the present inventive concept is positioned beneath the objective lens 259. The retinal lens 258 is modified in accordance with embodiments discussed herein for optimized use with OCT and is configured to adjust accordingly. As illustrated in FIG. 3, the retina lens (surgical retina lens assembly) includes a condenser 340 and a modified retina lens 342. The retina lens 342 allows the focus to be moved down to the retina. Details with respect to the modified surgical retinal lens assembly having various fields of view (FOV) will be discussed further below.

It will be understood that the surgical microscope should be as compact as possible to allow enough room for the surgeon to perform the procedure between the objective lens of the microscope and the sample/patient. In other words, there needs to be a reasonable working distance between the patient and the microscope so the surgeons hands can comfortable perform the procedure. Accordingly, some embodiments of the present inventive concept provide the dichroic filter and the OCT portion of the OCT surgical microscope in a center channel of the surgical microscope itself as will be discussed with respect to FIGS. 4A through 4C below.

Figure 4A:
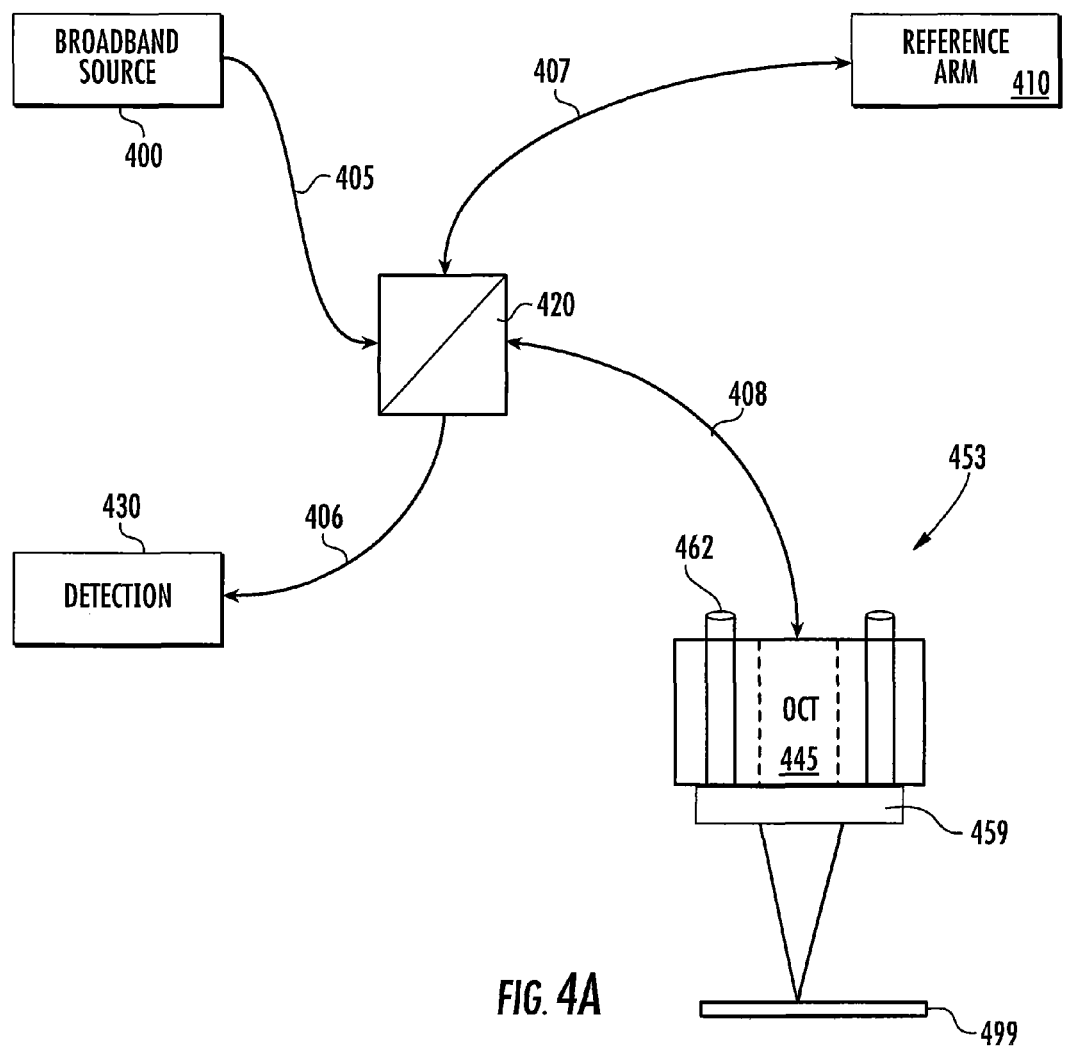
FIG. 4A is a block diagram of an OCT center channel surgical microscope in accordance with some embodiments of the present inventive concept.

Referring first to FIG. 4A, a block diagram of a center channel surgical microscope in accordance with some embodiments of the present inventive concept will be discussed. As illustrated in FIG. 4A, the system includes a broadband source 400, a reference arm 410 and a sample arm integrated in a center channel of the OCT surgical microscope 453. The broadband source 400, the reference arm 410 and the OCT surgical microscope 453 are coupled to each other by a beamsplitter 420. The beamsplitter 420 may be, for example, a fiber optic coupler or a bulk or micro-optic coupler. The beamsplitter 420 may provide from about a 50/50 to about a 90/10 split ratio, generally such that light backscattered from the samples couples preferentially to the detection path. As further illustrated in FIG. 4A, the beamsplitter 420 is also coupled to a wavelength or frequency sampled detection module 430 over a detection path 406 that may be provided by an optical fiber.

As further illustrated in FIG. 4A, the source 400 is coupled to the beamsplitter 420 by a source path 405. The source 400 may be, for example, a SLED or tunable source. The reference arm 410 is coupled to the beamsplitter 420 over a reference arm path 407. Similarly, the surgical microscope 453 is coupled to the beamsplitter 420 over the sample arm path 408. The source path 405, the reference arm path 407 and the sample arm path 408 may all be provided by optical fiber.

As further illustrated in FIG. 4A, the surgical microscope 453 includes two oculars (binocular view ports) 462 for the surgeon to view the sample 499. The surgical microscope 453 of FIG. 4A may, but need not, include a dichroic filter (not shown) and an optimized objective lens 459 in accordance with embodiments discussed herein. The dichroic, when used, allows the OCT to be folded into the path in a way to partially share the clear aperture occupied by the ocular paths. In some embodiments of the present invention, the OCT center channel occupies the center field of the main objective. The dichroic may also be used to couple additional accessory element.

In some embodiments of the present invention where the dichroic is not used, the OCT center channel occupies the center field of the main objective, and the ocular channels occupy a peripheral portion of the main objective aperture.

In embodiments of the present inventive concept illustrated in FIG. 4A, the OCT optics or a subset thereof 4445 are integrated into a center channel of the surgical microscope 453. The OCT sample arm 445 is positioned in the center channel of the surgical microscope 453. The objective lens 259 is positioned beneath the OCT portion 445.

Figure 4B:
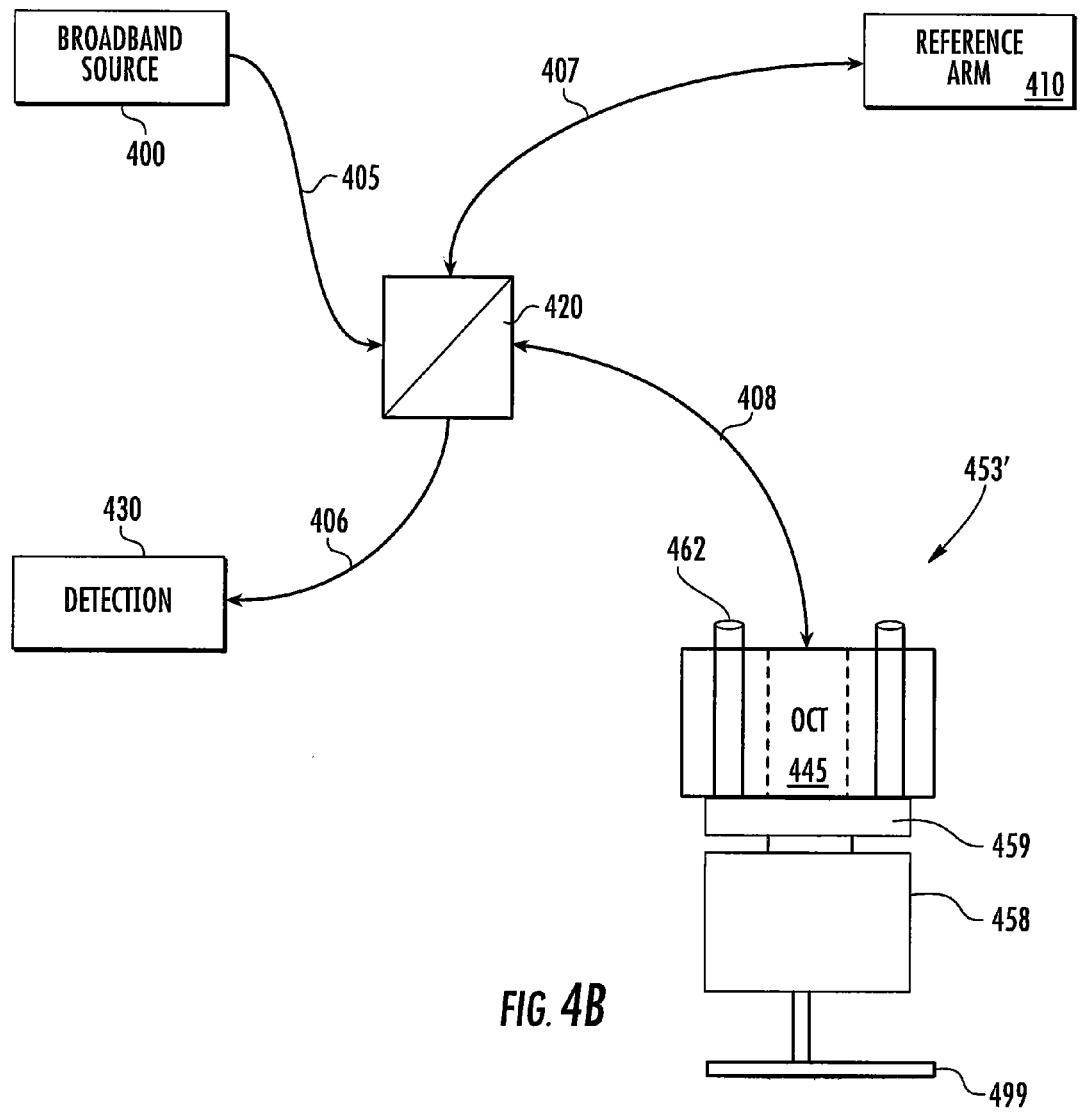
FIG. 4B is a block diagram of an OCT center channel surgical microscope in accordance with some embodiments of the present inventive concept.

Referring now to FIG. 4B, a block diagram of a center channel surgical microscope in accordance with some embodiments of the present inventive concept will be discussed. Like reference numbers in FIG. 4B refer to like elements in FIG. 4A, thus, details of these elements will not be repeated in the interest of brevity. As illustrated in FIG. 4B, a retinal lens 458 (surgical retina lens assembly) in accordance with some embodiments of the present inventive concept is positioned beneath the objective lens 459. The retinal lens 458 in accordance with embodiments discussed herein is optimized for use with OCT and is configured to adjust accordingly. As illustrated in FIG. 3 discussed above, the retina lens (surgical retina lens assembly) includes a condenser 340 and a retina lens 342 that may be modified to reduce the optical path length difference for the OCT scan beam across the field of view of the retina. Details with respect to the surgical retinal lens assembly having various FOVs will be discussed further below.

Figure 4C:
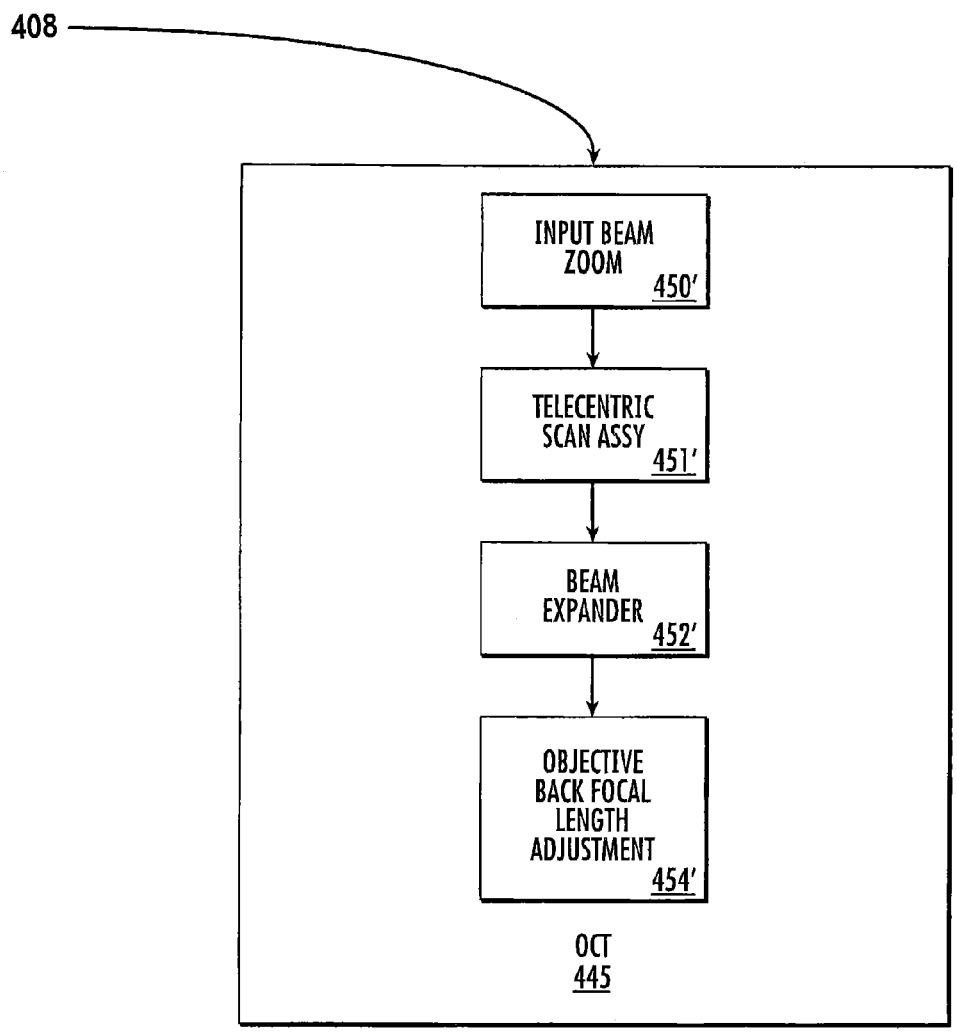
FIG. 4C is a detailed block diagram of the OCT portion of the OCT center channel surgical microscope illustrated in FIGS. 4A-4B.

Referring now to FIG. 4C, a detailed block diagram of the OCT portion of the center channel surgical microscope illustrated in FIGS. 4A-4B will be discussed. As illustrated in FIG. 4C, the OCT portion 445 includes the IBZ 450', the telecentric scan assembly 451', the beam expander 452' and an optional back focal length adjuster 454' as discussed above with respect to FIG. 2A. The beam travels through the objective lens 459, and any subsequent accessory lenses 458 to image the sample 499, which may be an eye in some embodiments.

Figure 5:
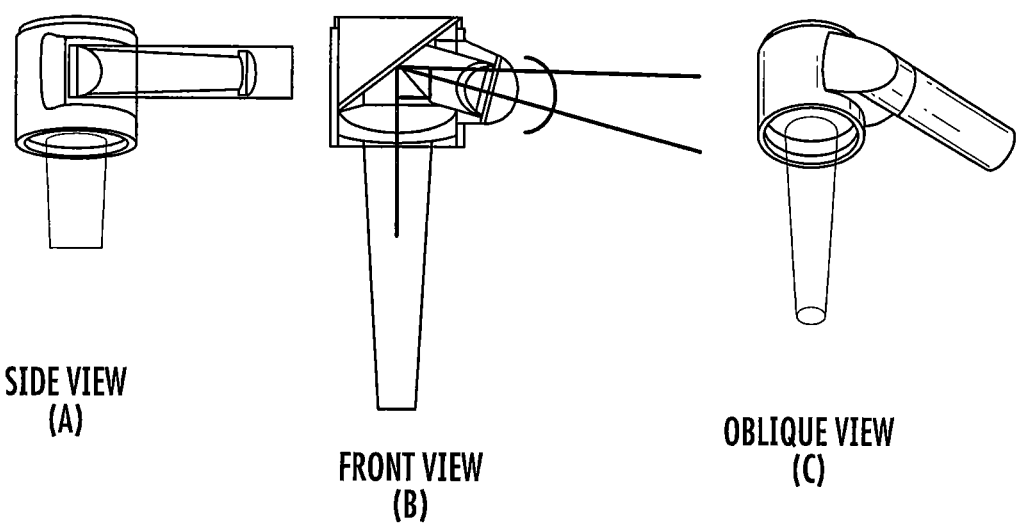
FIGS. 5A through 5C are a side view, front view and oblique view, respectively, of an OCT system interface in accordance with some embodiments of the present inventive concept.
Figure 6:
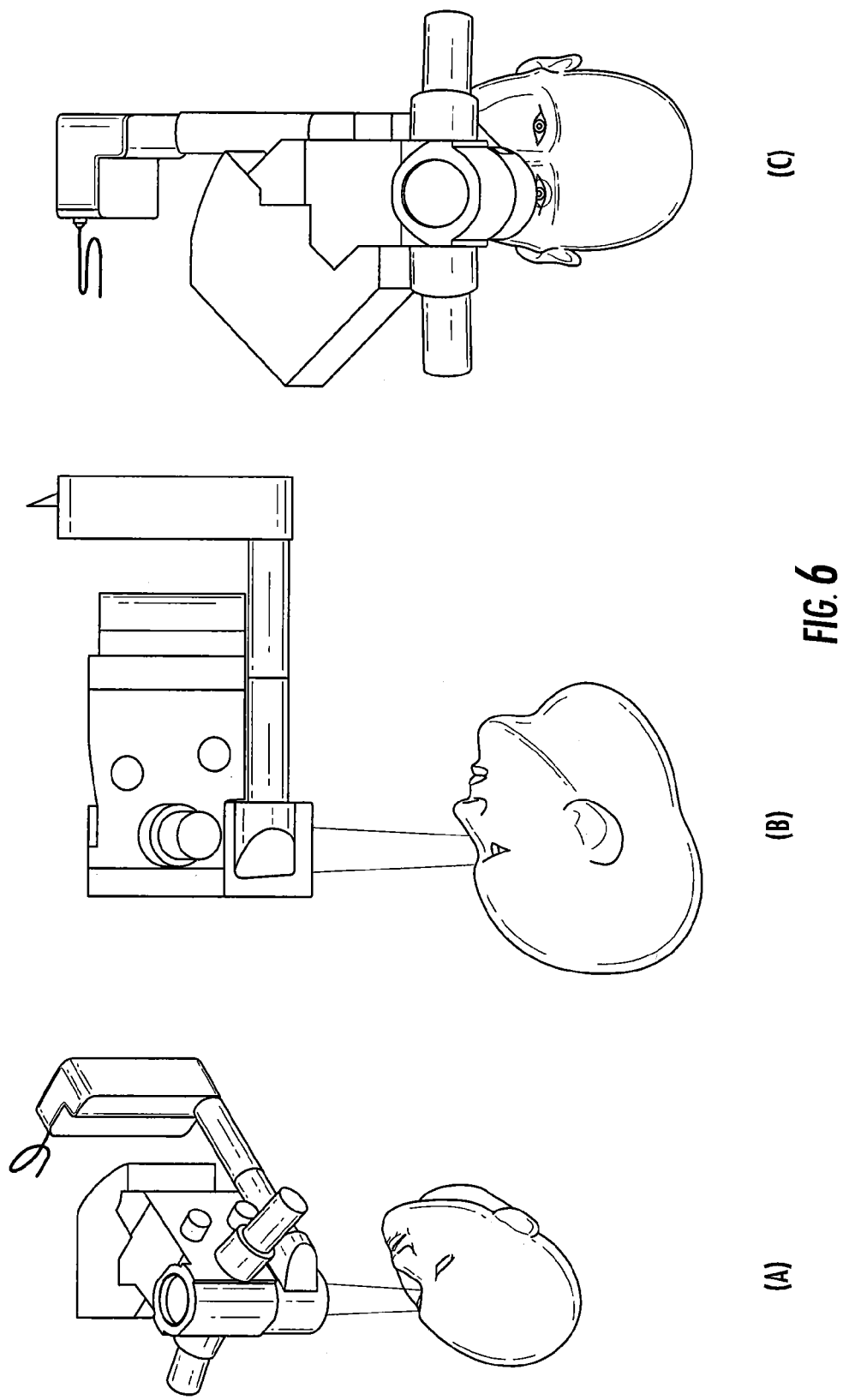
FIGS. 6A through 6C various views of an OCT system integrated with a surgical microscope in accordance with some embodiments of the present inventive concept.

Referring now to FIGS. 5A through 5C, a side view, front view and oblique view, respectively, of an OCT system interface in accordance with some embodiments of the present inventive concept are illustrated therein. In this representative embodiment, the OCT system is coupled into the "infinity space" of the microscope with the addition of a dichroic filter above the microscope main objective. In an embodiment of the present invention, the dichroic filter is situated at an angle greater than 45 degrees with respect to the microscope viewing path. In this situation, the angle of the OCT input with respect to the path between the objective lens and the sample is less than 90 degrees, as illustrated in FIG. 5 B. The vertical space occupied by the dichroic filter sets the minimum addition to the working distances for the surgeon. The minimum vertical space requirement is equal to the clear aperture of the main objective divided by the tangent of the angle of the dichroic. At 45 degrees, the minimum vertical space requirement is equal to the objective clear aperture, and the OCT beam enters the coupling space at 90 degrees. With the angle increased to 50 degrees, vertical space requirement is reduced to 84% of the objective clear aperture, and the OCT beam enters the coupling space an angle of 80 degrees with respect to the vertical axis, or 10 degrees with respect to the horizontal.

In the 45 degree dichroic configuration, with the OCT entering the imaging path at 90 degrees, the OCT beam diameter may be configured to fully illuminate the clear aperture of the main objective, as suggested by Izatt. This condition is not always desirable for optimum imaging performance, as will be illustrated in discussions below. It is important however to maintain an unvignetted OCT beam path. As the dichroic is tilted away from 45 degrees and the OCT beam enters the beam path from an angle at less than 90 degrees, the maximum aperture of the OCT beam is constrained. Through a geometric analysis, the maximum aperture of the OCT beam as a fraction of the main objective aperture can be described by Eqn. (1) below:

$$F=[1-2*T/(1+T)]$$

Where F equals the ratio of the maximum unvignetted OCT beam diameter to the clear aperture of the main objective, and T is a geometric function described in Eqn. (2) below:

$$T=\text{Tan}(2*\theta-\pi/2)*\text{Tan}(\theta)$$

Where θ is equal to the angle of the dichroic filter with respect to the optical axis of the main objective (such that 90 degrees is perpendicular to the optical axis).

In an embodiment of the present invention, the filter angle θ is greater than 45 degrees and less than 60 degrees. In another embodiment of the invention, the filter angle is greater than 48 degrees, such that there is at least a 10% reduction in the vertical space requirement for the OCT entry beam, and less than 55 degrees, such that the maximum unvignetted OCT beam diameter is at least 30% of the main objective clear aperture. In yet another embodiment of the invention, the filter angle is greater than 50 degrees, such that there is at least a 15% reduction in the vertical space requirement for the OCT entry beam, and less than 54 degrees, such that the maximum unvignetted OCT beam diameter is at least 40% of the main objective clear aperture. In still another embodiment of the invention, the filter angle is set at approximately 53 degrees, such that there is at approximately a 25% reduction in the vertical space requirement for the OCT entry beam, and such that the maximum unvignetted OCT beam diameter is approximately 45% of the main objective clear aperture.

Referring now to FIGS. 6A through 6C various views of an OCT system integrated with a surgical microscope in accordance with some embodiments of the present inventive concept are illustrated therein. In some embodiments, the surgical microscope may be a Leica M844 surgical microscope. However, embodiments of the present inventive concept are not limited to this configuration. Embodiments of the present inventive concept may be used with any surgical microscope without departing from the scope of the present inventive concept. FIG. 6A is a plan view of the OCT system integrated with a surgical microscope in accordance with some embodiments discussed herein. FIGS. 6B and 6C are side and top views, respectively.

Figure 7A:
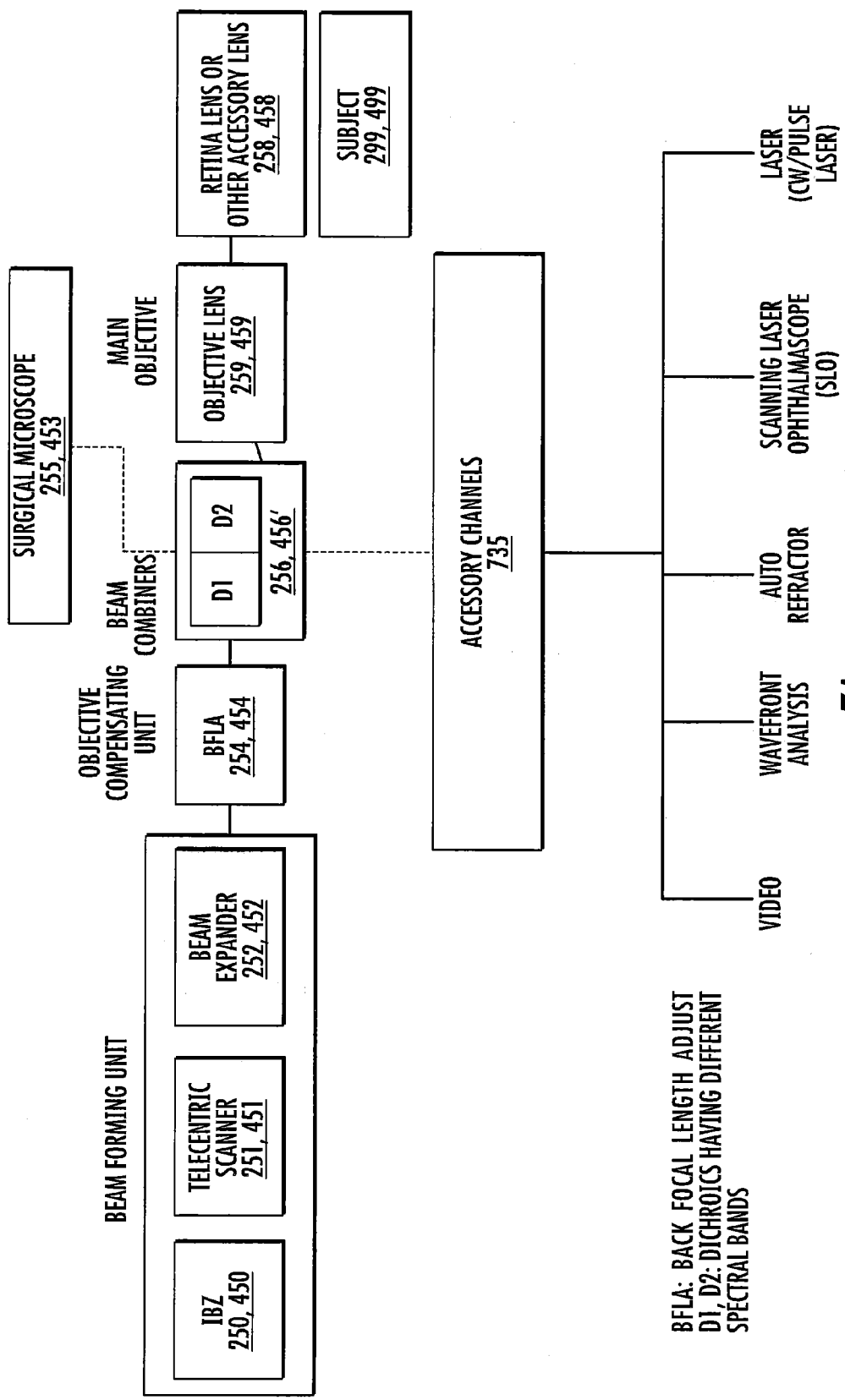
FIG. 7A is a block diagram illustrating a block diagram of an OCT-Integrated Surgical Microscope in accordance with some embodiments of the present inventive concept

Referring now to FIG. 7A, a block diagram of an OCT-Integrated Surgical Microscope in accordance with some embodiments of the present inventive concept will be discussed. As illustrated in FIG. 7A, the OCT integrated surgical microscope system includes a surgical microscope 255, 453, a beam forming unit, an objective compensating unit, beam combiners, a main objective, a retina lens 258, 458 or other accessory lens, a subject 299, 499 and accessory channels 735 as discussed above with respect to FIG. 2A.

As further illustrated in FIG. 7A, the beam forming unit includes the IBZ 250, 450, the telecentric scanner 251, 451 and the beam expander 252, 452. The objective compensating unit includes the back focal length adjust (BFLA) 254, 454. The beam combiners include one or more dichroic filters 256, 456 having different spectral bands (e.g. D1, D2). The main objective includes an objective lens 259, 459 that may be modified in accordance with embodiments discussed herein. As further illustrated, accessory channels may be provided in the "infinity space" Or elsewhere in the OCT imaging path. These Accessories may include, but are not limited to, for example, a video camera, a wavefront analysis system, an auto refractor, a scanning laser ophthalmoscope (SLO) and/or a laser, for example, a CW/Pulse Laser.

Figure 7B:
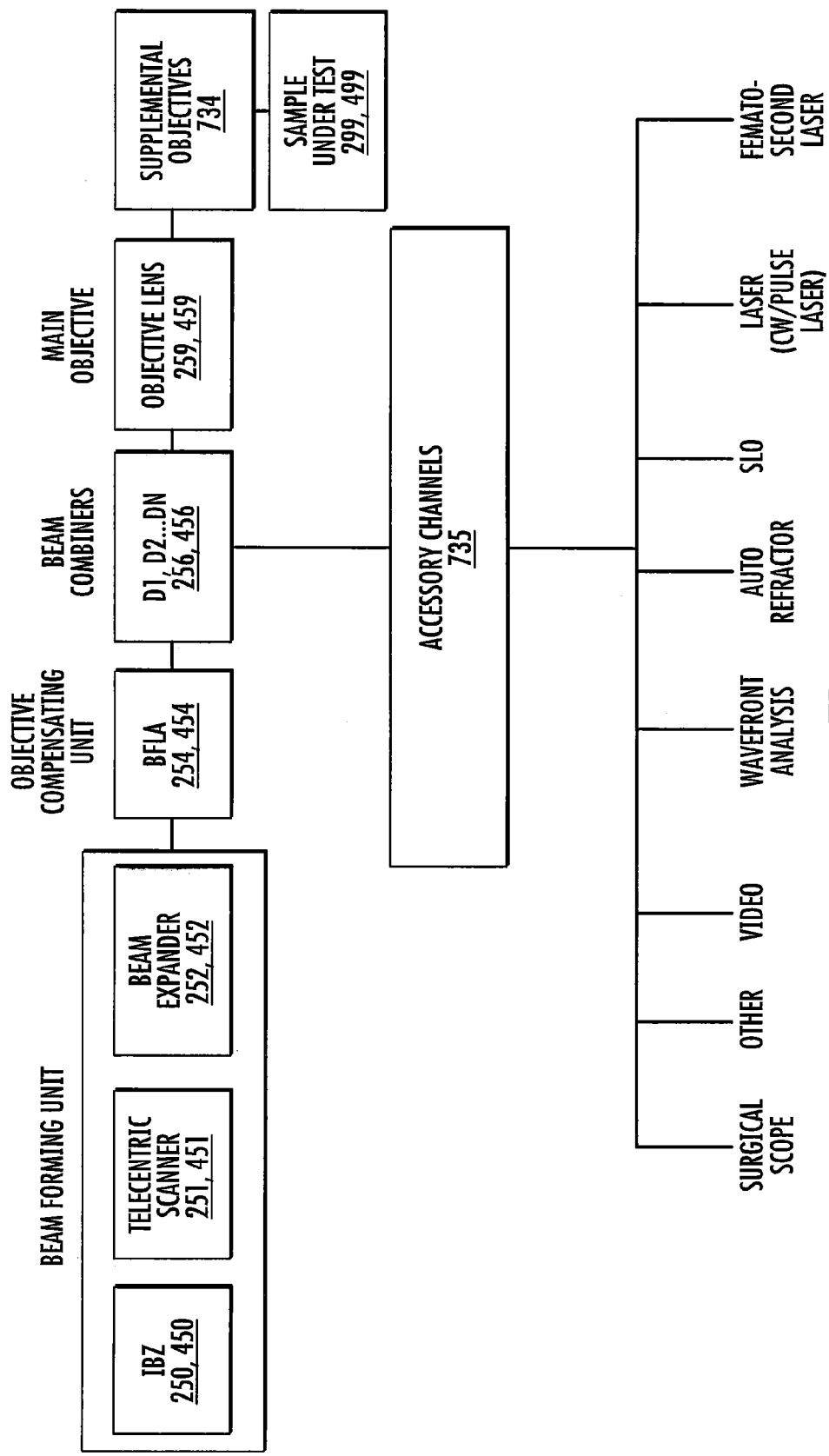
FIG. 7B is a block diagram illustrating a block diagram of an OCT system including an Integrated Surgical Microscope in accordance with some embodiments of the present inventive concept.

Referring now to FIG. 7B, a block diagram illustrating an OCT-Integrated Surgical Microscope in accordance with some embodiments of the present inventive concept will be discussed. As illustrated in FIG. 7A, the OCT integrated surgical microscope system includes a beam forming unit, an objective compensating unit, beam combiners, a main objective, supplemental objectives 734, a sample under test 299, 499 and accessory channels 735. In this diagram, the OCT system is viewed as a primary imaging system, and the surgical microscope is one of a possible plurality of combined modalities.

As further illustrated in FIG. 7B, the beam forming unit includes the IBZ 250, 450, the telecentric scanner 251, 451 and the beam expander 252, 452. The objective compensating unit includes the back focal length adjust (BFLA) 254, 454. The beam combiners include dichroic filters 259, 459 having different spectral bands (D1, D2 . . . DN). The main objective includes an objective lens 259, 459 that may be modified in accordance with embodiments discussed herein. Accessories may include, but are not limited to, for example, a surgical scope, a video camera, a wavefront analysis system, an auto refractor, a scanning laser ophthalmoscope (SLO), a laser, for example, a CW/Pulse Laser, a femto second laser and/or other accessory.

Figure 7C:
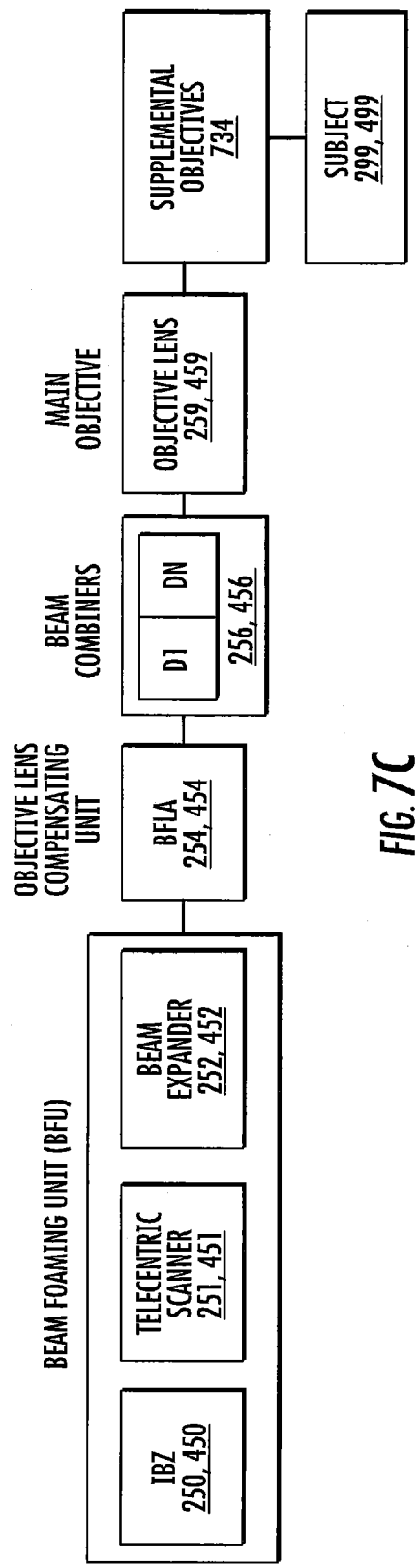
FIG. 7C is a block diagram illustrating an OCT system suitable for integrating with Surgical Microscope in accordance with some embodiments of the present inventive concept.

Referring now to FIG. 7C, a block diagram illustrating a generalized construction of an OCT-Integrated Surgical Microscope in accordance with some embodiments of the present inventive concept will be discussed. As illustrated in FIG. 7C, the OCT integrated surgical microscope system includes a beam forming unit, an objective compensating unit, beam combiners, a main objective, supplemental objectives 734 and a subject 299, 499.

As further illustrated in FIG. 7C, the beam forming unit includes the IBZ 250, 450, the telecentric scanner 251, 451 and the beam expander 252, 452. The objective compensating unit includes the back focal length adjust (BFLA) 254, 454. The beam combiners include dichroic filters 259, 459 having different spectral bands (D1, D2). The main objective includes a modified objective lens 259, 459 in accordance with embodiments discussed herein. Optional accessories may be coupled through the beam combiners which may be wavelength dependent (dichroic) or polarization dependent.

Figure 8:
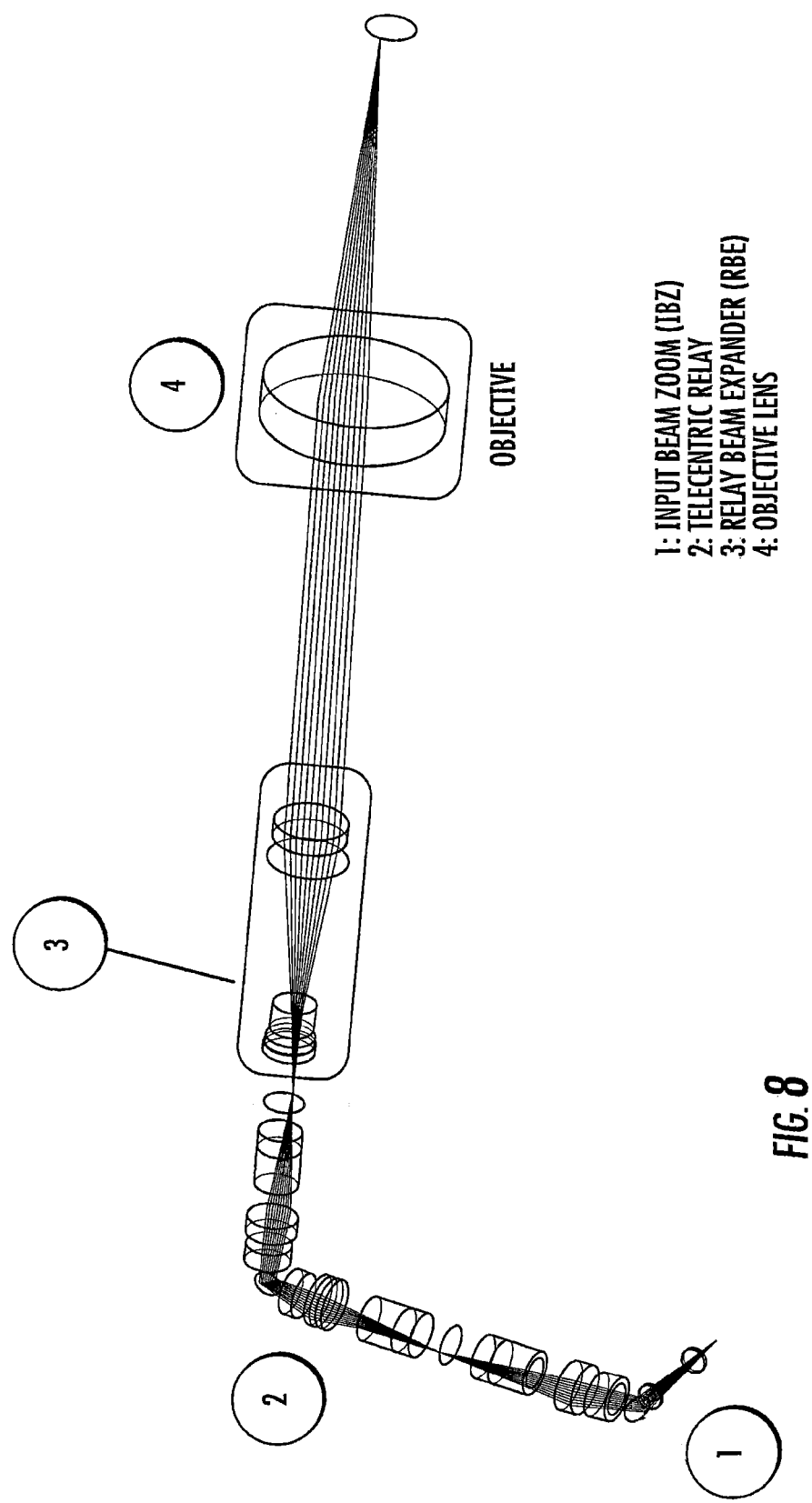
FIG. 8 is a diagram illustrating an OCT optical path for surgical imaging in accordance with embodiments of the present inventive concept.

Referring now to FIG. 8, a diagram illustrating an OCT optical path for surgical imaging in accordance with some embodiments of the present inventive concept will be discussed. As illustrated therein, the portion if the optical path labeled (1) represents the IBZ; the portion of the optical path labeled (2) represents the telecentric relay; the portion of the optical path labeled (3) represents the RBE; and the portion of the optical path labeled (4) represents the objective lens in accordance with embodiments of the present inventive concept.

Figure 9A:
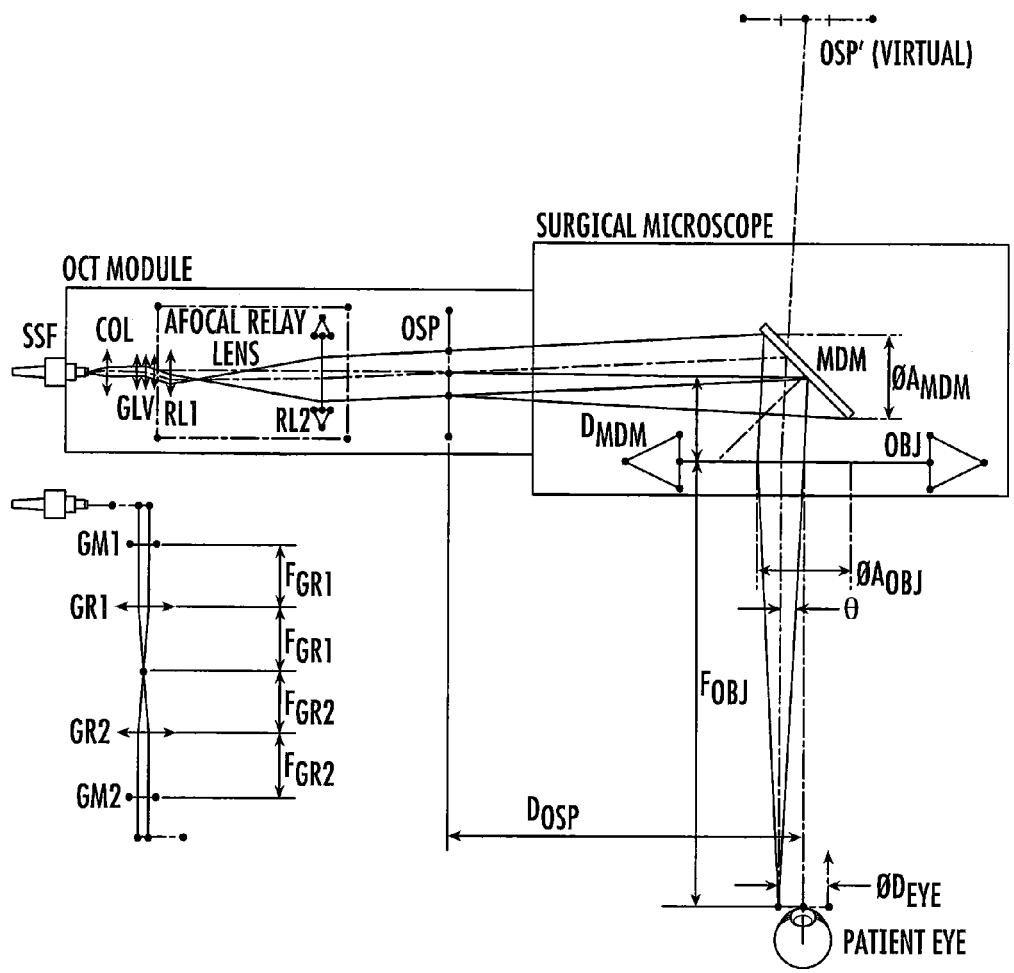
FIG. 9A is a schematic diagram illustrating a layout of an OCT system integrated into the path of a Surgical Microscope in accordance with some embodiment of the present inventive concept.
Figure 9B:
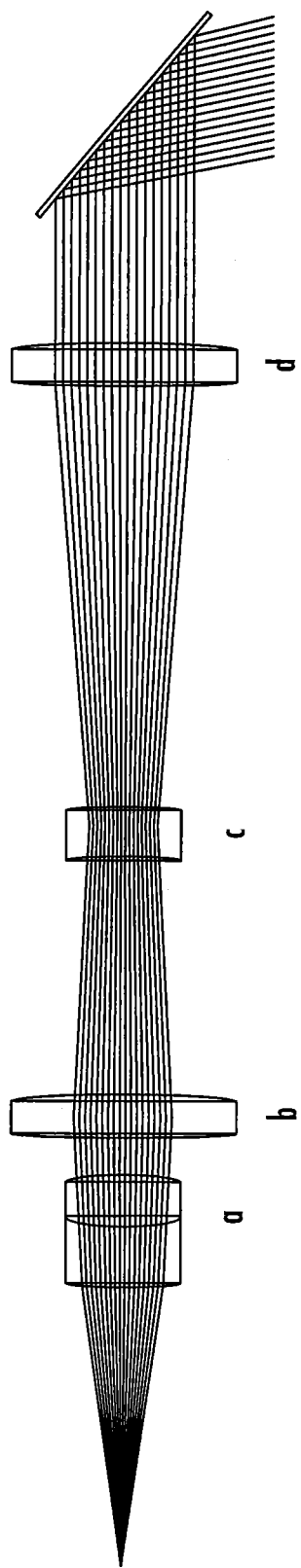
FIG. 9B is a diagram illustrating a collimator and Input Beam Zoom (IBZ) system in accordance with some embodiments of the present inventive concept.

FIG. 9A is a schematic diagram illustrating another layout of an IO-OCT system in accordance with some embodiment of the present inventive concept. FIG. 9A illustrates a system layout including components used and a representation of first-order (thin lens) parameters. The input collimator assembly (CQL) includes the Input Beam Zoom, and is followed by the telecentric relay from galvo mirror 1 (GM1) to galvo mirror 2 (GM2), and then expended by the afocal relay from relay lens 1 (RL1) through relay lens 2 (RL2). First-order equations relating all the system optical parameters were derived for two extreme limiting cases of numerical aperture that bracketed the performance space: a high NA (HNA) case with high lateral resolution and low DOF; and a low NA (LNA) case with low lateral resolution and high DOF. These equations were used to calculate an estimated overall system length from input fiber source to eye. The design space was mapped out for various driving parameters, such as input beam diameter and working distance, and a solution that provides a reduced overall system length was chosen for this embodiment.

With this chosen first-order system design, various methods of NA and focal plane control were evaluated. It was determined that an IBZ system between the collimated input beam and the first scanning galvo mirror could provide the required control over NA and, thus, lateral resolution and DOF, and focal plane location. A second-order (thick lens) design was generated for the IBZ system. In some embodiments, this zoom system consists of 3 singlets as illustrated, for example, in FIG. 9B, one negative lens element (c) and two identical positive elements (b) and (d).

In operation, the first positive element (b) stays fixed, while the negative (c) and last positive (d) element positions are modified to set a continuous range of focal and numerical aperture conditions. A forward motion of the negative element (c), accompanied with a shorter retrograde motion of the last positive element (d) allows the IBZ system to go from a HNA to LNA configuration, and can be coordinated to do so at constant focal position. Motion of the last positive element (d) adjusts the system focal plane location: backward motion moves the focal plane forward with respect to the subject (i.e. deeper into the eye). In these embodiments, all the variation can be accomplished with two lens element motions. Furthermore, this zoom system may be located prior to the scanning optical system allowing for modular system design and decreased system complexity.

Referring again to FIG. 8, with the IBZ specified, a second-order (thick lens) design was generated for the remainder of the system illustrated in FIG. 8. The primary sub-systems following the IBZ are, in transmitted light incidence order: the first scanning galvo mirror (X); the galvo relay lens (GRL) system; the second, orthogonal scanning galvo mirror (Y); and the afocal relay beam expander (RBE) system. The GRL defines the optical system pupil, locates it at the first (X) galvo mirror, and images it to the second (Y) galvo mirror. The RBE system then images this system pupil with the required magnification to the back focal plane of the surgical microscope objective lens. This last condition, in combination with the relay of the X galvo to the Y galvo, is a necessary condition allowing the system to be telecentric in the focal plane of the microscope objective. This condition may lead to a long optical path length for the OCT scanning system. A further optional feature of the inventive design is to design the optics such that the system pupil is virtual, allowing the location of the system pupil to overlap preceding lens elements, thereby reducing the overall system length and the optical path length of the system while maintaining system telecentricity.

As discussed above, FIG. 9B is a diagram illustrating a collimator (a) and Input Beam Zoom (IBZ) (b, c, and d) system in accordance with some embodiments of the present inventive concept.

Figure 9C:
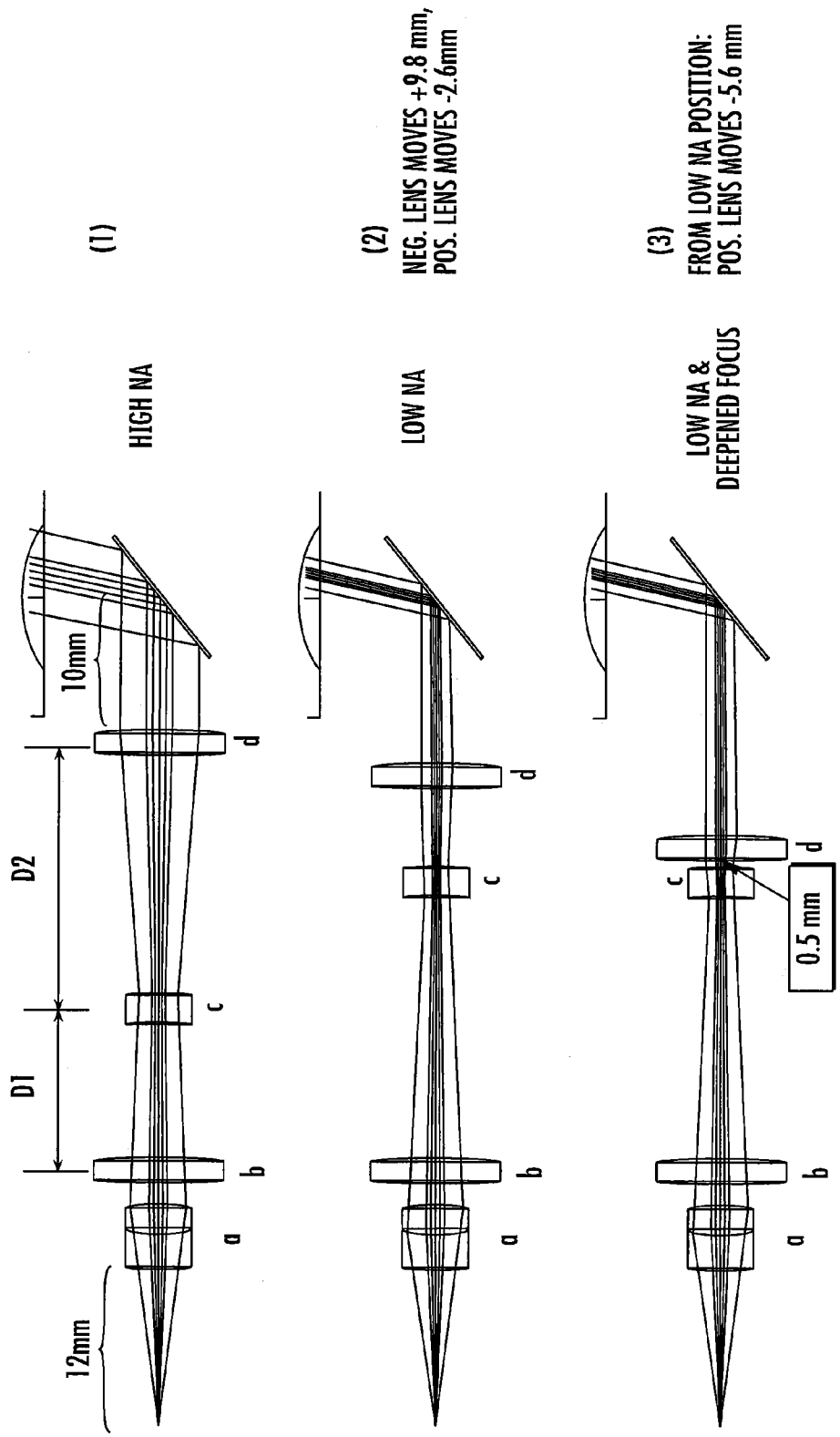
FIG. 9C is a diagram illustrating changing numerical aperture (NA) and switching regions of focus with the IBZ in accordance with some embodiments of the present inventive concept.

Referring now to FIG. 9C, a diagram illustrating changing numerical aperture (NA) and switching regions of interest with the IBZ in accordance with some embodiments of the present inventive concept will be discussed. As illustrated the collimator lens (a) is followed by the IBZ including (b) a first positive lens, (c) a first negative lens and (d) a second positive lens.

As used herein, the "input beam zoom" refers to the zoom factor as a function of first and second lens spacing, D1 and D2 illustrated in FIG. 9C. The zoom factor controls the numerical aperture (NA). For example, at zoom factor=1, the system is in low NA mode. As zoom factor increases, the NA of the system increases. As discussed above, the first lens spacing (D1) is the distance to the negative lens (c) from the first positive lens (b) and the second lens spacing (D2) is the distance to the final positive lens (d) from the negative lens (c).

At any zoom setting, focus may be adjusted by movement of the final lens (c) of the IBZ. Increasing the second lens spacing (D2) increases the focal power of the IBZ, and shortens the focal length of the system. Reducing the second lens spacing (D2) reduces the focal power of the IBZ and increases the focal length of the system. It will be noted that two degrees of freedom, lens spacing D1 and lens spacing D2, provide a continuous range of control of system numerical aperture and focus. The range of control is dependent on the available physical space for movement of the lenses, the respective powers of the lenses, and the downstream imaging optics, as will be understood by one skilled in the art. It will also be noted that the imaging conditions are deterministic, and multiple modes of control may be employed to achieve a desired state, including without limitation, sequential or simultaneous movement of lens, movement according to values set in a lookup table, or adjustment with feedback based on positional encoders or in response to image quality feedback.

Thus, in case (1) illustrated in FIG. 9C, the spacings D1, D2 result in high numerical aperture (NA) (e.g. the maximum NA for the specific configuration). In case (2), the negative lens (c) moves +9.8 mm and the positive lens (d) moves −2.6 mm to result in low NA. In case (3), from the low NA position of case (2), the positive lens (d) moves −5.6 mm to result in low NA and deepened focus.

Figure 10:
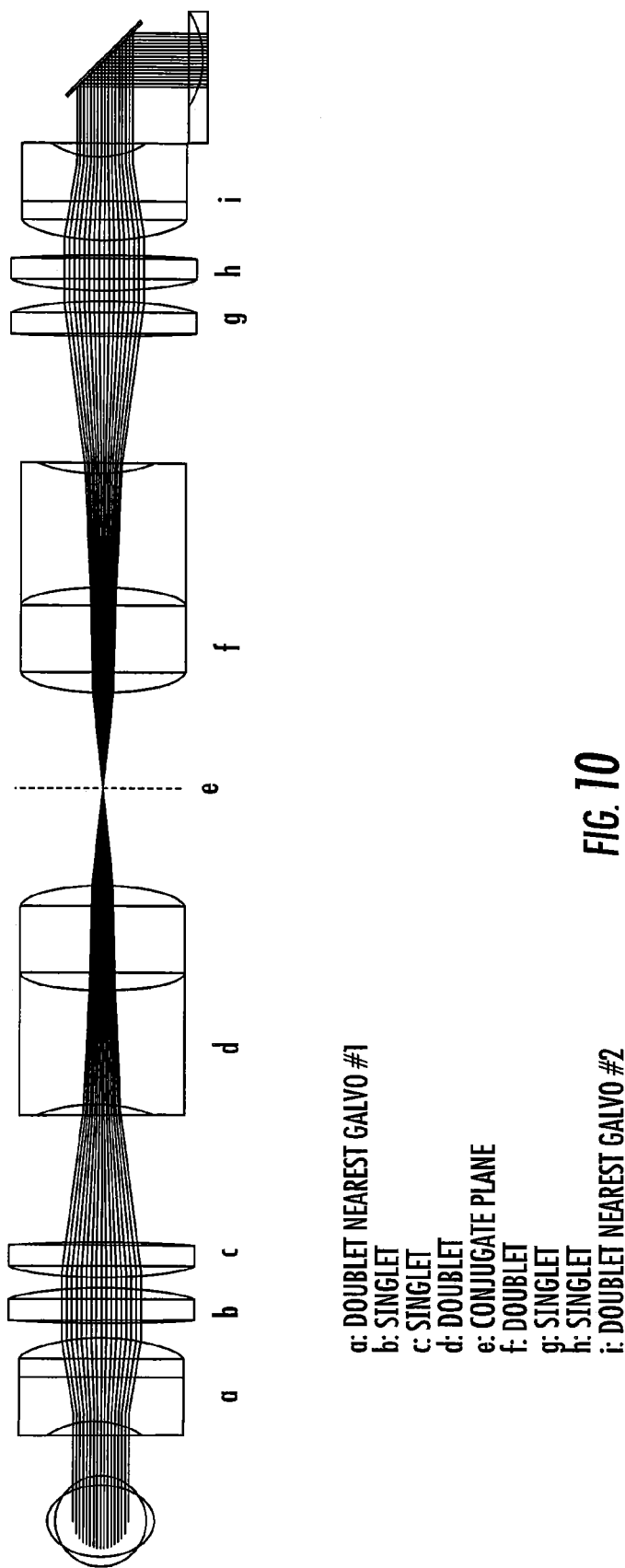
FIG. 10 is a block diagram illustrating a telecentric relay system in accordance with some embodiments of the present inventive concept.

Referring now to FIG. 10, a block diagram illustrating a telecentric relay system in accordance with some embodiments of the present inventive concept will be discussed. As illustrated therein, the telecentric relay system, for example, elements 251 and 451 discussed above, may include (a) a Doublet nearest Galvo #1 (X); (b) a Singlet; (c) a Singlet; (d) a Doublet; (e) a Conjugate Plane; (f) a Doublet; (g) a Singlet; (h) a Singlet; and (i) a Doublet nearest Galvo #2 (Y). As is clear from the block diagrams discussed above, the telecentric relay system 251, 451 follows the IBZ 250, 450.

Figure 11:
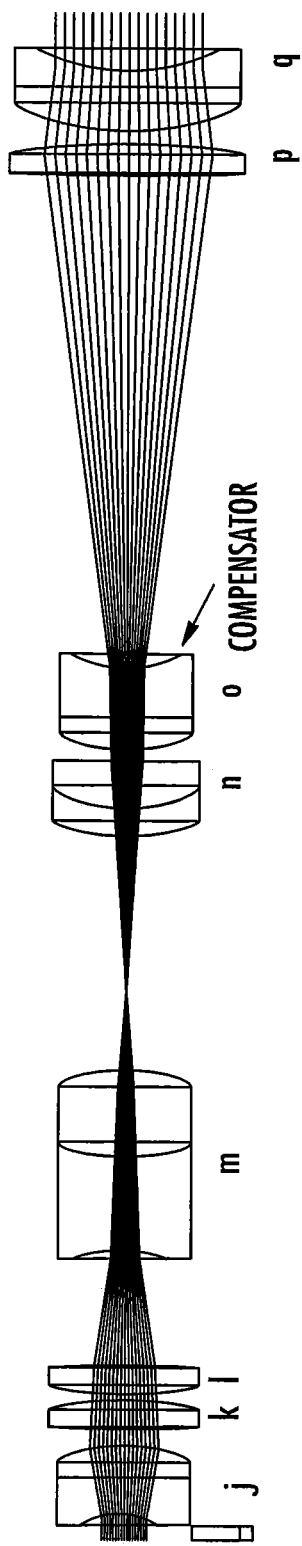
FIG. 11 is a diagram illustrating a relay beam expander (RBE) system in accordance with some embodiments of the present inventive concept.

Referring now to FIG. 11, a diagram illustrating a relay beam expander (RBE) system in accordance with some embodiments of the present inventive concept will be discussed. As illustrated the RBE system, for example, elements 252, 452 discussed above, may include (j) a Beam expander input Doublet nearest Galvo #2 (Y); (k) a Singlet; (l) a Singlet; (m) a Doublet; (n) a Doublet; (o) an aberration correcting Compensating Singlet; (p) a Singlet; and (q) and a Beam expander output Doublet, nearest the microscope main objective. The compensating singlet (o) is designed to correct for essential aberrations that are known to arise from imaging with a basic achromatic doublet that comprises the microscope objective. As is clear from the block diagram discussed above, the telecentric relay system (251, 451) discussed with respect to FIG. 10 is coupled to the RBE system 252, 452 discussed with respect to FIG. 11 and both proceed the objective lens as discussed above.

Figure 12:
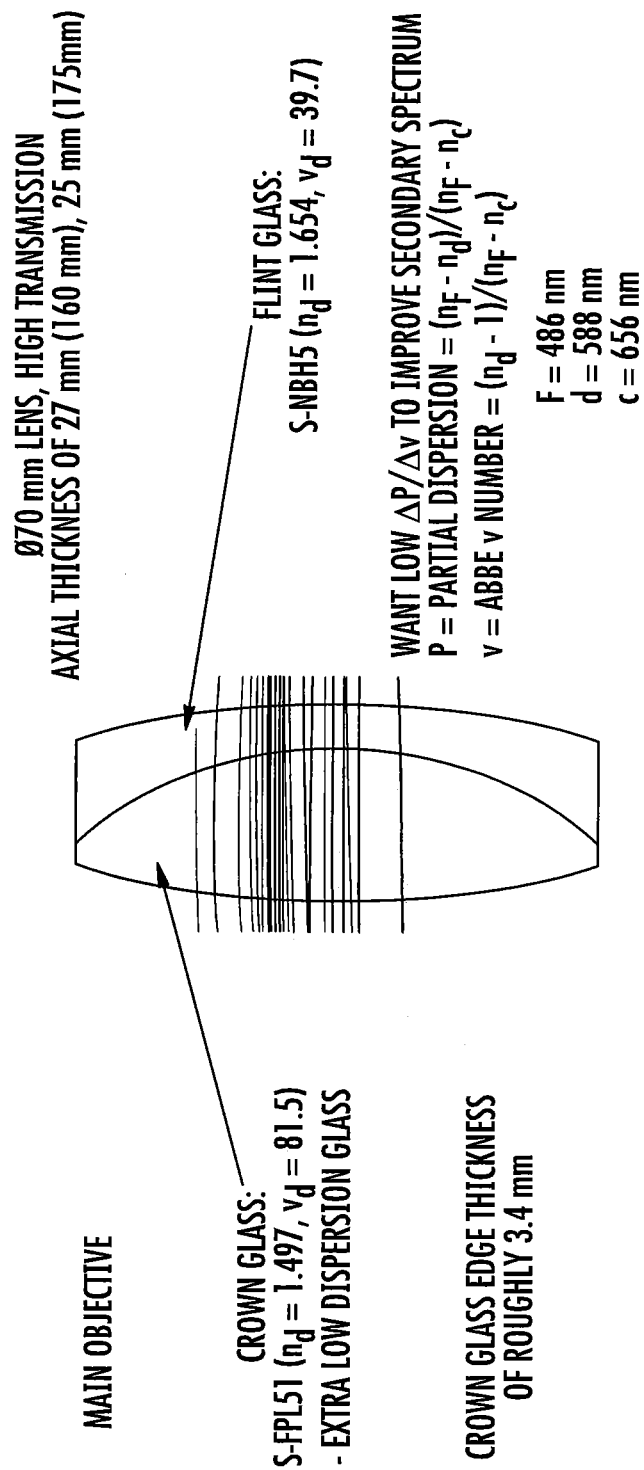
FIG. 12 is a diagram illustrating a high performance objective lens for an OCT surgical microscope in accordance with some embodiments of the present inventive concept.

Referring now to FIG. 12, a diagram illustrating a high performance objective lens for an OCT surgical microscope in accordance with some embodiments of the present inventive concept. As illustrated in FIG. 12, the objective lens may include crown glass and flint glass. The crown glass may have an edge thickness of about 3.4 mm. The objective lens illustrated in FIG. 12 is a 70 mm high transmission lens having an axial thickness of about 27 mm (160 mm), 25 mm (175 mm) This objective is thinner than a standard commercial microscope objective, has better imaging optical properties through a low fractional partial dispersion, improving the bandwidth of the objective to incorporate the visible spectrum for the microscope and the near infrared imaging for the OCT.

In some embodiments, the Crown Glass S-FPL51 ($n_d$=1.497, $v_d$=81.5) (Extra low dispersion glass) and the Flint Glass S-NBH5 ($n_d$=1.654, $v_d$=39.7). In these embodiments, a low $\Delta P/\Delta v$ is wanted to improve a secondary spectrum, where P=partial dispersion=$(n_F-n_d)/(n_F-n_C)$ and $v$=Abbe $v$ number=$(n_d-1)/(n_F-n_C)$. In some embodiments, F=486 nm, d=588 nm and C=656 nm.

In an embodiment of the present invention, the microscope objective is anti-reflection coated for operation in the visible and infrared spectrums relevant to the microscope and the OCT system, respectively.

Figure 13:
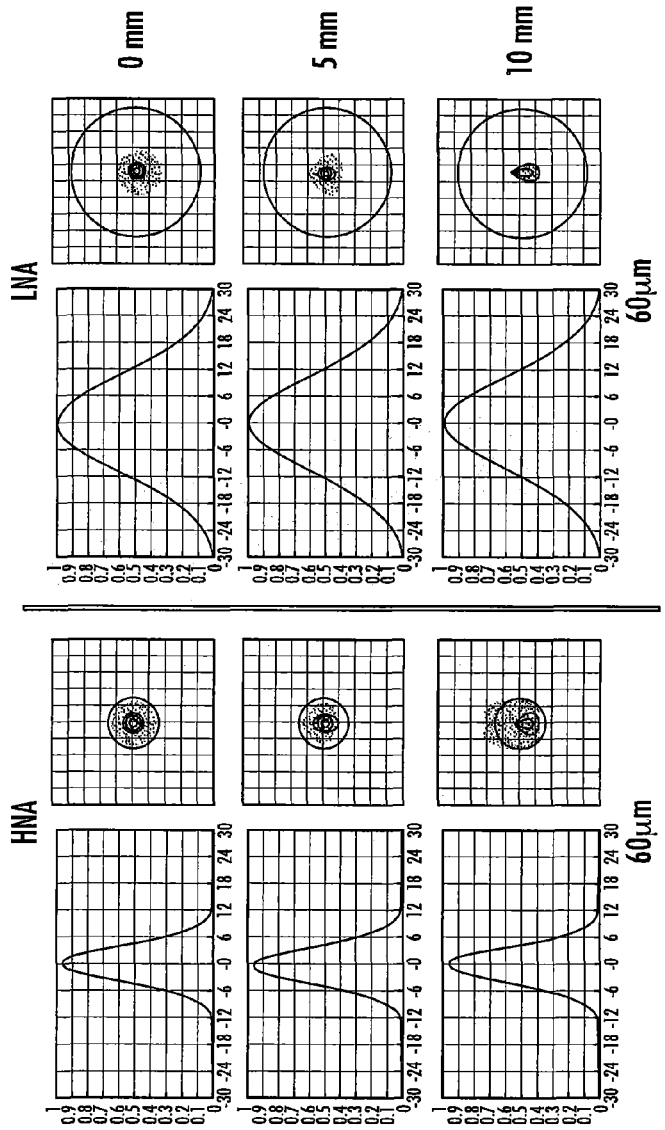
FIG. 13 is a series of graphs and charts illustrating telecentric optical performance in accordance with some embodiments of the present inventive concept.

FIG. 13 is a series of graphs and charts illustrating telecentric optical performance of a 150 mm objective lens at nominal focus in accordance with some embodiments of the present inventive concept. A 150 mm objective lens represents a relatively short focal length objective that might be used in an ocular surgical procedure. In FIG. 13, the OCT spot size at the telecentric focal plane is shown across the 10 mm half-field of view, in the limits of high numerical aperture (HNA) as set by the IBZ, and low numerical aperture (LNA). The spot diameters range from 10 um (HNA) to 25 um (LNA), constant across the field of view. Telecentricity is quantified as both field flatness, or optical path length difference (OPLD) for the scanned OCT beam, and maximum angle of incidence deviation from perpendicular for rays incidence on the focal plane. The maximum OPLD is 1.7 µm, or 0.017% of the field of view, and the deviation from perpendicularity is 0.067 degrees.

Figure 14:
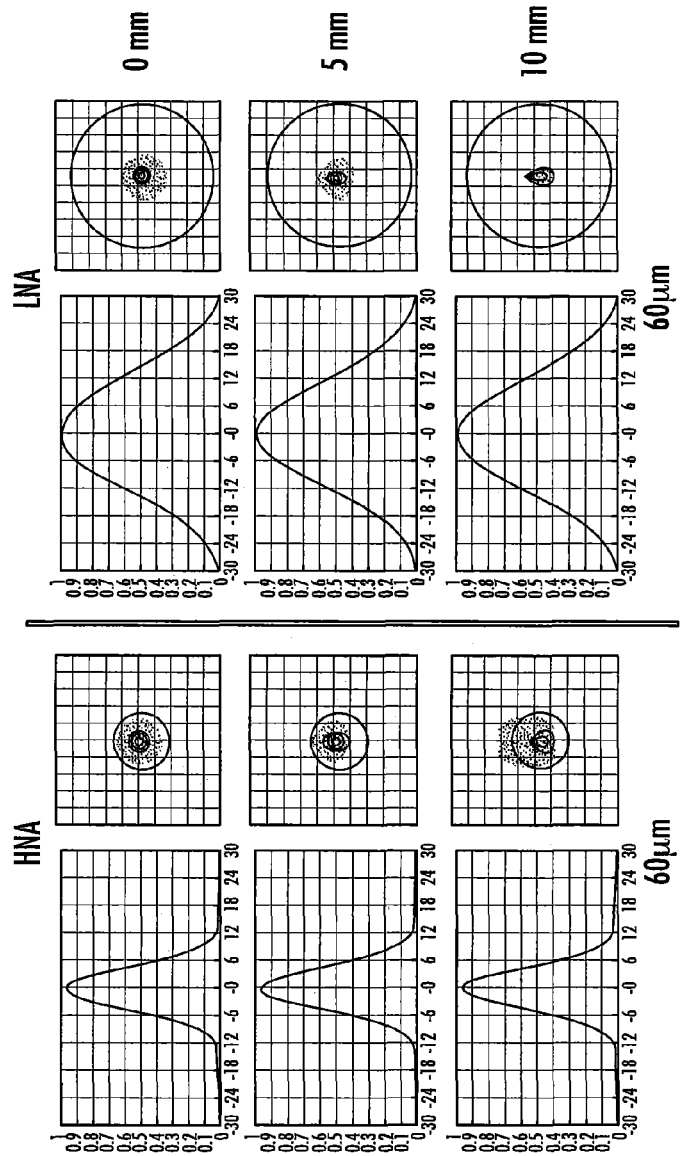
FIG. 14 is a series of graphs and charts illustrating telecentric optical performance in accordance with some embodiments of the present inventive concept.

FIG. 14 is a series of graphs and charts illustrating telecentric optical performance of a 175 mm objective lens at nominal focus in accordance with some embodiments of the present inventive concept. A 175 mm objective lens represents a typical objective that might be used in an ocular surgical procedure. In FIG. 14, the OCT spot size at the telecentric focal plane is shown across the 10 mm half-field of view, in the limits of high numerical aperture (HNA) as set by the IBZ, and low numerical aperture (LNA). The spot diameters range from 11 um (HNA) to 27 um (LNA), constant across the field of view. The maximum OPLD is 1.7 µm, or 0.017% of the field of view, and the deviation from perpendicularity is 0.061 degrees.

FIG. 14 is a series of graphs and charts illustrating telecentric optical performance of a 175 mm objective lens at nominal focus in accordance with some embodiments of the present inventive concept. A 175 mm objective lens represents a typical objective that might be used in an ocular surgical procedure. In FIG. 14, the OCT spot size at the telecentric focal plane is shown across the 10 mm half-field of view, in the limits of high numerical aperture (HNA) as set by the IBZ, and low numerical aperture (LNA). The spot diameters range from 11 um (HNA) to 27 um (LNA), constant across the field of view. The maximum OPLD is 1.7 um, or 0.017% of the field of view, and the deviation from perpendicularity is 0.061 degrees.

Figure 15:
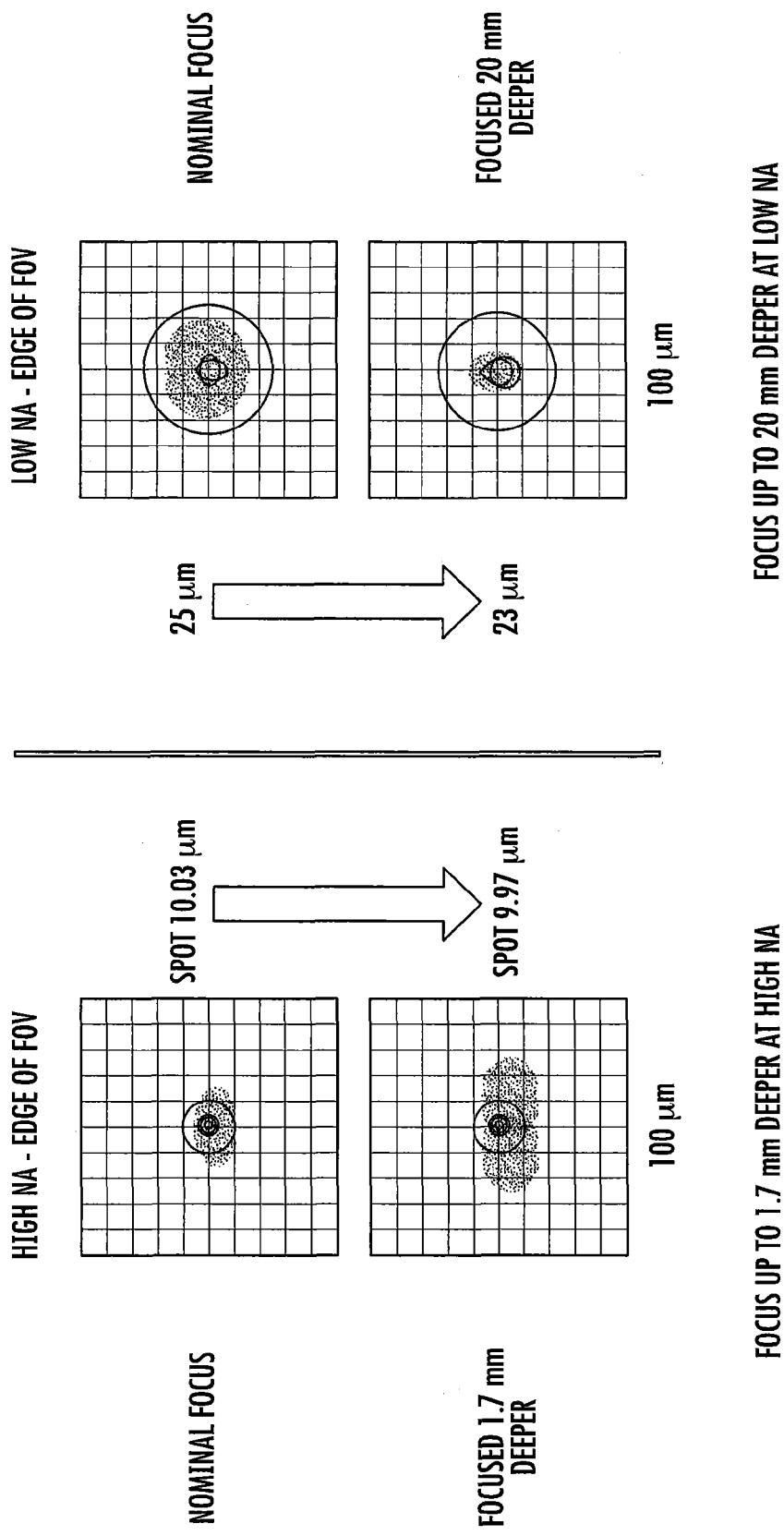
FIG. 15 is a series of graphs illustrating the optical performance when shifting focus with a 150 mm objective lens in accordance with some embodiments of the present inventive concept.

FIG. 15 is a series of graphs and charts illustrating optical performance of a 150 mm objective lens while shifting the OCT focus in accordance with some embodiments of the present inventive concept, demonstrating an ability to shift focus 1.7 mm deeper at constant spot size for the HNA case, and 20 mm deeper at LNA. Similar performance is achieved in focusing shallower, though not shown in the figure.

Figure 16:
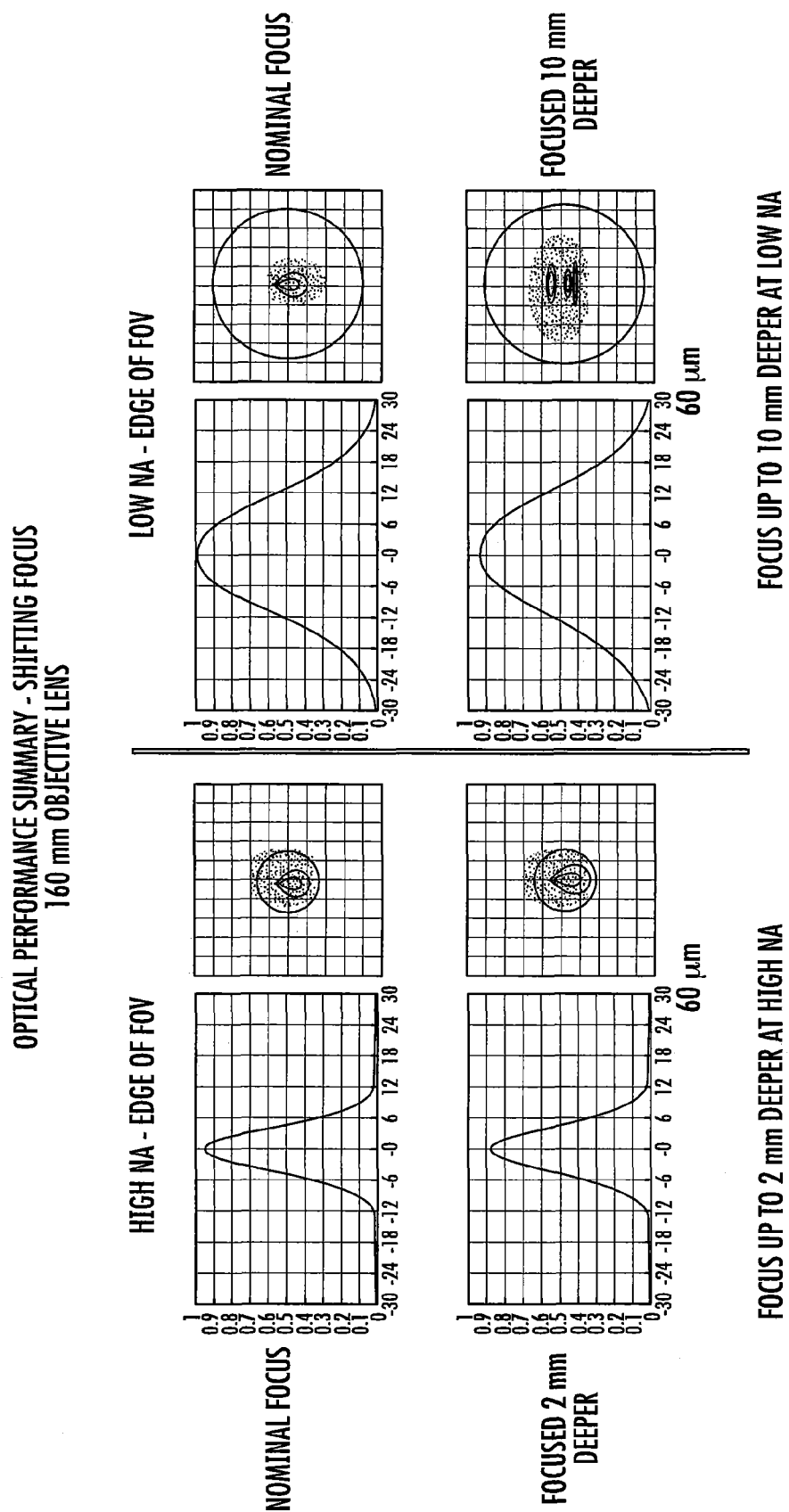
FIG. 16 is a series of graphs illustrating the optical performance when shifting focus with a 160 mm objective lens in accordance with some embodiments of the present inventive concept.

FIG. 16 is a series of graphs and charts illustrating exemplary optical performance of a 160 mm objective lens while shifting the OCT focus in accordance with some embodiments of the present inventive concept, demonstrating an ability to shift focus at least 2 mm deeper at constant spot size for the HNA case, and at least 10 mm deeper at LNA. Similar performance is achieved in focusing shallower, though not shown in the figure.

Figure 17:
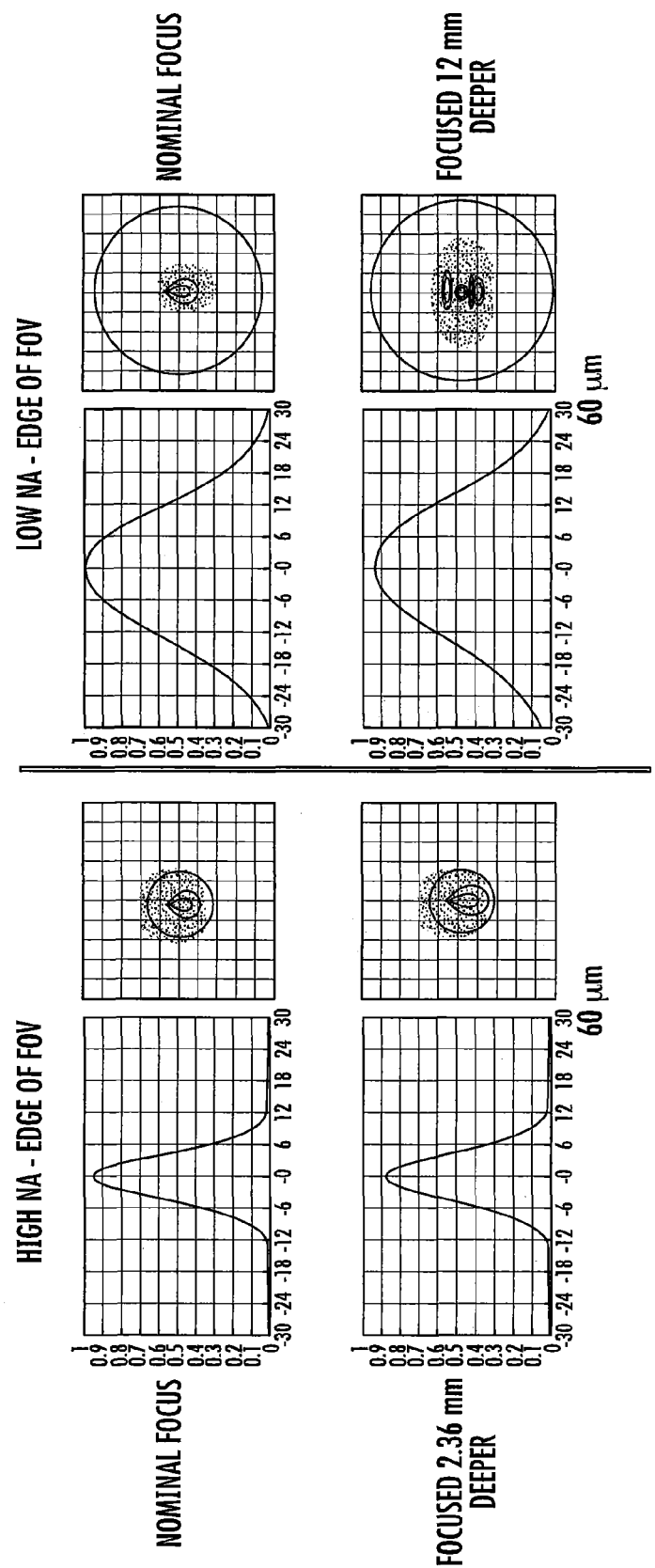
FIG. 17 is a series of graphs illustrating the optical performance when shifting focus with a 175 mm objective lens in accordance with some embodiments of the present inventive concept.

FIG. 17 is a series of graphs and charts illustrating exemplary optical performance of a 1675 mm objective lens while shifting the OCT focus in accordance with some embodiments of the present inventive concept, demonstrating an ability to shift focus at least 2.4 mm deeper at constant spot size for the HNA case, and at least 12 mm deeper at LNA. Similar performance is achieved in focusing shallower, though not shown in the figure.

FIGS. 18A and 18B are block diagrams illustrating conventional configurations for an accessory surgical retina imaging lens assembly and a configuration in accordance with embodiments of the present inventive concept, respectively. As illustrated in FIG. 18A, using a conventional objective lens, a conventional reduction lens and a conventional retina lens (e.g. BIOM), the pivot point of the OCT scan in the eye is imaged into the pupil plane of an eye. This is a typical position for OCT imaging, and is particularly well suited to nonvignetted OCT imaging of a non-mydriatic (non-dilated) eye. However, the pupil plane in a human eye is not at the center of curvature of the retina of the eye. The optical path length from pupil center to the periphery of the retina is generally significantly short than the optical path length to the center, or macular region of the retina. Having a pivot point in the pupil plane will cause the scan to scan around the pupil, which will cause the OCT image to look highly curved as shown in FIG. 18A. As illustrated therein, the OPLD (Optical path length distortion)=OPLc (optical path length to the center of the retina)−OPLe (optical path length to the edge of the retina), which will typically be in the range of about 3 mm-4 mm in an adult eye.

In stark contrast, using an optimized objective lens 259, 459 and modified retinal lens system 258, 458 in accordance with embodiments of the present inventive concept, the pivot of the scanning OCT beam is shifted towards the center of curvature of the retina as shown in FIG. 18B. Moving the pivot point further back in the eye provides a much flatter OCT image. Thus, as illustrated in FIG. 18B, the OPLD of embodiments of the present inventive concept would be less than 2 mm, which is a dramatic improvement for a typical OCT system designed to image a retina with a 2 mm to 3 mm imaging depth window. This design objective requires a mydriatic (dilated) eye or severe vignetting may occur. Dilation is commonly used in surgery, and therefore this presents no disadvantage. This is in stark contrast to diagnostic clinical imaging, where it is highly desirable to perform non-mydriatic imaging, and pushing the pivot forward of the pupil is not a suitable solution.

Various embodiments of the improved retinal surgical lens assembly in accordance with embodiments of the present inventive concept as well as related optical performance of these lens assemblies will now be discussed with respect to FIGS. 19A through 23B. Each of these configurations is designed to project the image of the scanning galvo pair, which defines the OCT scan pivot, deeper into the eye below the pupil plane.

Figure 19A:
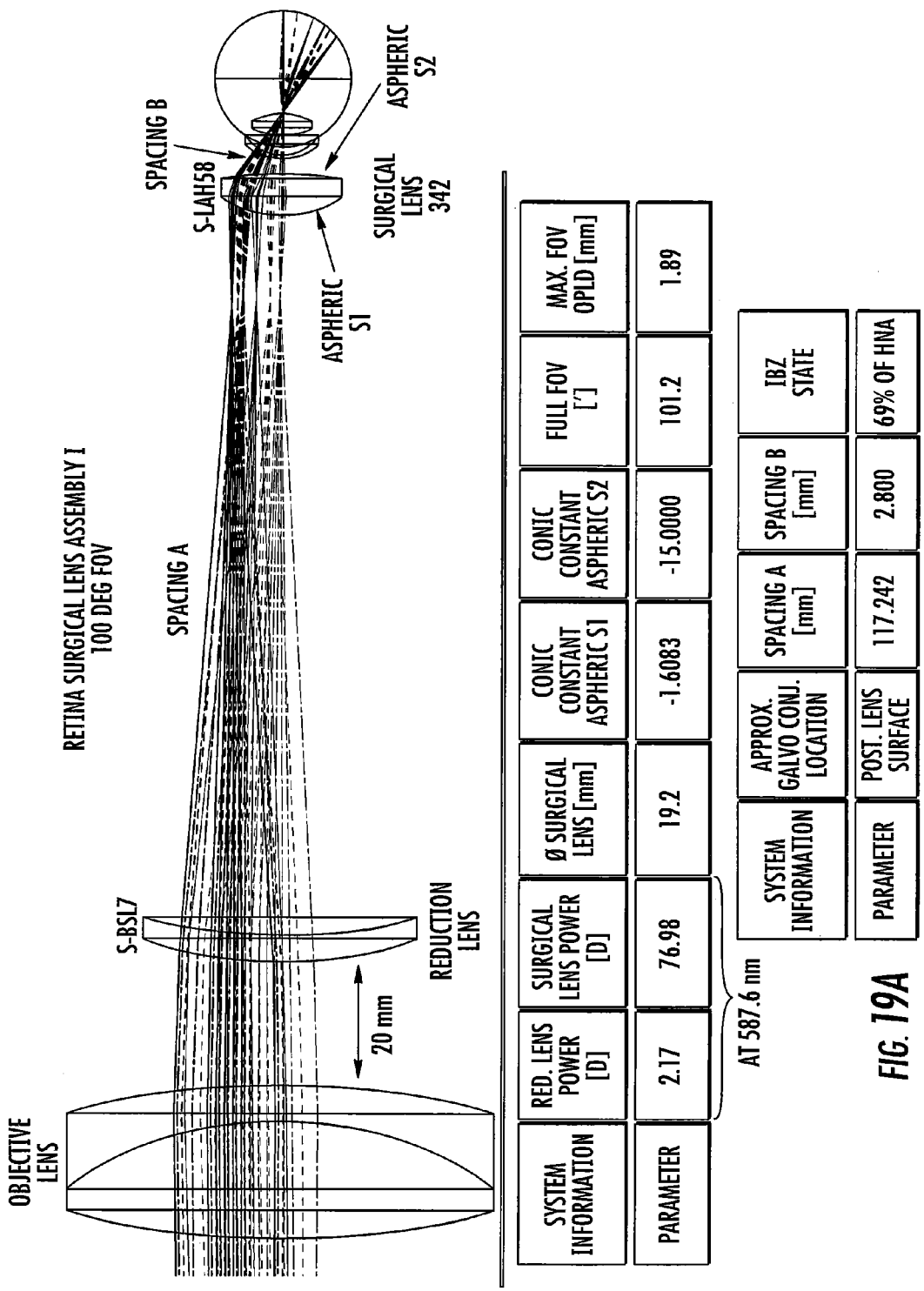
FIG. 19A is a diagram of a surgical retina lens assembly for OCT-integrated surgical microscopy having a wide FOV in accordance with some embodiments of the present inventive concept.

Referring first to FIG. 19A, a diagram of a surgical retina lens assembly having a 100 degree FOV in accordance with some embodiments of the present inventive concept will be discussed. As illustrated in FIG. 19A, a microscope objective lens is coupled to a reduction lens with a 20 mm spacing therebetween. The reduction lens is separated from the new retina lens 342 (FIG. 3) by a Spacing A (117 mm) and from the sample (eye) by a Spacing B (2.8 mm). Details of the lens designs and spacings are found in the table on FIG. 19A. The retinal lens 342 typically has a thickness of 6.6 mm from about 4 mm to about 10 mm. The system is described operating at an IBZ NA setting of 69% of the high NA setting.

Figure 19B:
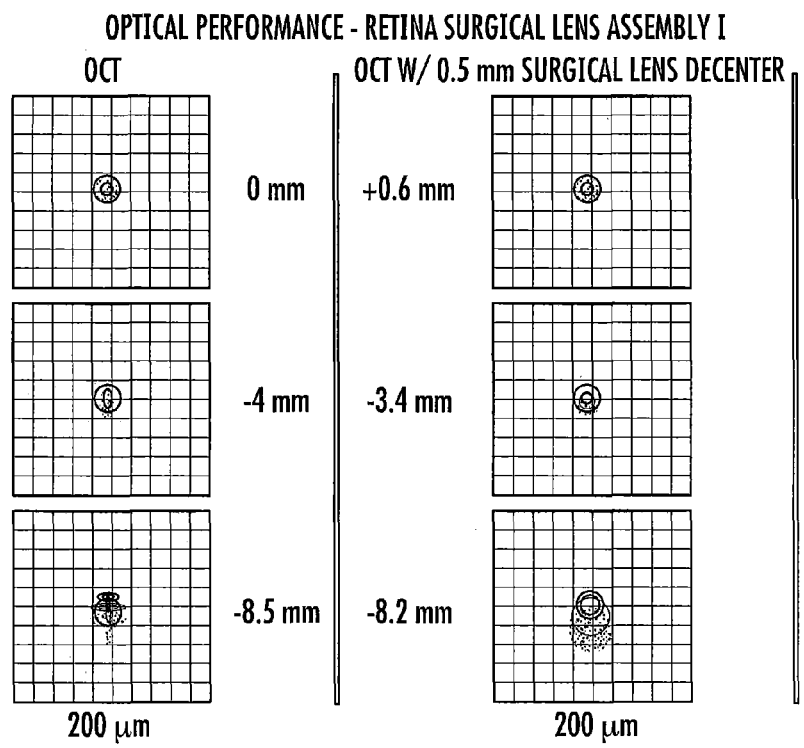
FIG. 19B are a series of graphs and diagrams illustrating optical performance of the surgical retina lens of FIG. 19A in accordance with some embodiments of the present inventive concept.

Referring now to FIG. 19B, a series of graphs and diagrams illustrating optical performance of the surgical retina lens having a 100 degree FOV of FIG. 19A in accordance with some embodiments of the present inventive concept will be discussed. The OCT spot pattern as a function of half-field of view is shown with the retina lens perfectly centered, and slightly decentered. The OCT beam has a center field beam diameter of 14 um, increasing to 80 um at the edge of the field of view (+−8.5 um, or +−50 degrees). The maximum OPLD across the field of view is 1.9 mm, assuring a reasonably flat OCT image across this wide field. The visible response for the microscope is also indicated at center field. The lateral resolution of the visible signal is approximately 22 um.

Figure 20A:
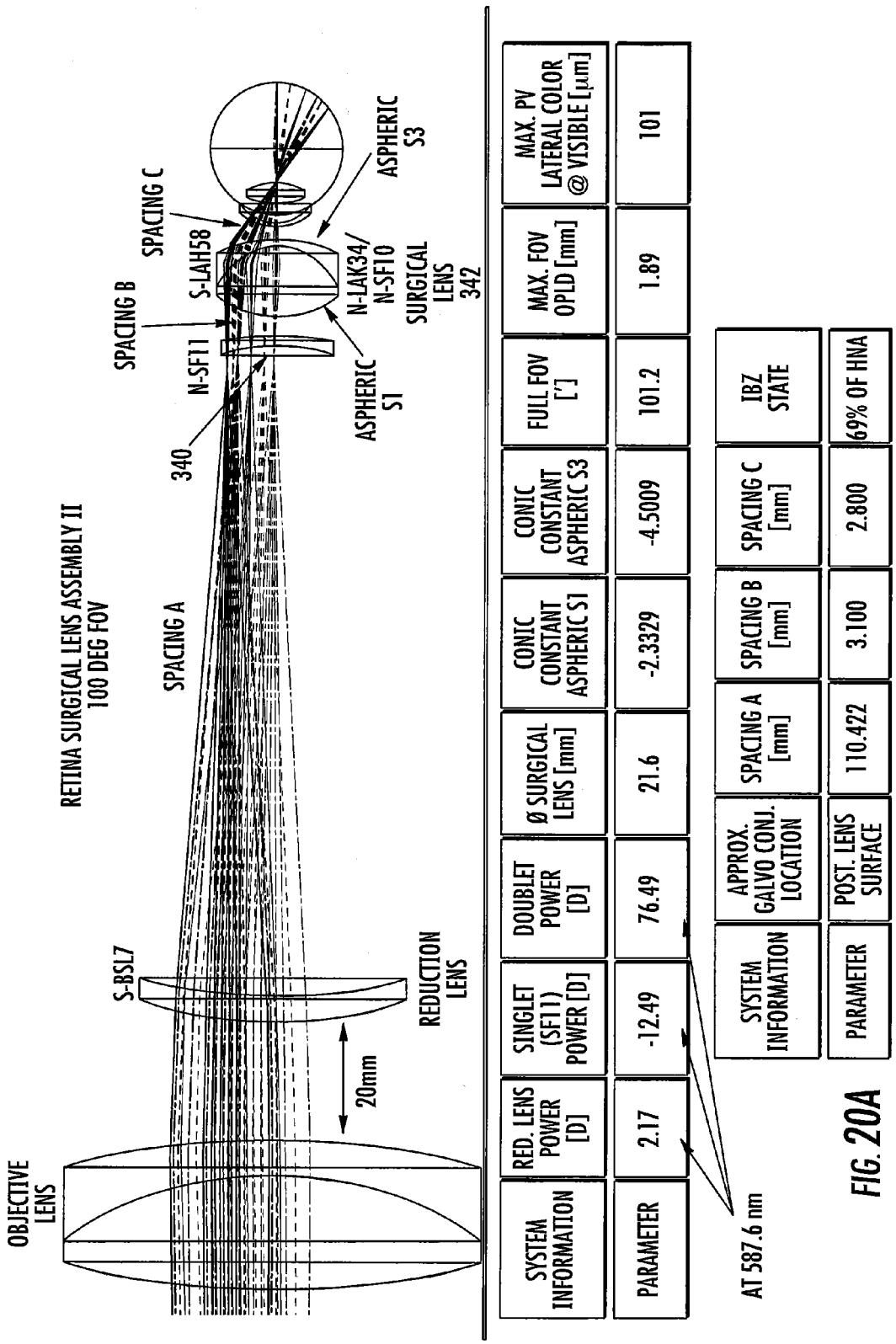
FIG. 20A is diagram illustrating a lens system for a surgical lens assembly for OCT-integrated surgical microscopy having a wide FOV in accordance with some embodiments of the present inventive concept.

Referring now to FIG. 20A, a diagram of a surgical retina lens assembly having a 100 degree FOV in accordance with some embodiments of the present inventive concept will be discussed. As illustrated in FIG. 20A, an objective lens is coupled to a reduction lens with a 20 mm spacing therebetween. The reduction lens is separated from a condenser 340 (FIG. 3) lens by a Spacing A. The retina lens 342 (FIG. 3) is separated from the condenser lens 340 by a Spacing B and from the sample (eye) by a Spacing C. Details of the spacings are found in the table on FIG. 20A.

Figure 20B:
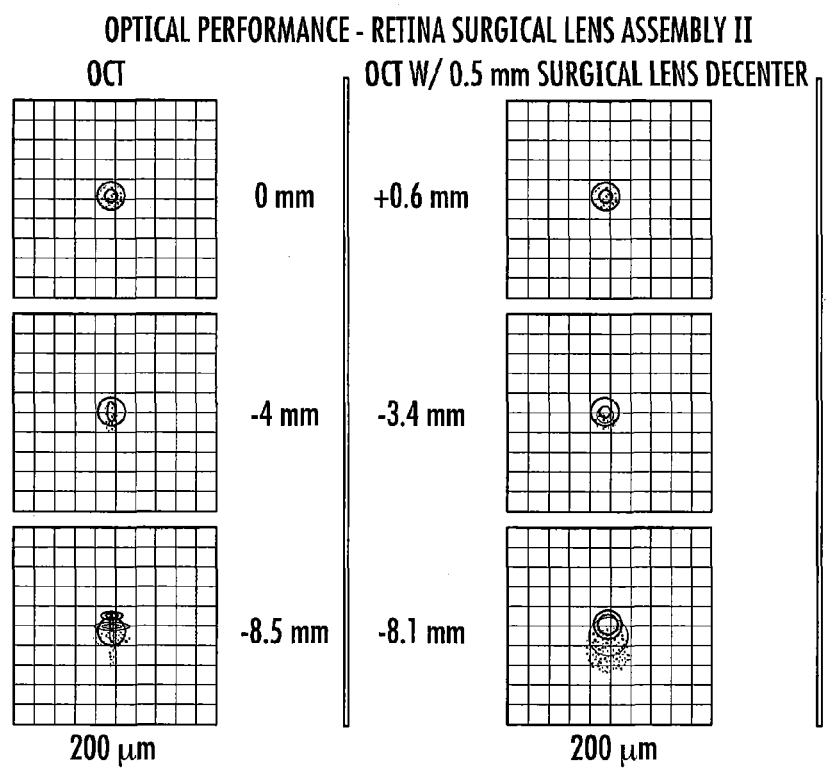
FIG. 20B is a diagram illustrating a summary of optical performance of the surgical lens assembly of FIG. 20B in accordance with some embodiments of the present inventive concept.

Referring now to FIG. 20B, a series of graphs and diagrams illustrating optical performance of the surgical retina lens having a 100 degree FOV of FIG. 20A in accordance with some embodiments of the present inventive concept will be discussed. The OCT spot pattern as a function of half-field of view is shown with the retina lens perfectly centered, and slightly decentered. The OCT beam has a center field beam diameter of 14 um, increasing to 28 um at the edge of the field of view (+−8.5 um, or +−50 degrees). The maximum OPLD across the field of view is 1.9 mm, assuring a reasonably flat OCT image across this wide field. The visible response for the microscope is also indicated at center field. The lateral resolution of the visible signal is approximately 40 um. The OCT performance is superior to the design of FIG. 19A, at a slight cost to the visible resolution and to lens complexity.

Figure 21A:
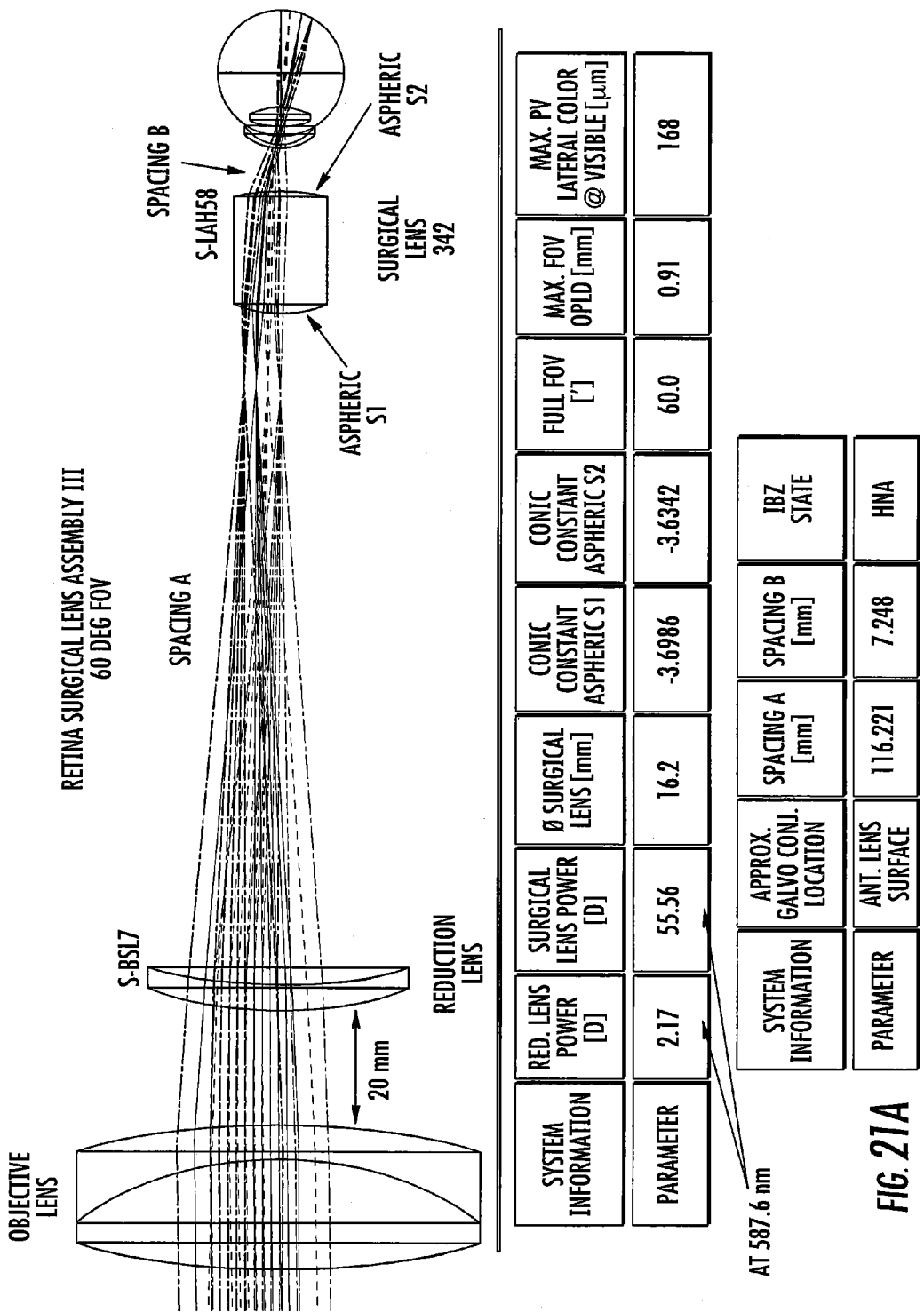
FIG. 21A is diagram illustrating a lens system for a surgical lens assembly for OCT-integrated surgical microscopy having a narrow FOV in accordance with some embodiments of the present inventive concept.

Referring now to FIG. 21A, a diagram of a surgical retina lens assembly having a 60 degree FOV in accordance with some embodiments of the present inventive concept will be discussed. As illustrated in FIG. 21A, an objective lens is coupled to a reduction lens with a 20 mm spacing therebetween. The reduction lens is separated from the retina lens 342 (FIG. 3) by a Spacing A and from the sample (eye) by a Spacing B. Details of the spacings are found in the table on FIG. 21A. The system is described operating in the high NA setting.

In this embodiment, the surgical aspheric lens 342 is a single double-sided aspheric lens, sandwiching an additional thickness which allows both surfaces to act as two individual lenses and provides additional correction due to substantially different chief ray heights on both surfaces while reducing back reflections and optical complexity by having fewer surfaces that could potentially reflect more light. It will be understood that the aspheric lens cannot be made arbitrarily thick for a number of reasons. First, since this lens serves to collimate outgoing light from the OCT system into the eye, it must not get too close to the retinal conjugate plane to avoid back reflections into the OCT system. Second, if the lens were made so thick that the retinal conjugate plane was internal to the lens then the lens would be extremely difficult to fabricate. In addition, this lens has both of its surfaces substantially symmetric in both base curvatures and eccentricities for somewhat reduced cost of fabrication.

In some embodiments, the P1 principle plane is 6.898 mm internal to the lens from the S1 surface while the P2 principle plane is −6.898 mm internal to the lens from the S2 surface and the lens is 21 mm thick. The relatively large distance of the principle planes from each surface is what allows substantially different chief ray heights at each surface. The maximum chief ray for OCT light is nearly telecentric near the retinal conjugate plane and makes an angle of 1.06 degrees with the optical axis. The maximum chief ray height at S1 of the retinal surgical lens is 6.122 mm while the same chief ray at S2 is only 3.878 mm, which allows each surface to nearly act as an individual lens. In some embodiments, the Base radii=25.697 mm (both convex); K=−3.679 (conic constant); Thickness=21 mm; and EFL=18 mm at 587.6 nm.

Figure 21B:
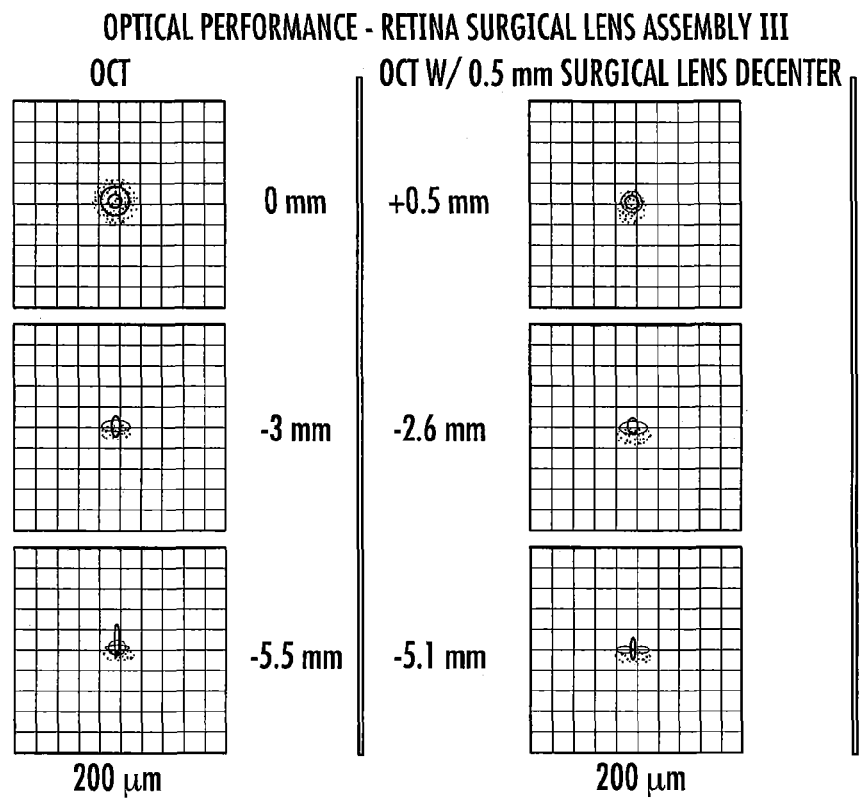
FIG. 21B is a diagram illustrating a summary of optical performance of the surgical lens assembly of FIG. 21A in accordance with some embodiments of the present inventive concept.

Referring now to FIG. 21B, a series of graphs and diagrams illustrating optical performance of the surgical retina lens having a sixty degree FOV of FIG. 21A in accordance with some embodiments of the present inventive concept will be discussed. The OCT spot pattern as a function of half-field of view is shown with the retina lens perfectly centered, and slightly decentered. The OCT beam has a center field beam diameter of 8 um, increasing to 17 um at the edge of the field of view (+−5.5 um, or +−30 degrees). The maximum OPLD across the field of view is 0.9 mm, assuring a reasonably flat OCT image across this wide field. The visible response for the microscope is also indicated at center field. The lateral resolution of the visible signal is approximately 32 um.

Figure 22A:
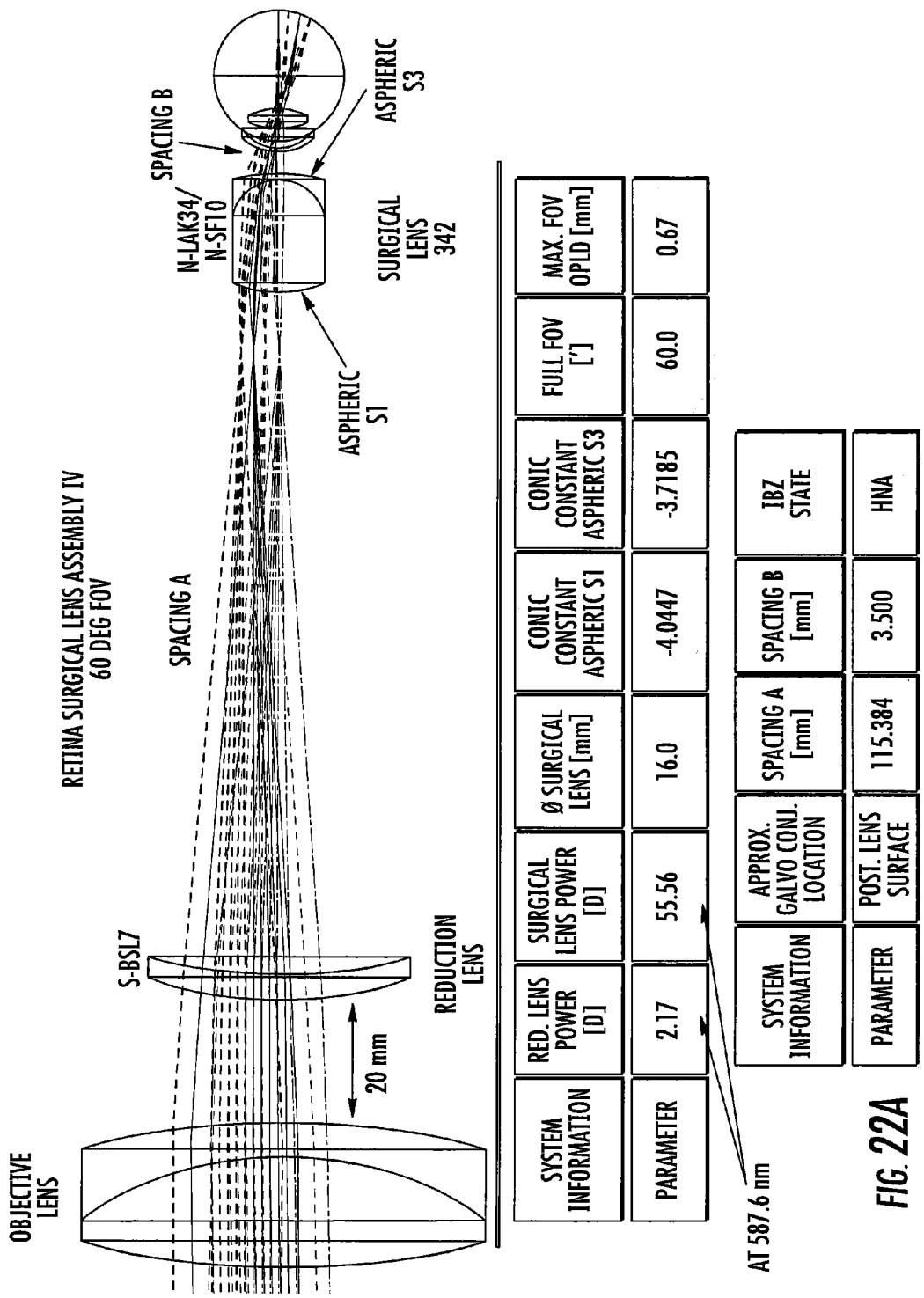
FIG. 22A is diagram illustrating a lens system for a surgical lens assembly having a narrow FOV in accordance with some embodiments of the present inventive concept.

Referring now to FIG. 22A, a diagram of a surgical retina lens assembly having a 60 degree FOV in accordance with some embodiments of the present inventive concept will be discussed. As illustrated in FIG. 22A, an objective lens is coupled to a reduction lens with a 20 mm spacing therebetween. The reduction lens is separated from the retina lens 342 (FIG. 3) by a Spacing A and from the sample (eye) by a Spacing B. Details of the spacings are found in the table on FIG. 22A.

Figure 22B:
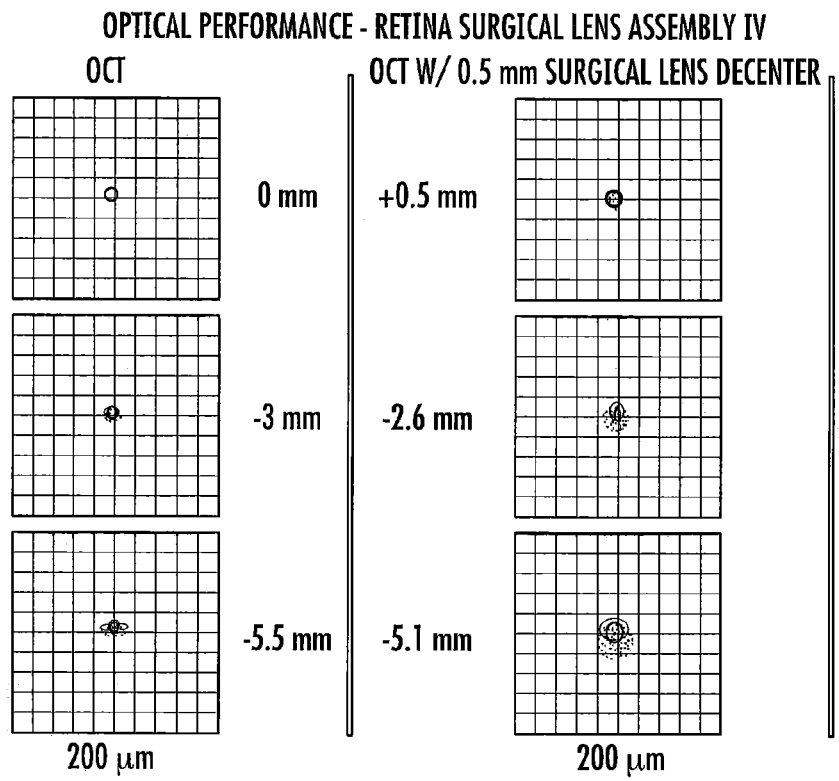
FIG. 22B is a diagram illustrating a summary of optical performance of the surgical lens assembly of FIG. 22A in accordance with some embodiments of the present inventive concept.

Referring now to FIG. 22B, a series of graphs and diagrams illustrating optical performance of the surgical retina lens having a sixty degree FOV of FIG. 22A in accordance with some embodiments of the present inventive concept will be discussed. The OCT spot pattern as a function of half-field of view is shown with the retina lens perfectly centered, and slightly decentered. The OCT beam has a center field beam diameter of 7 um, increasing to 9 um at the edge of the field of view (+−5.5 um, or +−30 degrees). The maximum OPLD across the field of view is 0.7 mm, assuring a reasonably flat OCT image across this wide field. The visible response for the microscope is also indicated at center field. The lateral resolution of the visible signal is approximately 45 um.

Figure 23A:
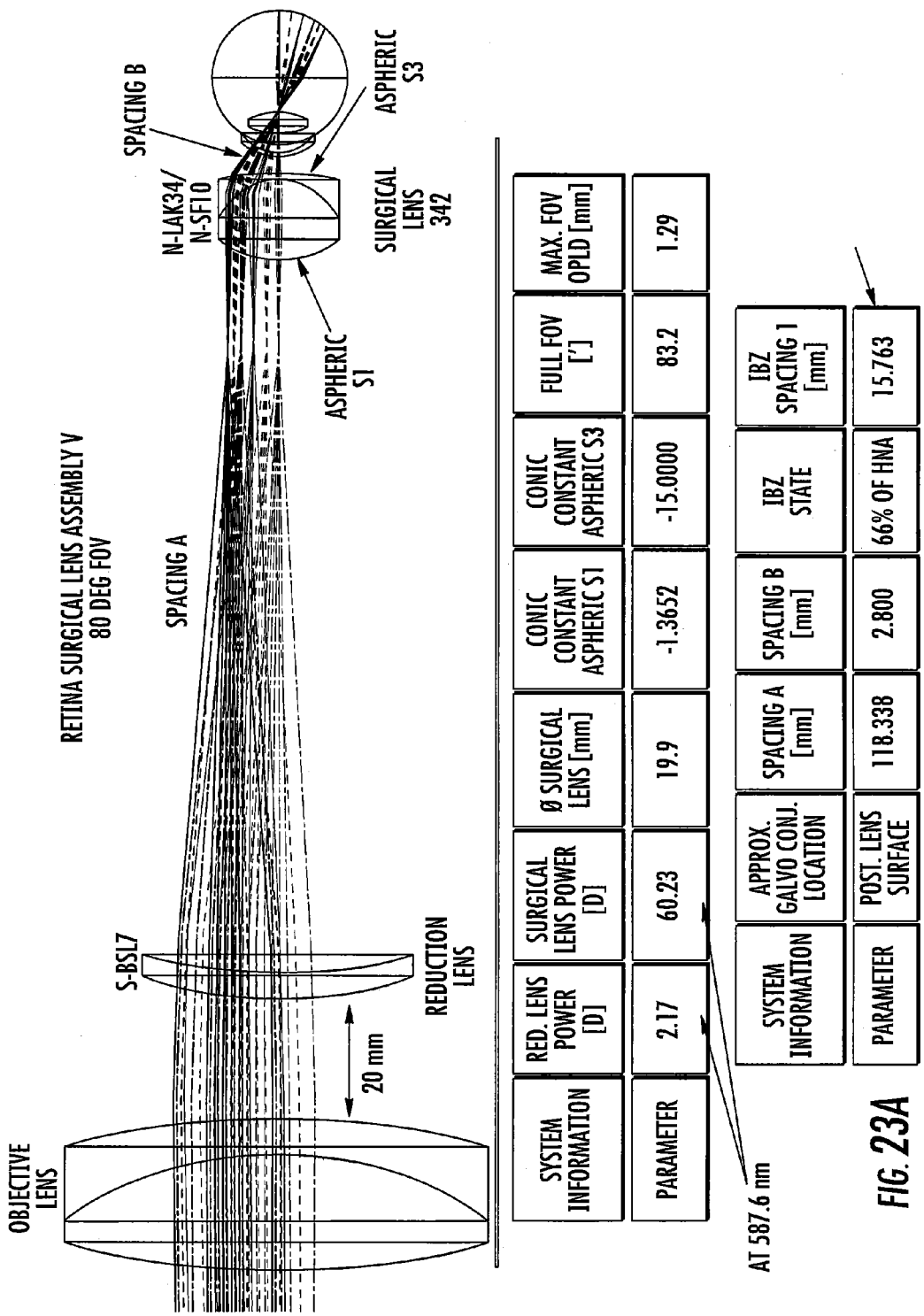
FIG. 23A is diagram illustrating a lens system for a surgical lens assembly having a mid-range FOV in accordance with some embodiments of the present inventive concept.

Referring now to FIG. 23A, a diagram of a surgical retina lens assembly having a 80 degree FOV in accordance with some embodiments of the present inventive concept will be discussed. As illustrated in FIG. 23A, an objective lens is coupled to a reduction lens with a 20 mm spacing therebetween. The reduction lens is separated from the retina lens 342 (FIG. 3) by a Spacing A and from the sample (eye) by a Spacing B. Details of the spacings are found in the table on FIG. 23A.

Figure 23B:
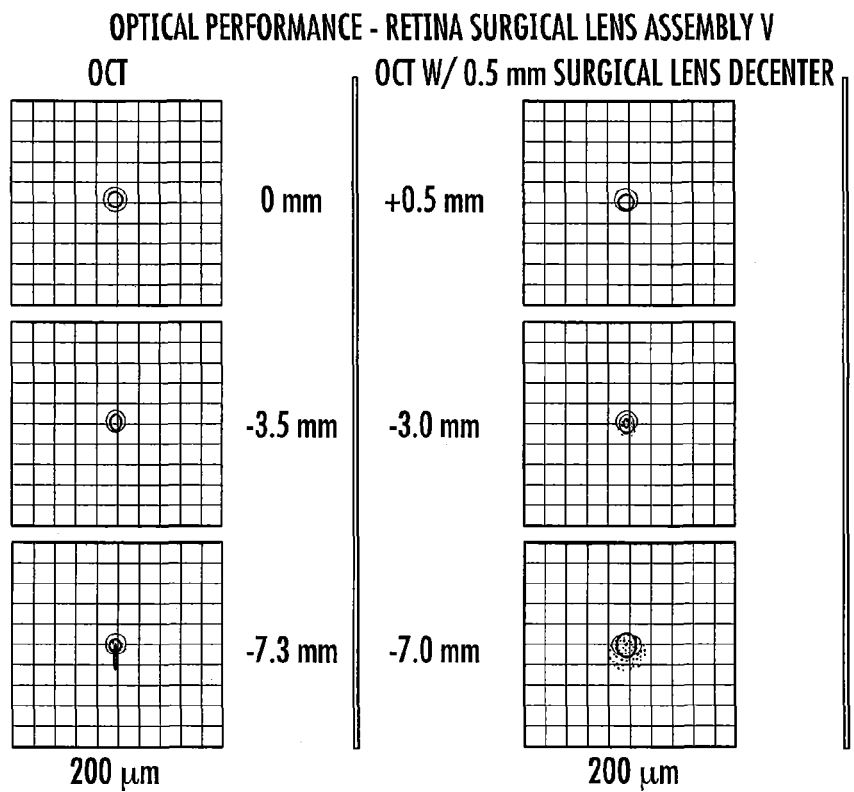
FIG. 23B is a diagram illustrating a summary of optical performance of the surgical lens assembly of FIG. 23A in accordance with some embodiments of the present inventive concept.

Referring now to FIG. 23B, a series of graphs and diagrams illustrating optical performance of the surgical retina lens having an 80 degree FOV of FIG. 23A in accordance with some embodiments of the present inventive concept will be discussed. The OCT spot pattern as a function of half-field of view is shown with the retina lens perfectly centered, and slightly decentered. The OCT beam has a center field beam diameter of 12 um, increasing to 16 um at the edge of the field of view (+−7.3 um, or +−40 degrees). The maximum OPLD across the field of view is 1.3 mm, assuring a reasonably flat OCT image across this wide field. The visible response for the microscope is also indicated at center field. The lateral resolution of the visible signal is approximately 48 um.

The embodiments of the present invention described above are general for the integration of an OCT coupling element into the infinity space of the stereo zoom surgical microscope, folding into the imaging path of the microscope with a dichroic filter. The constraints have been limited to access to this infinity space. An alternate embodiment is to direct at least a portion of the optical path in parallel with the ocular paths of the microscope, to minimize or eliminate the need to couple elements into the infinity space, thereby potentially obviating any impact to the surgical working distances, and potentially yielding a more compact, streamlined multimodal imaging system. This implementation concept will be referred to as a center-channel OCT (surgical) microscope (CCOM).

When considering how to construct a CCOM, i.e. to integrate an OCT system into a surgical stereo-microscope, the parameters that define the OCT beam should be defined. There are three primary parameters that characterize the OCT beam: (1) the focused beam numerical aperture or NA; (2) the field of view over which the focused beam can be scanned; and (3) the degree of telecentricity of the focused beam over the scanned field. The equations governing how these parameters are related to microscope system parameters are discussed below with reference to FIGS. 24 through 27 below.

Figure 24:
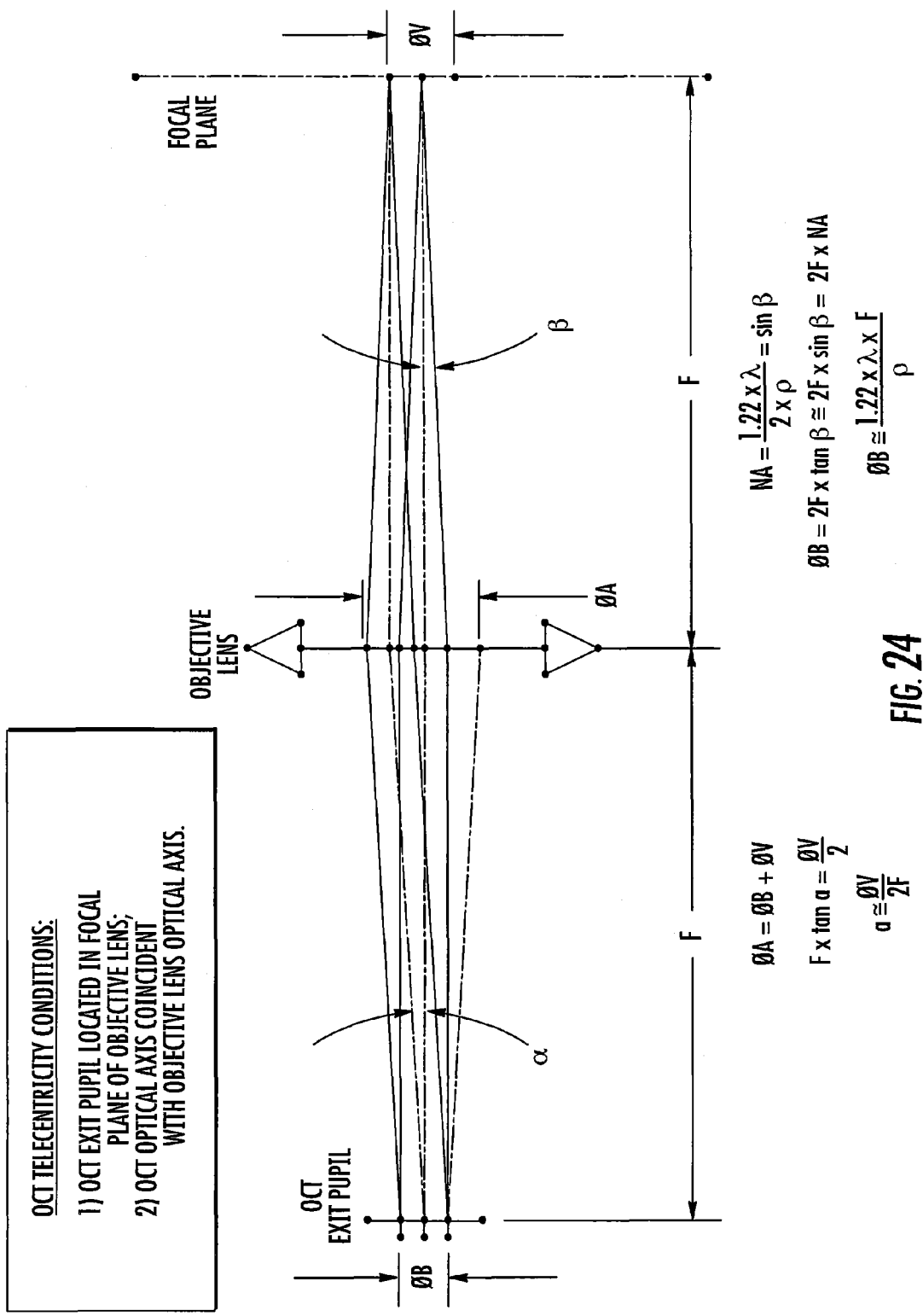
FIG. 24 is a diagram illustrating OCT telecentricity conditions in accordance with some embodiments of the present inventive concept.

Referring first to FIG. 24, a diagram illustrating OCT telecentricity conditions in accordance with some embodiments of the present inventive concept. If telecentric scanning is required, then the telecentric conditions also need to be met: 1) the exit pupil of the OCT system lies in a focal plane of the microscope objective lens; and 2) the optical axes of the OCT and microscope objective lens are collinear.

$NA_O$ is the OCT numerical aperture as defined by the focus beam half-angle; the maximum NA at which the OCT operates determines its limiting lateral resolution. $NA_O$ is represented by Equation (3) set out below:

$$NA_O = \frac{1.22 \cdot \lambda_O}{2 \cdot \rho} = \sin\beta$$

where $\beta$ is the OCT focus beam half angle; $\lambda_O$ is the OCT center wavelength; and p is the OCT lateral resolution, assumed to be equal to the Airy disk radius. $\varnothing B$ is the OCT collimated beam diameter, i.e. the OCT beam in infinity space between the exit pupil and the objective lens. $\varnothing B$ is represented by Equation (4) set out below:

$$\varnothing B \cong \frac{1.22 \cdot \lambda_O \cdot F}{\rho} = 2F \cdot NA_O$$

where F is the effective focal length of the surgical microscope objective lens and is tied to the scanned field of view $\varnothing V$ by Equation (5) set out below:

$$F \cdot \tan\alpha = \frac{\varnothing V}{2},$$

where $\tan\alpha \approx \alpha$ for small angles, we have $$\alpha \cong \frac{\varnothing V}{2F},$$

where $\alpha$ is the maximum scan angle of the OCT system. $\varnothing V$ is the Field-of-view diameter of the OCT-microscope lens system.

$\varnothing A$ is the Clear aperture diameter on the objective lens required for the OCT beam and represented by Equation (6) set out below:

$$\varnothing A = \varnothing B + \varnothing V$$

Surgical stereo-microscopes typically use two or more afocal relay zoom lens (ARZL) systems looking through a common objective lens. The individual ARZL systems for left and right viewing channels have their optical axes parallel to and offset from the common objective lens optical axis to provide stereopsis. Each viewing channel in the body of a surgical stereo-microscope consists of the following key optical systems, listed in order starting from the object (or subject): 1) the common objective lens; 2) an afocal zoom relay system; 3) a tube lens to form an intermediate image; and 4) an erecting prism system to correct the image orientation. The intermediate images for each viewing channel are imaged to final detectors—these can be either a surgeon's eyes or cameras—via binocular eyepiece lens systems. Since the binocular eyepiece systems are often designed to be exchangeable modules, they need not be considered when contemplating the integration of an OCT system into the surgical microscope. Furthermore, the erecting prism system and tube lens are usually standardized for a family of stereo-microscope designs, which means that their parameters do not drive the design of OCT system integration. This leaves the afocal relay zoom lens system and the objective lens as the optical systems of primary importance in driving integrated OCT system design.

Figure 25:
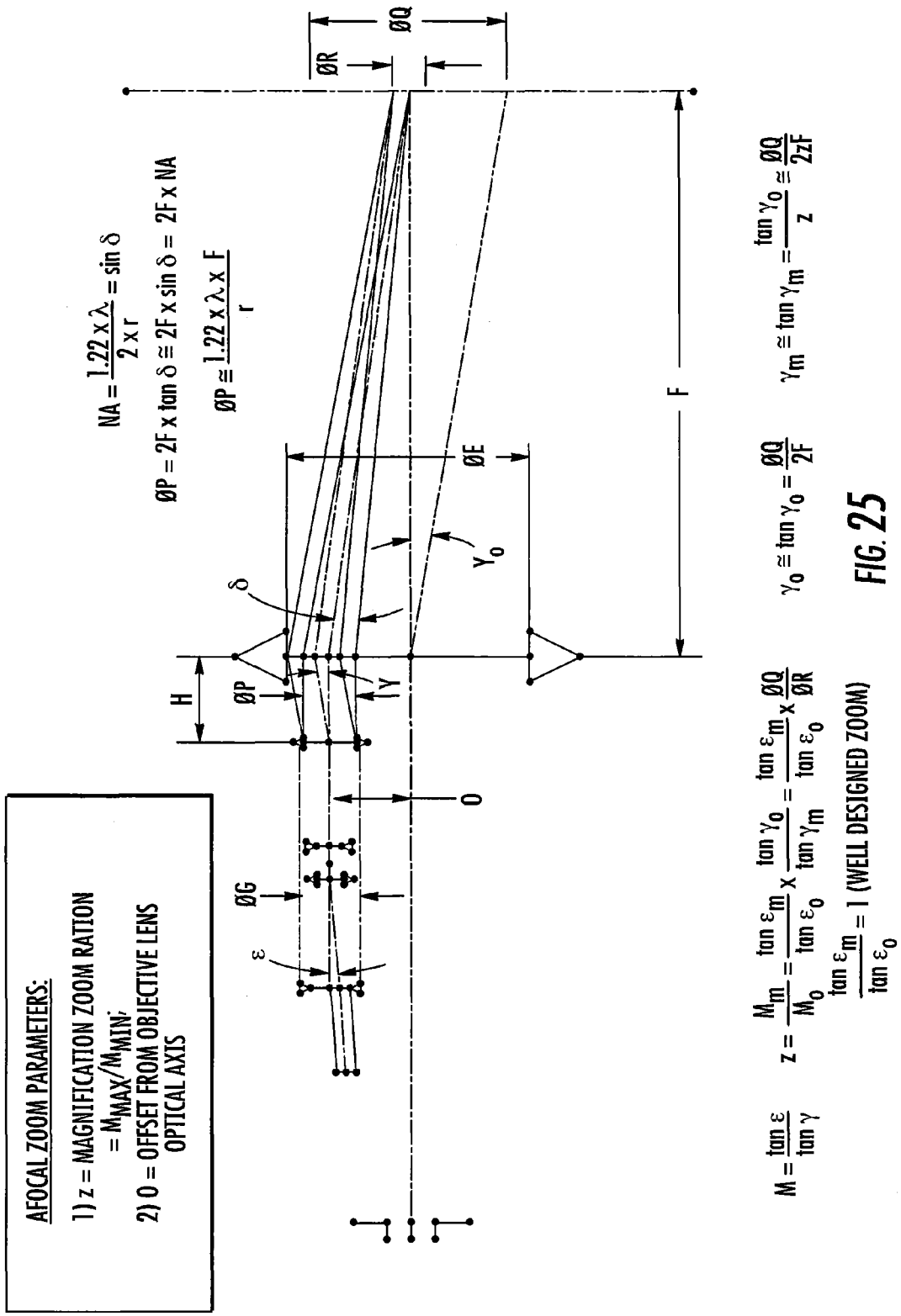
FIG. 25 is a diagram illustrating Afocal Relay Zoom Lens conditions of a Surgical Stereo Microscope in accordance with some embodiments of the present inventive concept.

Referring now to FIG. 25, a diagram illustrating Afocal Relay Zoom Lens conditions of a Surgical Stereo Microscope in accordance with some embodiments of the present inventive concept will be discussed. The Afocal relay zoom lens system is characterized by 3 key parameters: (1) the operating NA at maximum magnification; (2) the field of view at minimum magnification; and (3) the zoom ratio, or ratio of maximum to minimum magnification. Since the afocal relay zoom lens system functions in the infinity space above the objective lens, the magnification it provides is purely angular. The equations listed below govern how the afocal relay zoom lens system parameters relate to the stereo-microscope system parameters.

$NA_m$ is the microscope single viewing channel numerical aperture as defined by the focus beam half-angle above; the maximum NA at which the microscope operates determines its limiting lateral resolution. $NA_m$ is represented by Equation (7) set out below:

$$NA_m = \frac{1.22 \cdot \lambda_m}{2 \cdot r} = \sin\delta$$

where $\delta$ is the Microscope viewing channel focus beam half angle; $\chi_m$ is the microscope viewing channel center wavelength; and r is the Microscope viewing channel lateral resolution, assumed to be equal to the Airy disk radius.

$\varnothing P$ is the Microscope viewing channel infinity space beam diameter and is represented by Equation (8) set out below:

$$\varnothing P \cong \frac{1.22 \cdot \lambda_m \cdot F}{r} = 2F \cdot NA_m$$

where F is the effective focal length of the surgical microscope objective lens. M is the magnification of the afocal relay zoom lens and is represented by Equation (9) set out below:

$$M = \frac{\tan\varepsilon}{\tan\gamma}$$

where $\gamma$ is the object side chief ray angle for afocal relay zoom lens and $\varepsilon$ is the image side chief ray angle for afocal relay zoom lens.

$\gamma_o$ is the chief ray angle for object field point at edge of minimum magnification field of view and is represented by Equation (10) set out below:

$$\gamma_o \cong \tan\gamma_o = \frac{\emptyset Q}{2F}$$

where $\emptyset Q$ is the diameter of microscope field of view at minimum magnification.

z is the Afocal relay zoom lens magnification ratio (typically z=6 for surgical stereo-microscopes) and is represented by Equation (11) set out below:

$$z = \frac{M_m}{M_o} = \frac{\tan\varepsilon_m}{\tan\varepsilon_o} \cdot \frac{\tan\gamma_o}{\tan\gamma_m} = \frac{\tan\varepsilon_m}{\tan\varepsilon_o} \cdot \frac{\emptyset Q}{\emptyset R}$$

where $M_m$ is the maximum afocal relay zoom lens magnification; $M_o$ is the minimum afocal relay zoom lens magnification; $\gamma_m$ is the chief ray angle for object field point at edge of maximum magnification field of view; $\varepsilon_m$ is the Chief ray angle on image side of afocal relay zoom lens for $\gamma_m$ input (max. magnification); $\varepsilon_o$ is the Chief ray angle on image side of afocal relay zoom lens for $\gamma_o$ input (min. magnification); and OR is the diameter of microscope field of view at maximum magnification.

Equation (12) set out below illustrates how the full-field chief ray angles on the object side of the afocal relay zoom lens are related at the zoom extremes.

$$\gamma_m \cong \tan\gamma_m = \frac{\tan\gamma_o}{z} \cong \frac{\emptyset Q}{2zF}$$

For a well-designed afocal relay zoom lens, the apparent location of the image should not change as the magnification is varied. This condition is expressed by Equation (13) set out below:

$$\frac{\tan\varepsilon_m}{\tan\varepsilon_o} = 1 \text{ (well designed zoom)}$$

With the performance conditions of a stereo zoom surgical microscope defined, constraints and design conditions for a CCOM can be defined.

Figure 26:
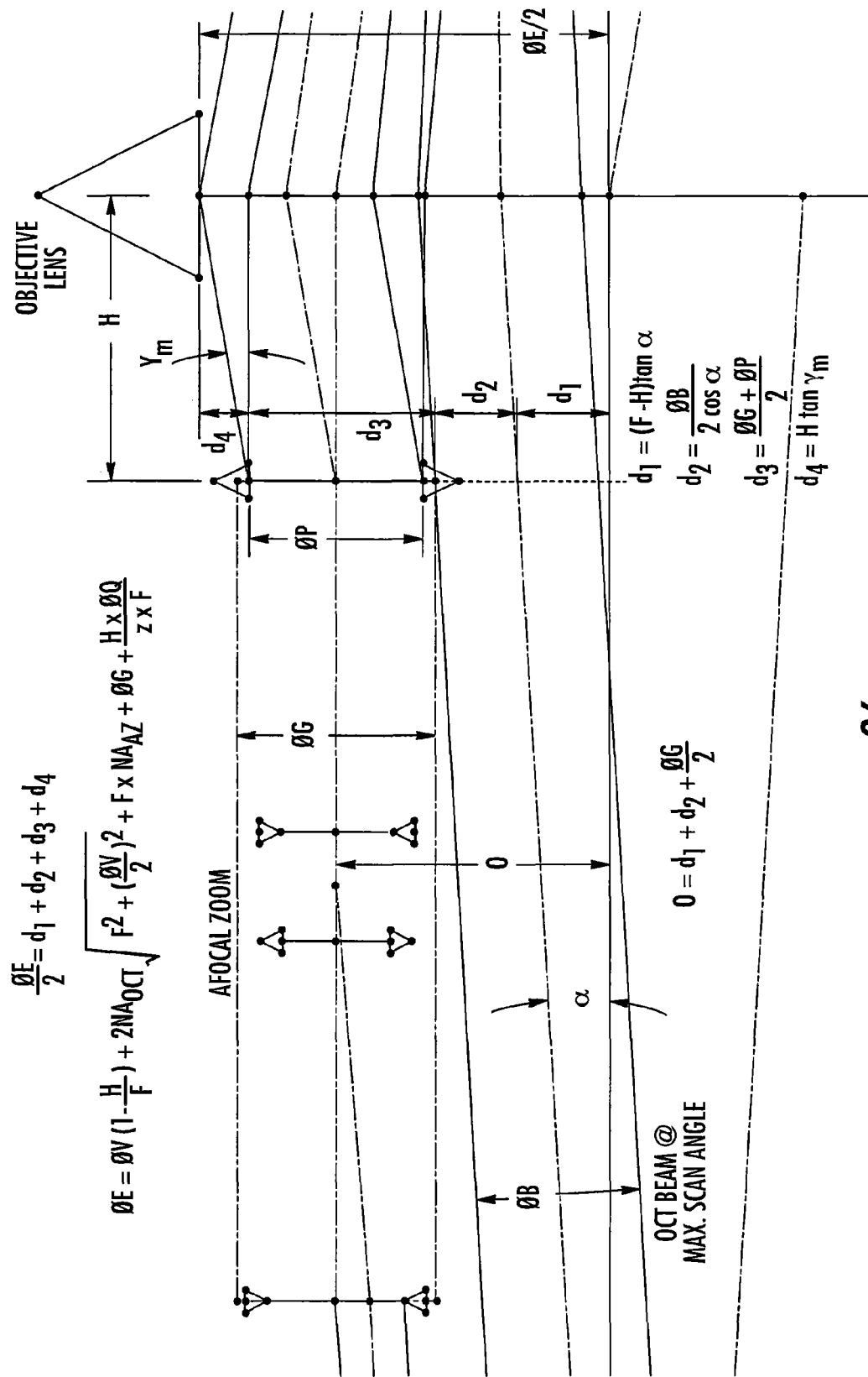
FIG. 26 is a diagram illustrating conditions of an OCT center channel OCT-integrated Surgical Stereo Microscope in accordance with some embodiments of the present inventive concept.

Referring now to FIG. 26, a diagram illustrating conditions of a center channel OCT-integrated Surgical Stereo Microscope (CCOM) in accordance with some embodiments of the present inventive concept will be discussed. One way to integrate an OCT system into a surgical stereo-microscope while satisfying the telecentric scanning conditions described above is to make room for the OCT beam centered on the objective lens optical axis with the ARZL systems (2 or 4, depending on whether there are dedicated viewing channels for an assistant to the surgeon) offset from the objective lens optical axis by a minimum distance that allows the OCT beam path to stay clear. In some embodiments, the barrel of the ARZL system just touches the OCT beam at maximum scan angle. In these embodiments, the minimum ARZL offset and minimum objective lens edge diameter can be calculated according to the equations discussed below.

This first-order analysis assumes that the exit pupil of the ARZL is coincident with the bottom lens and mechanical barrel. In reality this will not be the case, but this is a close approximation.

$\emptyset E$ is the minimum edge diameter of microscope objective lens that will fit an OCT system and ARZL system with given parameters and is represented by Equation (14) set out below:

$$\frac{\emptyset E}{2} = d_1 + d_2 + d_3 + d_4$$

where $d_1 \ldots d_4$ are lateral distances as shown in FIG. 26 with exact relations given individually below.

O is the offset of ARZL optical axis from objective lens optical axis and is represented by Equation (15) set out below:

$$O = d_1 + d_2 + \frac{\emptyset G}{2}$$

where $\emptyset G$ is the ARZL mechanical barrel diameter.

The distance $d_1$ from objective lens optical axis to OCT beam chief ray at maximum scan angle measured in the plane of the exit pupil of the ARZL is represented by Equation (16) set out below:

$$d_1 = (F-H)\cdot\tan\alpha$$

where H is the height of the ARZL above the objective lens.

The distance $d_2$ from the OCT beam chief ray at maximum scan angle to the edge of the ARZL mechanical barrel measured in the plane of the exit pupil of the ARZL when the OCT beam just grazes the ARZL barrel is represented by Equation (17) set out below:

$$d_2 = \frac{\emptyset B}{2\cos\alpha}$$

The distance $d_3$ from the inside edge of the ARZL barrel to the outside edge of the full-field viewing channel ray bundle measured in the plane of the ARZL exit pupil is represented by Equation (18) set out below:

$$d_3 = \frac{\emptyset G + \emptyset P}{2}$$

The distance $d_4$ from the outside edge of the full-field viewing channel ray bundle to the edge of the objective lens measured in the plane of the ARZL exit pupil is represented by Equation (19) set out below:

$$d_4 = H \tan\gamma_m$$

The full expression for the minimum objective lens diameter needed to fit a centered OCT channel surrounded by ARZL(s) with the given parameters is represented by Equation (20) set out below:

$$\emptyset E = \emptyset V\left(1 - \frac{H}{F}\right) + 2NA_{OCT}\sqrt{F^2 + \left(\frac{\emptyset V}{2}\right)^2} + F\cdot NA_{AZ} + \emptyset G + \frac{H\cdot\emptyset Q}{z\cdot F}$$

For the highest NA (high resolution) OCT systems, the ARZL offsets and objective lens diameters may need to be impractically large. In such circumstance, it may be desirable to design a hybrid between the infinity-space coupled design and the CCOM design for a folded-path center-channel OCT (surgical) microscope (FCCOM).

Figure 27:
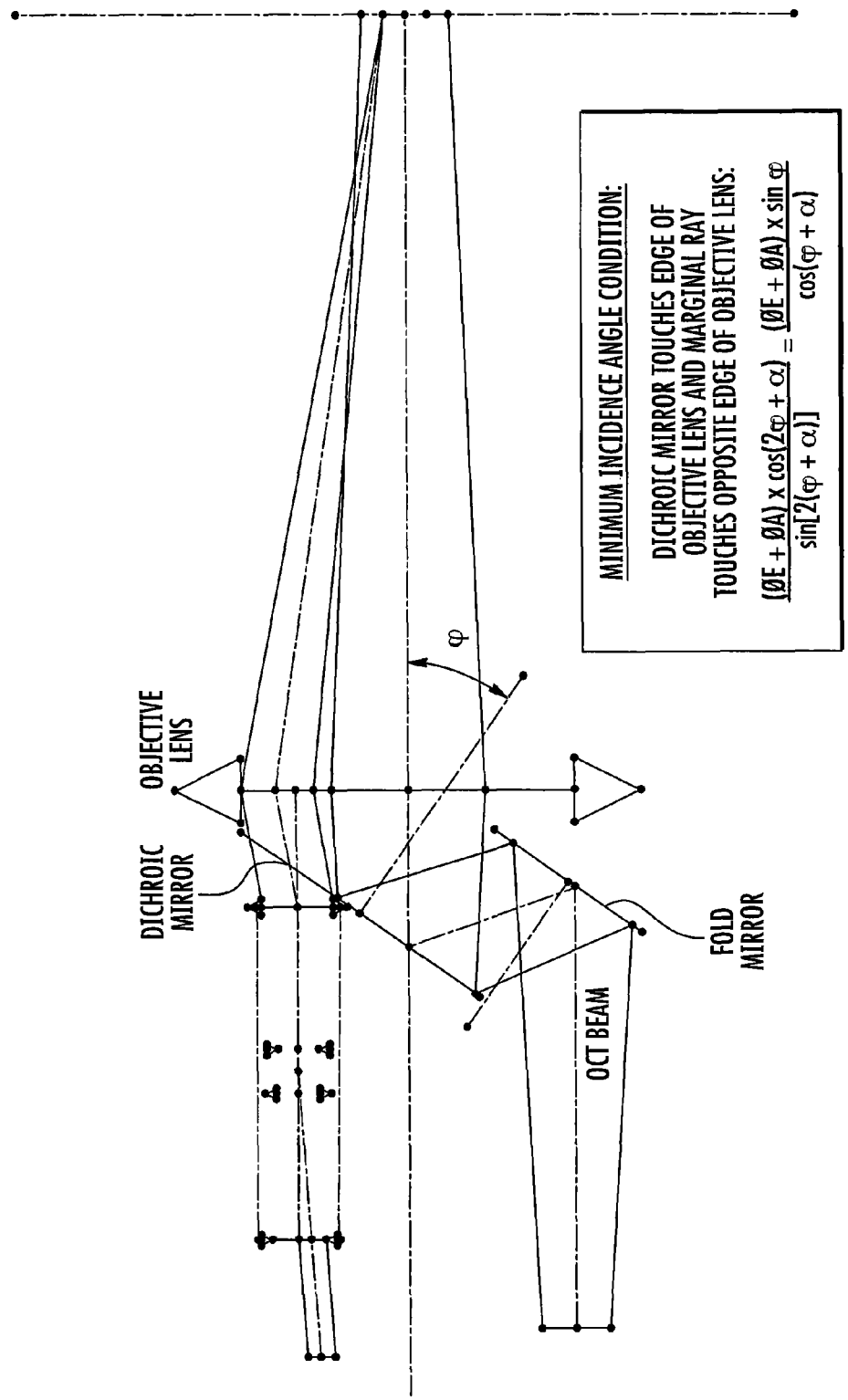
FIG. 27 is a diagram illustrating conditions of folded path OCT center channel OCT-integrated Surgical Stereo Microscope in accordance with some embodiments of the present inventive concept.

Referring now to FIG. 27, a diagram illustrating conditions of folded path center channel OCT-integrated Surgical Stereo Microscope (FCCOM) in accordance with some embodiments of the present inventive concept will be discussed. In these embodiments, a dichroic mirror is used in the space between the ARZL and the objective lens to fold in the OCT beam, while the microscope viewing paths look through it. A goal is to minimize the space required to accomplish this fold, primarily to reduce the height of the microscope body. The minimum height is achieved when the incidence angle, $\phi$, is a minimum. For the extreme case where the dichroic mirror just touches the outside edge of the objective lens and the folded OCT beam just touches the opposite edge of the objective lens, the minimum angle condition is given by Equation (21) set out below:

$$\frac{(E+A)\cdot\cos(2\varphi+\alpha)}{\sin[2(\varphi+\alpha)]} = \frac{(E-A)\cdot\sin\varphi}{\cos(\varphi+\alpha)}$$

This equation is non-linear and cannot be solved analytically, but can be solved numerically. For typical surgical stereo-microscope and high NA OCT parameters, $\phi_{min}$ works out to be approximately 37°. Note that in this geometry, the angle $\phi$ is related to the dichroic angle as described in Eqn. (1) above by $\phi=90°-\theta$, and therefore the maximum value of $\theta$ is approximately 53°.

It is not necessary that the folding dichroic mirror extend across the entire diameter of the common objective lens. If the ARZL systems are localized, then the dichroic mirror need only be large enough to not clip the microscope viewing channels. This arrangement may have advantages for introducing illumination of the focal plane via the dichroic and/or fold mirrors. In conventional surgical stereo-microscopes the illumination systems are typically introduced in the space between ARZL and objective lens. Thus, in the folded OCT configuration this space can be used for a dual purpose: illumination and coupling of the OCT system while minimizing impact to surgical working distances, in accordance with embodiments discussed herein.

Figure 28:
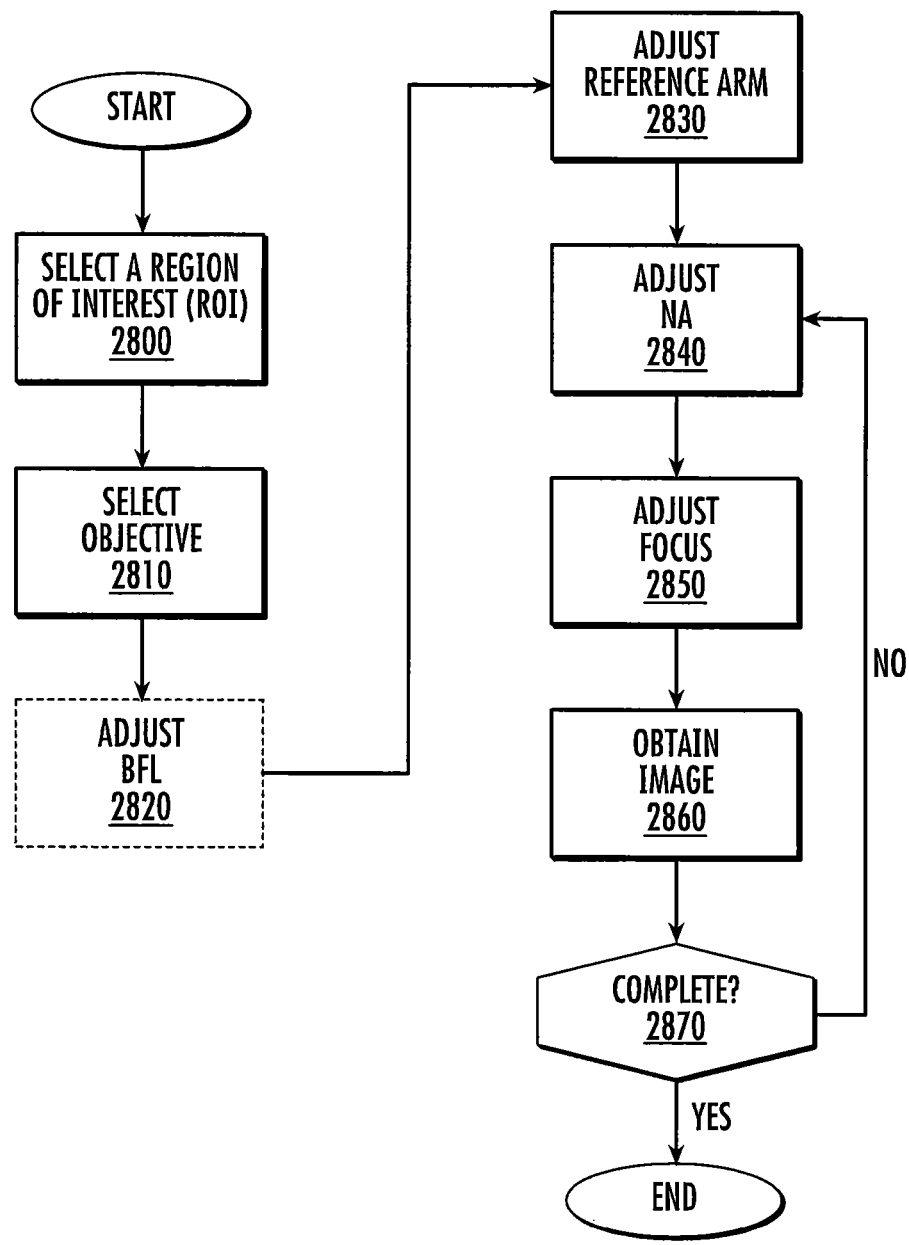
FIG. 28 is a flowchart illustrating a method of imaging using an OCT-integrated surgical microscope in accordance with some embodiments of the present inventive concept.

Referring now to FIG. 28, a flowchart illustrating a method of imaging using a surgical microscope in accordance with some embodiments of the present inventive concept will be discussed. Operations begin at block 2800 by selecting a region of interest (ROI) in the sample, for example, an eye, with a ROI being one of a cornea, a lens, an anterior segment, a posterior segment, a retina, or the like. A microscope main objective and any accessory lenses are selected and configured to the microscope system (block 2810), for example, an optimized 175 mm focal length objective and a 100 degree surgical retinal lens. If required, the OCT path may be adjusted such that the back focal length matches the objective lens (block 2820). The reference arm is adjusted accordingly (block 2830) such that the reference arm path length matches the OCT path length to the ROI. The numerical aperture (block 2840) is adjusted so that image brightness meets the surgical uniformity requirement and lateral resolution meet the surgical resolution requirements. Focus (block 2850) is adjusted so that the optimum focus is targeted at the depth of interest within the ROI; the focal position may be at the microscope focal plane, or above or below this plane according to needs of the surgeon. The image, images, or continuous video display is obtained (block 2860) using these settings. A determination is made whether the desired image(s) have been obtained (block 2870). If the desired images have been obtained (block 2870) with the desired image quality, operations may cease until another image is desired. If, on the other hand, it is determined that desired image(s) have not been obtained, operations return to block 2840 and repeat until the desired images and image quality are obtained.

Figure 29:
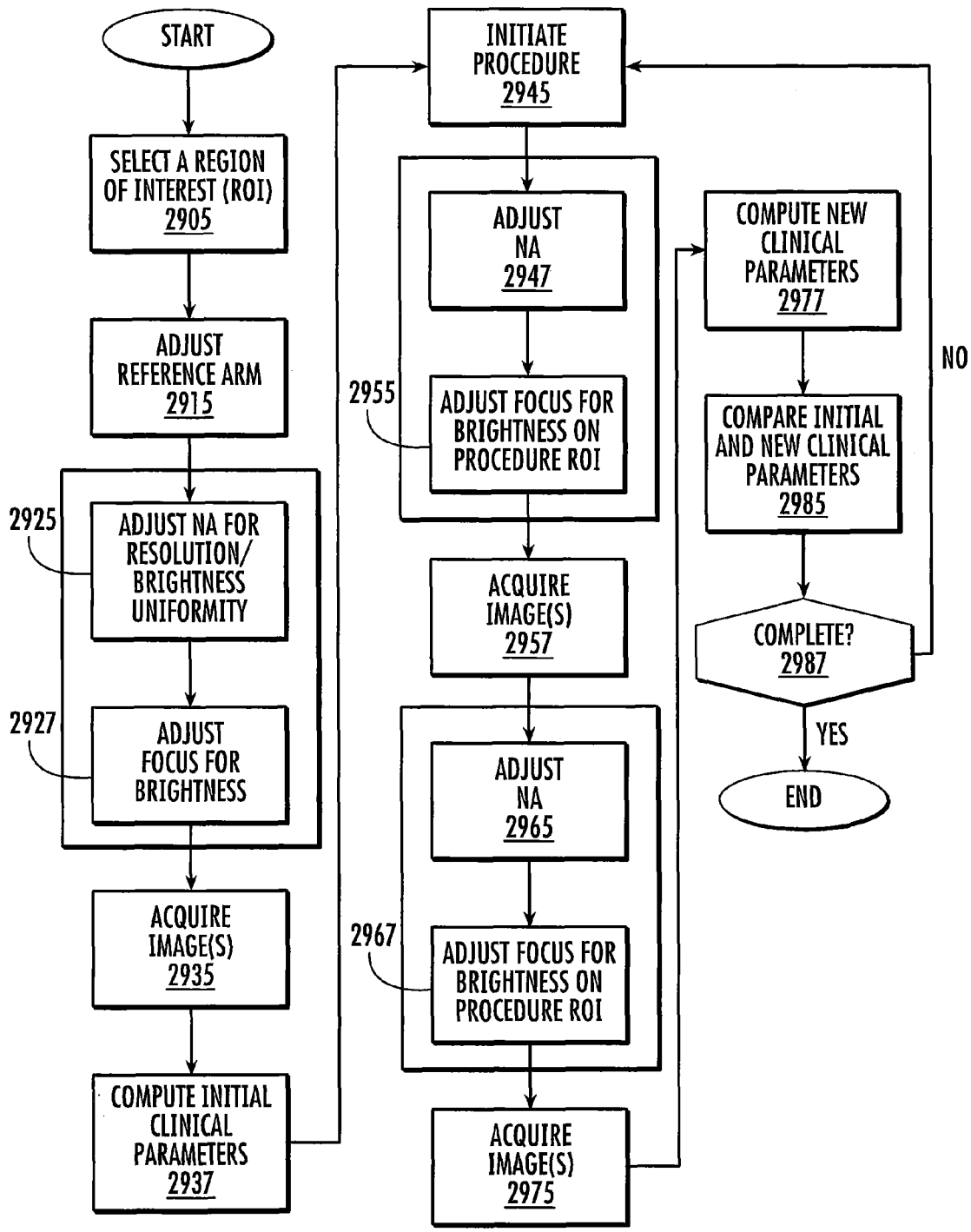
FIG. 29 is a flowchart illustrating a method of imaging during a surgical procedure using an OCT-integrated surgical microscope in accordance with some embodiments of the present inventive concept.

Referring now to FIG. 29, a flowchart illustrating a method of imaging during a surgical procedure using an OCT-integrated surgical microscope in accordance with some embodiments of the present inventive concept. As illustrated in FIG. 29, operations begin at block 2905 by selecting a ROI to be imaged in the sample, for example, the eye, and as described above. The reference arm is adjusted (block 2915). The NA for resolution/brightness uniformity (block 2925) and the focus for brightness (block 2927) are adjusted. Images are acquired using the current settings (block 2935). An initial set of clinical parameters are computed based on the current settings and the acquired images (block 2937).

These clinical parameters may include a shape of an anterior surface of a cornea, the shape of an anterior stromal surface of a cornea, the shape of an endothelia surface of a cornea, and any relevant parameters that may be derived from such measures, including but not limited to pachymetry maps, curvature maps, refractive powers, aberration maps, keratometry values and the like. Clinical parameters may further include an iridocorneal angle, a sclera thickness, a bleb geometry, a Canal of Schlemm position and the like. Clinical parameters may also include a pupil diameter, a lens capsule thickness, a lens thickness, or the like. Clinical parameters may still yet include a retinal membrane area or thickness, a thickness of a particular retinal layer, the geometry of a particular pathology in the retina, or the like. Clinical parameters may be any such parameter directly observable and measurable with an OCT imaging system, or parameters derived from such direct observables.

The surgical protocol is designed using at least in part one or more of these clinical parameters for guidance. The surgical procedure is initiated using the initial parameters (block 2945). The NA (block 2947) and the focus for brightness on procedure ROI (block 2955) are adjusted to optimize visualization of the procedure. Additional images are acquired (block 2957), and the surgical procedure continues at least in part in response to the visualized OCT images. The NA (block 2965) and the focus for brightness on procedure ROI (block 2967) are adjusted, if needed, either to improve the image quality, or to observe structures that may be secondarily impacted by the procedure. For example, during a cataract procedure, it may be desirable to visualize the retina to observe any traction transmitted to the retina. Secondary implications observable to the surgeon with the OCT will be understood by the surgeon as expert in the art. More images are acquired using the new settings (block 2975). As the procedure nears completion, a new set of clinical parameters are computed based on the subsequently acquired images and associated settings (block 2977). The initial clinical parameters and the new clinical parameters are compared (block 2985) and a determination whether the desired results have been achieved is made (block 2987). If the desired results have been achieved (block 2987), operations cease. If, on the other hand, the desired results are not achieved (block 2987), then operations return to block 2945 and repeat until the desired results are achieved.

Figure 30:
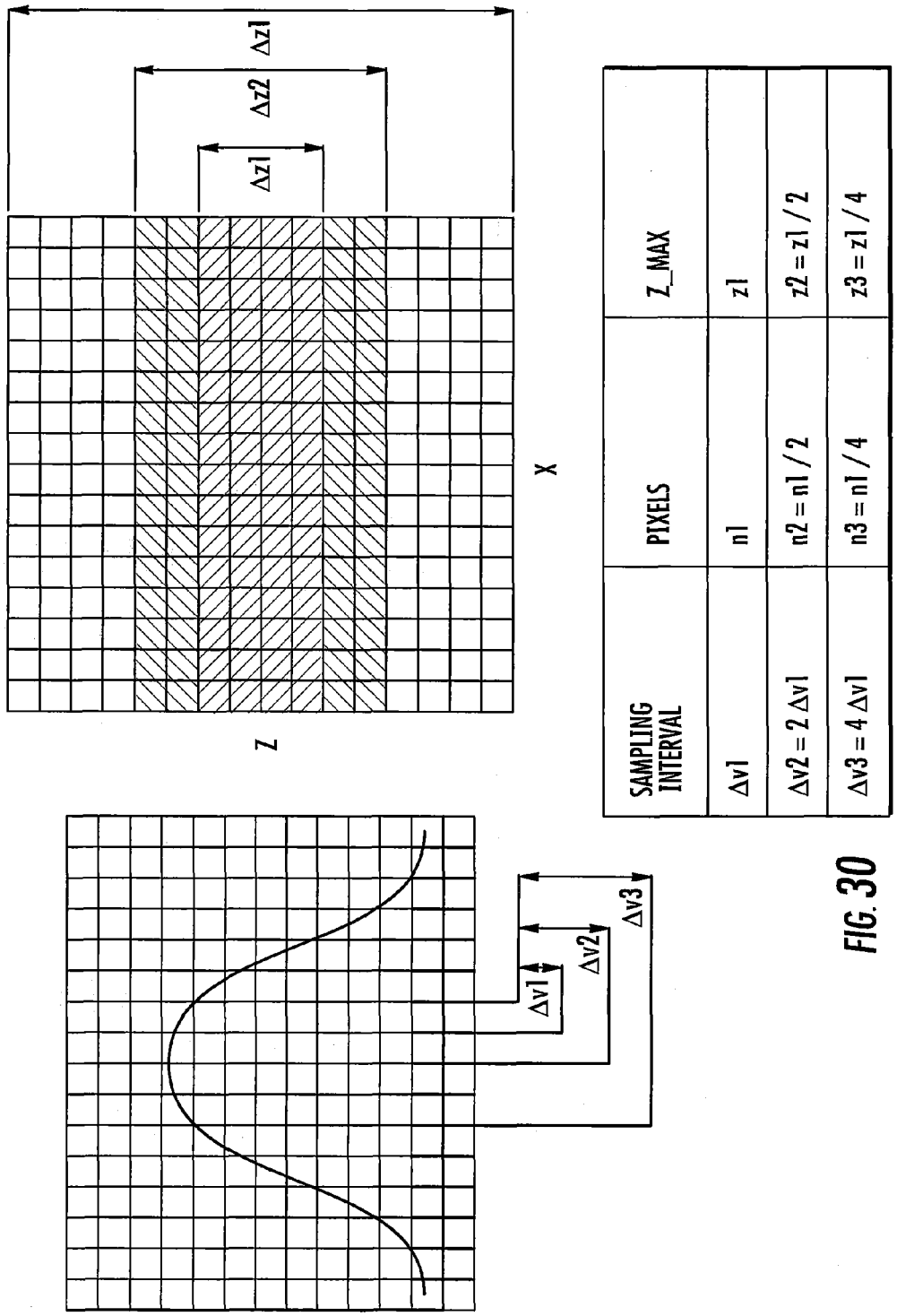
FIG. 30 is a series of charts illustrating image depth of field adjustment through selection of spectral sampling interval in accordance with some embodiments of the present inventive concept.

As an adjunct to controlling the OCT depth of field through NA control, the (Fourier domain) window depth may adjusted by controlling the spectral sampling interval, as illustrated in FIG. 30. Referring now to FIG. 30, a series of charts illustrating image depth of field adjustment through selection of spectral sampling interval in accordance with some embodiments of the present inventive concept will be discussed.

As is now well known in the art, the FDOCT image window is a function of the spectral sampling interval. The maximum observable image window depth corresponds to the minimum spectral sampling interval. In a spectral domain system, a spectrometer pixel spacing constrains the image depth. In a swept source system, hardware constraints on spectral sampling set the constraint. On the other hand, the observable image depth may be halved or quartered by doubling or quadrupling the spectral sampling interval. With a fixed spectral range, the resolution is not impacted, the window depth is reduced, and the number of pixels is correspondingly reduced. This process has the advantage of displaying only the region of interest, when a constrained region of interest is targeted, and may do so at less computation cost, because the number of data points is reduced. In this fashion, there is increased focus on the region of interest, reduced computational cost, and potentially faster acquisition and display for faster feedback to the surgeon.

Figure 31:
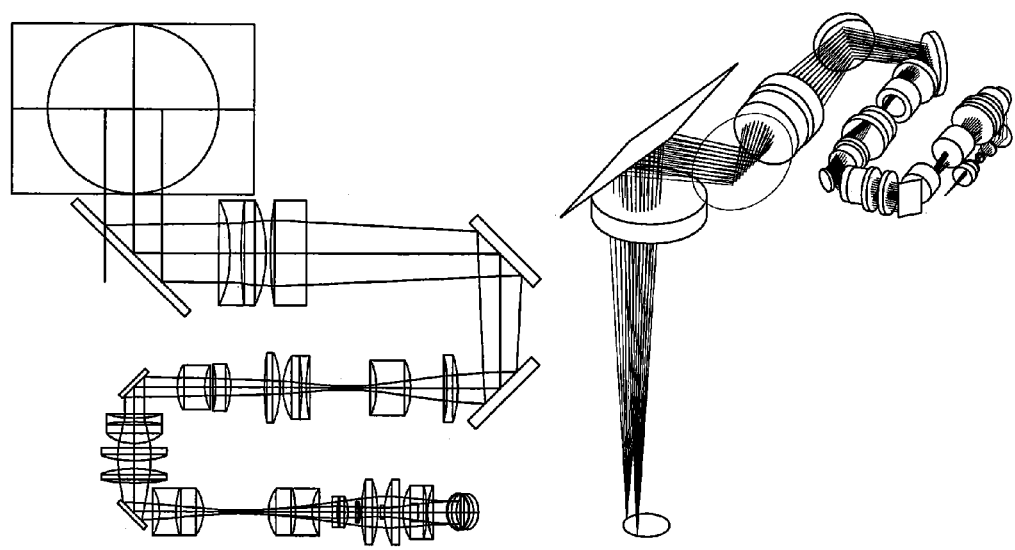
FIG. 31 is a diagram illustrating an optical layout for an OCT-integrated microscope in accordance with some embodiments of the present inventive concept.

Referring now to FIG. 31, a diagram illustrating one embodiment of an OCT optical system in accordance with some embodiments of the present inventive concept will be discussed. In this embodiment, the system was configured to correct for higher-order aberrations over the required scan range, resulting in the system shown in FIG. 31. This optical system design was fine-tuned to reduce back-reflections that couple efficiently into the source fiber in order to reduce noise in the OCT signal. The system illustrated in FIG. 31 contains 13 singlets and 7 doublets (all with spherical surfaces) which can be folded up to fit into a 50 mm×125 mm×150 mm volume.

Figure 1D:
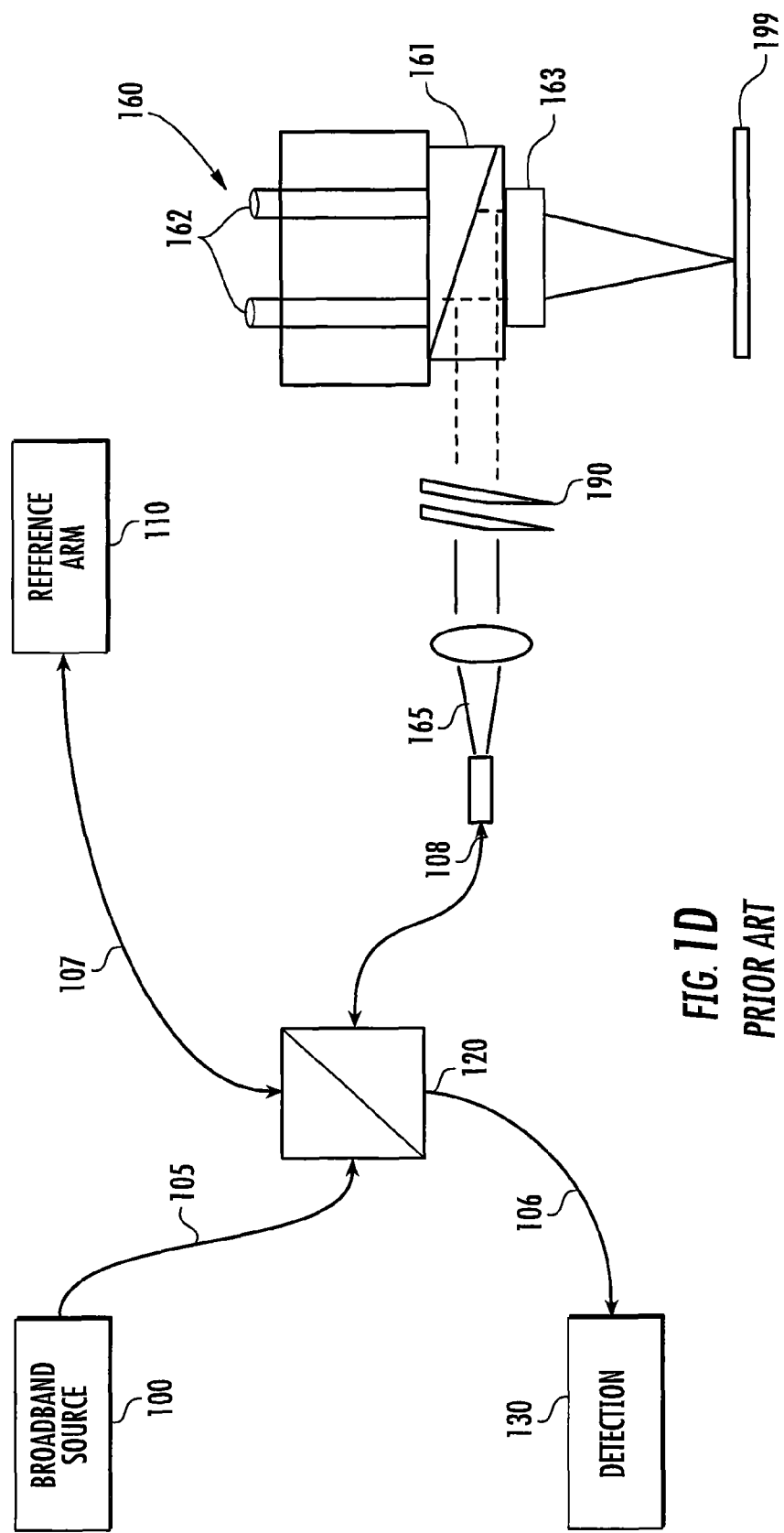
FIG. 1D is a block diagram illustrating an example surgical microscope.
Figure 1E:
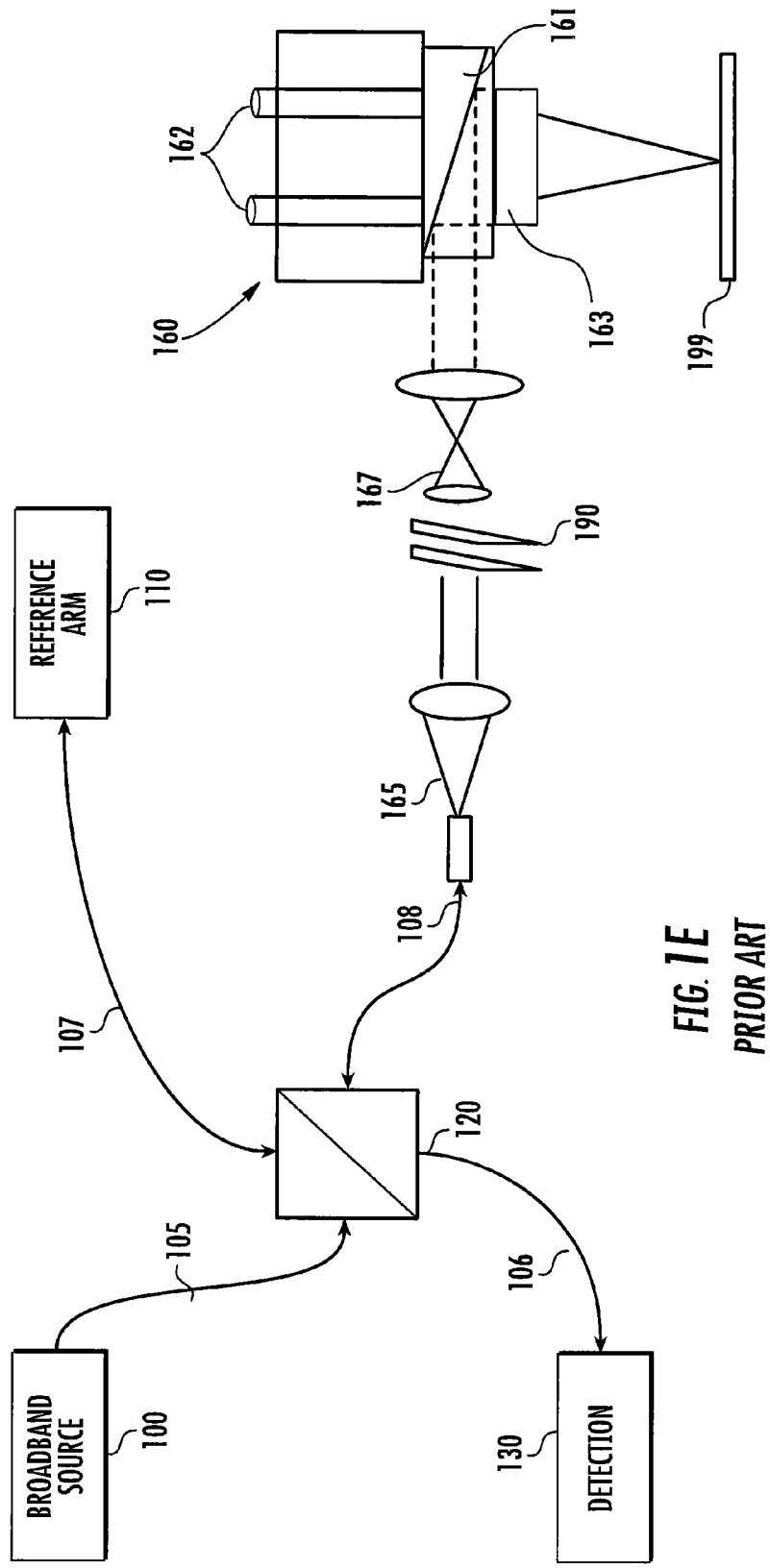
FIG. 1E is a block diagram illustrating an example surgical microscope including a telescoping lens set.

Finally, OCT optical systems in accordance with some embodiments discussed herein can perform optimally for the specific microscope objective or range of microscope objectives for which it is designed. In contrast to both diagnostic ophthalmic OCT systems and laboratory microscopes, surgical microscopes have very long working distances, ranging typically from about 150 mm to about 175 mm, but extending from about 125 mm to about 200 mm. Furthermore, the concept of OCT integration into laboratory microscopes has already been commercialized by Bioptigen, as illustrated in FIG. 1D for a system with a 75 mm objective focal length. Additionally, the microscope objective is designed with demands of surgical imaging (or laboratory imaging) and color correction in mind. These design objectives are not always immediately consistent with the requirements of high quality OCT imaging. Further, the variety of surgical systems and applications means that this OCT interface must adapt to a wide variety of microscope objectives, laboratory, and surgical applications.

To provide the most flexible OCT interface, the architecture of the system is divided into two subsystems that we will call the OCT Relay and the OCT Objective. The OCT Relay as described provides flexibility in controlling the numerical aperture and focal control of the OCT system. The OCT Objective is the final multiple-lens system that includes the microscope objective and sets the exit pupil of the OCT system, including any back focal length accommodation. The exit pupil should be positioned at the front focal plane of the microscope objective. The OCT Objective can be tailored to any microscope objective, with the virtual exit pupil reducing the mechanical constraints of placing a real exit pupil. Additionally the multi-lens element preceding the microscope objective is useful for setting a focal bias to the OCT system relative to the microscope system, allowing the focal control of the Input Beam Zoom to optimize the focus around this bias point for increased control and optimization of the OCT image.

The features of the present inventive concept extend the range of utility of this Microscope OCT interface from the long working distance of a surgical microscope to the shorter working distances of a laboratory microscope.

Example embodiments are described above with reference to block diagrams and/or flowchart illustrations of systems and devices. The functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. An optical coherence tomography (OCT) system for integration with a stereo microscope, the OCT system comprising:
    a sample arm coupled to the imaging path of a stereo microscope, the sample arm comprising:
        an input beam zoom assembly including at least two movable lenses configured to provide shape control for an OCT signal beam;
        a scan assembly following the input beam zoom including at least one scanning mirror and configured for telecentric scanning of the OCT signal beam; and
        relay optics following the scan assembly including a beam expander configured to set the OCT signal beam diameter incident on the stereo microscope main objective;
    a dichroic beamsplitter positioned within an infinity space of the stereo microscope and between the relay optics and the stereo microscope main objective;
    wherein the shape control includes separable controls for numerical aperture and focal position of the imaged OCT beam that operate by coordinated motion of the movable lenses within the input beam zoom assembly;
    wherein the stereo microscope main objective is configured to image in a visible spectral range;
    wherein the stereo microscope main objective is anti-reflection coated for a visible spectral range and an infrared spectral range; and
    wherein the relay optics including a beam expander comprises optics to pre-compensate aberration of the OCT signal beam in an infrared spectral range arising from the stereo microscope main objective configured for imaging in a visible spectral range.

2. The OCT system of claim 1, wherein the beamsplitter is set at an angle of not less than 48 degrees and not greater than 55 degrees relative to the optical axis of the stereo microscope main objective.

3. The OCT system of claim 1, wherein a path length adjustment is included in the sample arm between the beam expander and the stereo microscope main objective to accommodate for variances in the focal length of the stereo microscope main objective.

4. The OCT system of claim 1, wherein the telecentric scan assembly comprises a first scanning mirror having an image relayed onto a second scanning mirror and wherein an exit pupil of the OCT sample arm is in the back focal plane of the stereo microscope main objective.

5. The OCT system of claim 4, wherein the exit pupil of the OCT sample arm optics comprise a virtual exit pupil.

6. The OCT system of claim 1:
   wherein the input beam zoom comprises first and second positive lenses and a negative lens therebetween; and
   wherein a numerical aperture of the system is set by controlling a first distance between the first positive lens and the negative lens and a second distance between the negative lens and the second positive lens.

7. The OCT system of claim 6, wherein a focus of the OCT system is set by controlling a position of the second positive lens for a particular setting of numerical aperture.

8. The OCT system of claim 1:
   wherein at least a portion of the OCT path occupies a center channel of the stereo microscope;
   wherein the OCT beam is directed towards a center field of the stereo microscope main objective; and
   wherein any ocular paths of the stereo microscope are situated peripherally to this center field of the stereo microscope main objective.

9. The OCT system of claim 1, wherein the beamsplitter occupies an area less than a clear aperture of the stereo microscope main objective.

10. The OCT system of claim 1, wherein the sample is an eye.

11. The OCT system of claim 10, wherein a retinal imaging lens assembly is situated between the stereo microscope main objective and the eye.

12. The OCT system of claim 11, wherein the retinal imaging lens assembly images a conjugate of the scanning mirrors to a position posterior to a pupil plane of eye.

13. The OCT system of claim 12, wherein retinal imaging lens assembly includes at least one lens with at least one aspheric surface.

14. The OCT system of claim 1, further comprising an objective lens in common with a stereo microscope, wherein the objective lens is anti-reflection coated for operation in a visible spectral range relevant to the microscope visualization and an infrared spectral range relevant to the OCT system.

15. The OCT system of claim 14, wherein the stereo microscope main objective is an achromatic doublet comprising a crown glass positive lens component and flint glass negative lens component.

16. The OCT system of claim 1, wherein the system comprises a telecentric scanning system and wherein the system includes one of an entrance pupil and exit pupil at infinity for an image space or object space telecentric system, respectively.

17. The OCT system of claim 16, wherein the telecentric scanning system scans such that magnification is preserved for all points in object space and wherein a scanning beam is parallel to an optical access across a field of view.

* * * * *